US010772561B2

(12) United States Patent
Donaldson

(10) Patent No.: US 10,772,561 B2
(45) Date of Patent: Sep. 15, 2020

(54) SENSORS TO DETERMINE NEURONAL ACTIVITY OF AN ORGANISM TO FACILITATE A HUMAN-MACHINE INTERFACE

(71) Applicant: Thomas Alan Donaldson, Nailsworth (GB)

(72) Inventor: Thomas Alan Donaldson, Nailsworth (GB)

(73) Assignee: Thomas Alan Donaldson, Nailsworth (GB)

( * ) Notice: Subject to any disclaimer, the term of this patent is extended or adjusted under 35 U.S.C. 154(b) by 613 days.

(21) Appl. No.: 15/420,084

(22) Filed: Jan. 30, 2017

(65) Prior Publication Data

US 2017/0281086 A1 Oct. 5, 2017

Related U.S. Application Data

(60) Provisional application No. 62/316,756, filed on Apr. 1, 2016, provisional application No. 62/316,761, filed (Continued)

(51) Int. Cl.
*A61B 5/00* (2006.01)
*A61B 5/04* (2006.01)

(Continued)

(52) U.S. Cl.
CPC ........ *A61B 5/6803* (2013.01); *A61B 5/04001* (2013.01); *A61B 5/04008* (2013.01);

(Continued)

(58) Field of Classification Search
CPC .............. A61B 5/6803; A61B 5/14542; A61B 5/04001; A61B 5/7278; A61B 5/1118;

(Continued)

(56) References Cited

U.S. PATENT DOCUMENTS 4,819,648 A 4/1989 Ko
6,882,881 B1 * 4/2005 Lesser ....................... A61F 7/12 607/3

(Continued)

FOREIGN PATENT DOCUMENTS

WO 2007138598 A2 12/2007
WO 2017172020 A1 10/2017

OTHER PUBLICATIONS

Ansari, Tahmina N., Non-Final Office Action dated Jan. 17, 2017 for U.S. Appl. No. 14/752,521.

(Continued)

*Primary Examiner* — Sanjay Cattungal
(74) *Attorney, Agent, or Firm* — Kokka & Backus, PC

(57) ABSTRACT

Various embodiments relate generally to electrical and electronic hardware, computer software and systems, and wired and wireless network communications to provide an interface between an organism and other computing machine-based entities, and, more specifically, to sensors that facilitate determination of a state of neural activity with which to associate data representing, for example, an intent and/or a command; to implementations of sensors under control to, for example, modify sensing characteristics to interpolate response signals spatially or temporally, or both, to facilitate determination of a state of neural activity; to the formation or implementation of a data model that includes, for example, data arrangements representative of at least neuronal activity to facilitate determination of a state of neural activity; and to mobile human-machine interface to facilitate control based on neuronal activity of an organism.

12 Claims, 40 Drawing Sheets

Related U.S. Application Data on Apr. 1, 2016, provisional application No. 62/316,769, filed on Apr. 1, 2016, provisional application No. 62/316,775, filed on Apr. 1, 2016.

(51) Int. Cl.

| | |
|---|---|
| ***A61B 5/0478*** | (2006.01) |
| ***A61B 5/145*** | (2006.01) |
| ***A61B 5/11*** | (2006.01) |

(52) U.S. Cl.

CPC .......... *A61B 5/0478* (2013.01); *A61B 5/1118* (2013.01); *A61B 5/14532* (2013.01); *A61B 5/14542* (2013.01); *A61B 5/7278* (2013.01); *A61B 2562/0209* (2013.01); *A61B 2562/0223* (2013.01); *A61B 2562/066* (2013.01)

(58) Field of Classification Search

CPC ............ A61B 5/04008; A61B 5/14532; A61B 5/0478; A61B 2562/0223; A61B 2562/0209; A61B 2562/066

See application file for complete search history.

(56) References Cited

U.S. PATENT DOCUMENTS

| | | | | |
|---|---|---|---|---|
| 8,027,668 | B2 * | 9/2011 | Behzad | H04L 67/22 455/414.3 |
| 8,433,388 | B2 * | 4/2013 | Blunt | G06T 11/006 600/407 |
| 8,786,624 | B2 * | 7/2014 | Echauz | A61B 5/0476 345/440 |
| 8,849,390 | B2 * | 9/2014 | Echauz | A61B 5/4094 600/544 |
| 9,370,309 | B2 * | 6/2016 | Ko | A61B 5/04008 |
| 9,696,801 | B2 | 7/2017 | Donaldson | |
| 2002/0115571 | A1 | 8/2002 | Yokosawa et al. | |
| 2004/0002645 | A1 * | 1/2004 | Ewing | A61B 5/04008 600/409 |
| 2005/0124848 | A1 * | 6/2005 | Holzner | A61B 5/04008 600/9 |
| 2005/0267549 | A1 * | 12/2005 | Della Santina | A61N 1/372 607/57 |
| 2006/0149337 | A1 * | 7/2006 | John | A61N 1/36082 607/45 |
| 2009/0018431 | A1 * | 1/2009 | Feiweier | A61B 5/04008 600/407 |
| 2009/0221896 | A1 * | 9/2009 | Rickert | A61B 5/0478 600/378 |
| 2010/0219820 | A1 * | 9/2010 | Skidmore | A61B 5/04009 324/247 |
| 2012/0016435 | A1 * | 1/2012 | Rom | A61B 5/0482 607/45 |
| 2012/0123289 | A1 * | 5/2012 | Sorenson | A61B 5/0031 600/544 |
| 2012/0203079 | A1 * | 8/2012 | McLaughlin | A61B 5/04012 600/301 |
| 2014/0051044 | A1 * | 2/2014 | Badower | A61B 5/7203 434/236 |
| 2014/0152792 | A1 | 6/2014 | Krueger | |
| 2014/0226131 | A1 | 8/2014 | Lopez et al. | |
| 2015/0272465 | A1 | 10/2015 | Ishii | |
| 2015/0301338 | A1 | 10/2015 | Heugten | |
| 2015/0347733 | A1 | 12/2015 | Tsou et al. | |
| 2015/0378431 | A1 | 12/2015 | Donaldson | |
| 2016/0011658 | A1 | 1/2016 | Lopez et al. | |
| 2018/0008827 | A1 * | 1/2018 | Dolev | A61N 2/006 |

OTHER PUBLICATIONS

Young, Lee W., Notification of Transmittal of the International Search Report and the Written Opinion of the International Searching Authority, or the Declaration, dated Jun. 12, 2017 for International Application No. PCT/US17/15693.

* cited by examiner

SENSORS TO DETERMINE NEURONAL ACTIVITY OF AN ORGANISM TO FACILITATE A HUMAN-MACHINE INTERFACE

CROSS-REFERENCE TO RELATED APPLICATIONS

This application is a nonprovisional patent application that claims the benefit of U.S. Provisional Patent Application No. 62/316,756 filed Apr. 1, 2016 and entitled, "SENSORS TO DETERMINE NEURONAL ACTIVITY OF AN ORGANISM TO FACILITATE A HUMAN-MACHINE INTERFACE"; this application also claims the benefit of U.S. Provisional Patent Application No. 62/316,761 filed Apr. 1, 2016 and entitled, "CONTROL OF SENSORS TO ENHANCE DETERMINATION OF NEURONAL ACTIVITY OF AN ORGANISM TO FACILITATE A HUMAN-MACHINE INTERFACE"; this application also claims the benefit of U.S. Provisional Patent Application No. 62/316,769 filed Apr. 1, 2016 and entitled, "FORMATION AND IMPLEMENTATION OF A NEURONAL ACTIVITY-BASED DATA MODEL FOR DERIVING NEURONAL STATE TO FACILITATE A HUMAN-MACHINE INTERFACE"; this application also claims the benefit of U.S. Provisional Patent Application No. 62/316,775 filed Apr. 1, 2016 and entitled, "MOBILE HUMAN-MACHINE INTERFACE TO FACILITATE CONTROL BASED ON NEURONAL ACTIVITY OF AN ORGANISM"; all of which are hereby incorporated by reference in their entirety for all purposes.

FIELD

Various embodiments relate generally to electrical and electronic hardware, computer software and systems, and wired and wireless network communications to provide an interface between an organism and other computing machine-based entities, and, more specifically, to sensors that facilitate determination of a state of neural activity with which to associate data representing, for example, an intent and/or a command; to implementations of sensors under control to, for example, modify sensing characteristics to interpolate response signals spatially or temporally, or both, to facilitate determination of a state of neural activity; to the formation or implementation of a data model that includes, for example, data arrangements representative of at least neuronal activity to facilitate determination of a state of neural activity. Examples of data arrangements include patterns of one or more types of data, including neuronal activity data; and to mobile human-machine interface to facilitate control based on neuronal activity of an organism.

BACKGROUND

Computing hardware is able to perform greater numbers of computational tasks at faster rates of speed. But the improvements in computer machines and components, such as the implementation of multiple processing units (e.g., central processing units ("CPUs"), graphics processing units, ("GPUs"), etc.), advanced memory devices, and peripheral devices, increasingly are hindered by a human user in the computational loop. In particular, conventional interfaces between human users and computational machines, while functional, are suboptimal for human users to effectively guide the rapid execution of instructions and to consume the information derived therefrom. Therefore, the bandwidth of human user interactions with conventional interfaces, such as keyboards, mice, and other known data-entry devices, are "bottlenecks" that impede the capabilities of known computational machines.

A variety of approaches to provide interfaces to computing machines, while functional, suffer a number of drawbacks. For example, speech recognition applications have been developed with an aim to improve the rate of inputting data over the use of standard keyboards. But typical speech recognition applications are limited by the inaccuracies of interpreting the spoken word and the rate at which human users are able to speak and correct errors, as well as other inefficiencies.

In one approach, conventional diagnostic machines and techniques have been used to derive information from a brain of human to infer a thought so as to, for example, provide an input or request. In some traditional implementations, known sensing techniques are used to coarsely sense a brain activity with limited accuracy. Examples of known sensing techniques relate to magnetoencephalography ("MEG"), magnetic resonance imaging ("MRI"), electroencephalography ("EEG"), electrical impedance tomography ("EIT"), etc. Generally, these techniques are designed to generate imagery (e.g., 3-D images) of a brain or other portions of a human body.

Magnetoencephalography techniques rely on detecting naturally-occurring, intrinsic magnetic fields produced by a brain and its neural currents. Magnetoencephalography, however, requires the use of immobile superconducting quantum interference devices ("SQUID"), which is a drawback in connection with conventional equipment, to detect the relatively very small magnitudes of magnetic fields. The SQUID sensors require cryogenics (e.g., liquid helium at −270° C. or colder), which limits the usage to certain cases due to, for example, the size of magnetoencephalography equipment, and has relatively coarse resolution. A further drawback is that magnetoencephalography equipment, including SQUID sensors, requires relatively large amounts of capital expenditures. A predominant drawback of measuring the naturally-occurring, intrinsic magnetic fields produced by a brain requires the complexities of measuring very, very small magnetic fields, which presents challenges of working with such magnetic fields. In some cases, naturally-occurring, intrinsic magnetic fields produced by a brain may be millions times weaker than the earth's magnetic field.

Magnetic resonance imaging techniques typically employ relatively large magnetic fields and are used principally to generate medically diagnostic imagery of the brain, and, thus suffer some drawbacks when used to detect physiological activity. For example, magnetic resonance imaging machinery generally is limited to tracking indirect effects (e.g., non-neural activity) of a brain, such as blood flow and glucose uptake. As such, the temporal resolution of magnetic resonance imaging techniques is typically low. Another drawback is that magnetic resonance imaging requires relatively large amounts of capital expenditures and immobile equipment that limits usage to predetermined locations, such as medical offices. Electroencephalography techniques typically monitor the naturally-occurring, intrinsic electrical activity as "brain wave." Common approaches typically use small number of electrodes that are sampled relatively slowly. Further, the signal-to-noise ratios of the sensed signals are generally insufficient. For example, an electroencephalography technique may use 256 electrodes that requires contact with the scalp, whereby the signals are sampled at 100 Hz. Thus, the spatial and/or temporal resolution may be less optimal in various implementations. Electrical impedance tomography is a medical imaging technique that employs electrodes with which to determine an impedance of various biological tissues. Principally, electrical impedance tomography requires injecting a current into tissue and sensing a current or voltage from the tissue, whereby the received current or voltage includes impedance information. There are a number of drawbacks with this approach. For example, electrical impedance tomography techniques rely on using electrodes that require contact with the scalp (e.g., the electrodes receiving the electric current impedance data typically are required to be in contact with skin), and the relatively low magnitudes of current that provides for suboptimal temporal resolution, among other things. Further, spatial resolution associated with this approach is limited by the number of electrodes commonly used.

Furthermore, conventional approaches provide data at relatively coarse granularity using relatively high levels of features and low levels of resolution and, thus, are not well-suited to spatially and temporally characterize and correlate neuronal activity, as well as other physiological activity, to identify an intent, thought, or command associated with an organism. Existing man-machine interfaces based on conventional approaches generally are slower, more complex, and typically are associated with latency amounts which render such interfaces impractical for many tasks or uses. For example, some conventional sensing techniques require a determination of a 3-D model of a brain with which to spatialize. These sensing techniques typically have relatively low bandwidths, such as those of EEGs, which relay on high-level features such as alpha and gamma waves and extract coarse levels of data that have limited usage. Existing techniques often require a user to learn to produce a number of easily detectable brain activity patterns, as for example in “biofeedback” techniques, and this limits the range of possible applications.

Thus, what is needed is a solution for facilitating an interface for human users and computational machines, without the limitations of conventional techniques.

BRIEF DESCRIPTION OF THE DRAWINGS

Various embodiments or examples (“examples”) of the invention are disclosed in the following detailed description and the accompanying drawings.

DETAILED DESCRIPTION

Various embodiments or examples may be implemented in numerous ways, including as a system, a process, an apparatus, a user interface, or a series of program instructions on a computer readable medium such as a computer readable storage medium or a computer network where the program instructions are sent over optical, electronic, or wireless communication links. In general, operations of disclosed processes may be performed in an arbitrary order, unless otherwise provided in the claims.

A detailed description of one or more examples is provided below along with accompanying figures. The detailed description is provided in connection with such examples, but is not limited to any particular example. The scope is limited only by the claims, and numerous alternatives, modifications, and equivalents thereof. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Figure 1:
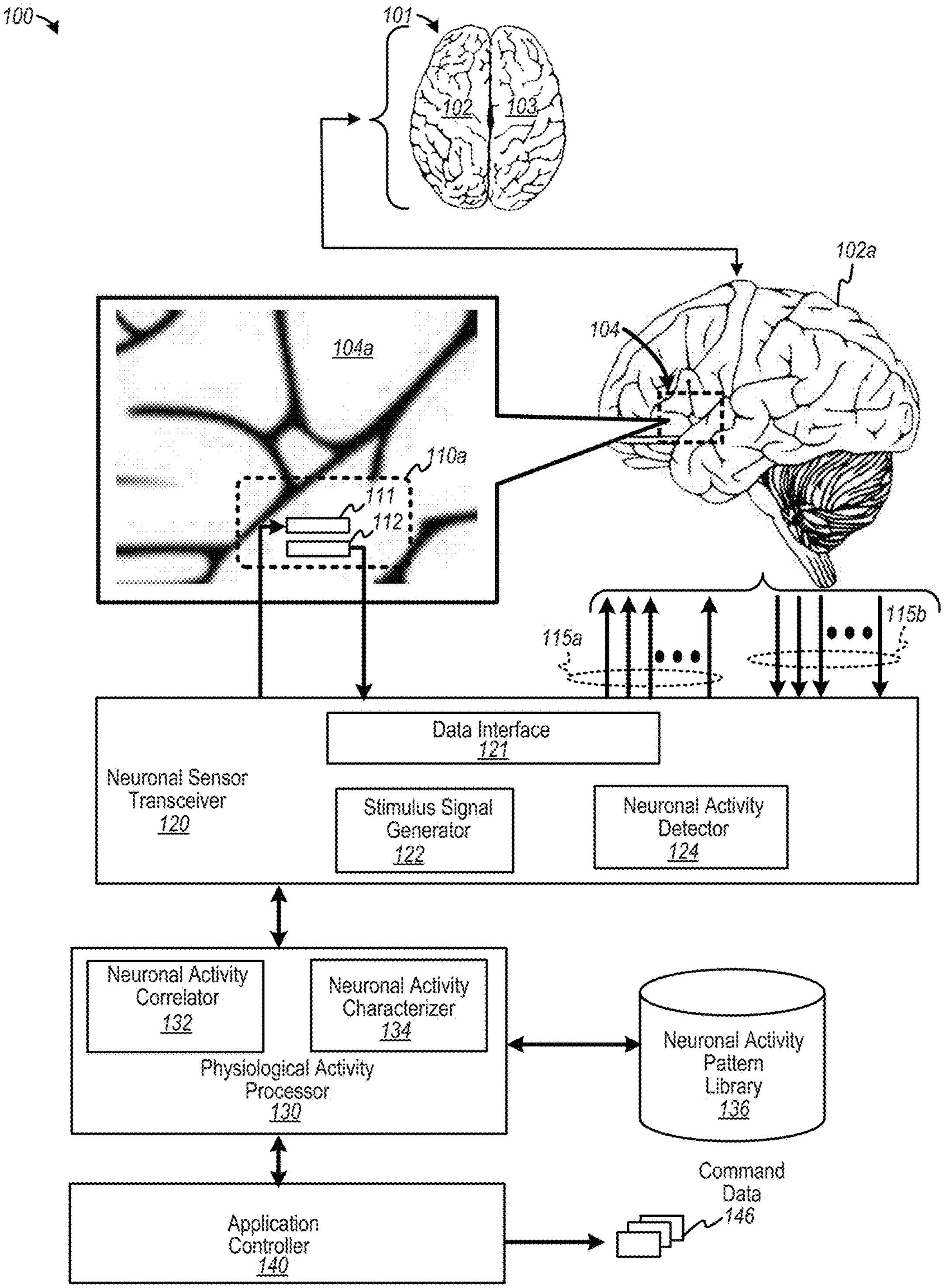
FIG. 1 is a diagram depicting a neuronal activity sensing system to facilitate a human-machine interface, according to some embodiments.

FIG. 1 is a diagram depicting a neuronal activity sensing system to facilitate a human-machine interface, according to some embodiments. Diagram 100 depicts a brain 101 of an organism (e.g., a human user), brain 101 including a left cerebral hemisphere 102 and a right cerebral hemisphere 103, from which neuronal activity of a central nervous system may be sensed to determine a neuronal state. According to various examples, a human-machine interface may include an array (not shown) of one or more neuronal activity sensors 110*a* that are configured to sense a portion of neuronal activity in region 104*a* of left cerebral hemisphere 102*a*. Neuronal sensor transceiver 120 may be coupled to the array of neuronal activity sensors 110*a* to apply stimuli to one or more portions of brain 101 at configurable degrees of resolution. Further, the array of neuronal activity sensors 110*a* are configured to receive responses from the one or more portions of brain 101, whereby the responses include characteristics of neuronal activity with which a type of neuronal activity and a neuronal state may be associated. Examples of neuronal activity types include, but are not limited to, visual activities, auditory activities, tactile sensations, coordinated motor control impulses, memory activities, speech-related activities, emotions, among others, whereby at least some of the aforementioned types may be determined through localized portions of brain 101. A neuronal state may refer, at least in some examples, to a set of one or more patterns of a central nervous system (e.g., spatial and/or temporal patterns of action potentials) that may be associated with a detectable thought, idea, intent (e.g., command), or the like. In some cases, a neuronal state may be identified as a function of the one or more patterns of brain activity (e.g., spatially-related patterns or temporally-related patterns, or both). In some cases, neuronal activity sensor 110*a* may be referred to as a central nervous system ("CNS") sensor.

Diagram 100 further depicts a physiological activity processor 130 and an application controller 140 to facilitate a human-machine interface, according to some examples. Physiological activity processor 130 may be configured to identify instances of neuronal activity that may be used to determine a neuronal state. According to some embodiments, physiological activity processor 130 may be configured to access a database repository 136 including a neuronal activity pattern library to, for example, match responses received from the array of one or more neuronal activity sensors 110*a*. The matched responses constitute one or more states of neuronal activity that may be aggregated to identify a thought or command, whether at an atomic level (e.g., a unit level) or at a macro-level (e.g., multiple thoughts or commands). Physiological activity processor 140 may be further configured to transmit data representing one or more thoughts or commands to application processor 140, which, in turn, may be configured to map one or more thoughts or commands to a function of a particular interface or application, such as a text editor application. Therefore, application processor 140 can generate command data 146 suitable for the text editor application. Examples of command data 146 may include interface commands to navigate an interface (e.g., user interface commands such as up, down, left, right, pan, zoom, etc.). Other examples of command data 146 may include application-specific commands (e.g., identifying a word and performing an "insert" word operation, a back space command, select text command, text formatting commands, etc.). Another example of an application for which command data 146 is generated includes a computer tomography application configured to build a 3D model of activity (e.g., neuronal or non-neuronal activities) within the central nervous system. Thus, diagram 100 depicts examples of various components that may implement a neuronal activity sensing system that facilitates a neuronal-based human-machine interface.

At least a subset of activity sensors 110*a* includes a stimulus signal element 111 and a response signal element 112. Stimulus signal element 111 may be configured to propagate stimulus signals 115*a* into the target region that includes biological tissues or components. Response signal element 112 may be configured to transmit response signals 115*b*, whereby a response signal includes data representing a physiological activity characteristic that may describe, for example, a neuronal activity characteristic. According to some embodiments, an activity sensor 110*a* is a "bio-inductance" sensor that may be configured to sense induced magnetic fields that include data indicative of neural activity sensed by activity sensor 110*a*. In some examples, a magnetic carrier signal or field may originate from biological tissues that is modified (e.g., modulated) by the localized conductivity of, for example, cerebrospinal fluid through which neural currents, including, but not limited to, one or more action potentials (e.g., via transportation of potassium and sodium ions), synaptic currents, and other current sources, including eddy currents (e.g., induced eddy currents), in a central nervous system, any of which may be isolated or aggregated for purposes of quantifying an amount of neuronal activity, according to various examples. In a specific example, stimulus signal element 111 may include one or more electrodes to apply an electric current density (e.g., an electric field) as a stimulus signal field into biological tissue. The electric current density is injected into biological tissues via one or more electrodes, and may be further configured to form an induced field. According to some examples, an alternating current or voltage signal is applied as a stimulus signal to stimulus signal element 111 to generate alternating induced magnetic fields of various frequencies (e.g., ranging from a few Hz to a few hundred MHz, or any suitable other range, such as 100 kHz to 5 MHz or the like). Response signal element 112 of FIG. 1 may include one or more magnetic sensing elements. As an example, response signal element 112 may include, but are not limited to, one or more coils (e.g., one or more search coils) configured to receive one or more alternating magnetic fields with magnetic portions attributable to induced neural current modified by neural activity.

In other one or more specific example, signal element 111 may include one or more magnetic coils that may be configured to receive an alternating electric current of various frequencies to apply a magnetic field density (e.g. a magnetic field) as a stimulus signal field into biological tissue. A magnetic field density may be injected into biological tissues via one or more magnetic coils. Response signal element 112 of FIG. 1 may include one or more coils (e.g. search coils) configured to receive one or more alternating magnetic fields, with magnetic portions attributable to induced neural eddy currents modified by neural activity (i.e., neural currents induced by the stimulus magnetic field density modified by neural activity).

Diagram 100 also depicts a neuronal sensor transceiver 120 that may include a data interface 121, a stimulus signal generator 122, and a neuronal activity detector 124. Stimulus signal generator 122 may be configured to selectably drive a stimulus signal 115*a*, such as an alternating current signal, in association with one or more stimulus signal elements 111, such as one or more electrodes, or one or more magnetic drive coils to generate a stimulus field (e.g., an alternating electric field having varying magnitudes, or a magnetic field having various magnitudes) in the biological tissues with which neuronal activity may be measured. Neuronal activity detector 124 may be configured to receive a response signal that includes data representing an amount of neuron activity. According to some examples, response signal 115*b* received by neuronal activity detector 124 may be an induced current signal indicative of the modified induced magnetic field received into, for example, a coil.

In accordance with some examples, neuronal activity sensors 110*a* and neuronal sensor transceiver 120 may be configured to detect neuronal activity indirectly from biological tissues that include blood vessels and other non-neuronal tissue. As different physiological materials may have different impedance frequency responses, the conductivity of such physiological materials may respond differently to different ranges of drive frequencies responsive to, for example, the magnetic characteristics of non-neuronal physiological material, such as oxygenated blood, deoxygenated blood, glucose, etc. Therefore, a drive frequency can be selected to identify activities related to the different physiological materials. In some embodiments, multiple drive frequencies may be provided simultaneously or in sequence to track these different physiological materials simultaneously (or substantially simultaneously). In some examples, the various different frequencies may be injected into biological tissue using one or more sets of electrodes or magnetic drive coils. To summarize, blood flow, glucose uptake, and other (e.g., non-neuronal) physiological activities may be used as a proxy to indirectly detect or predict neural activity. Furthermore, neuronal activity sensors 110*a* and neuronal sensor transceiver 120 may be configured to detect and characterize neuronal activity based on induced magnetic fields originating from activity associated with both neuronal tissue (e.g., cerebrospinal fluid, neurons, axons, dendrites, etc.) and non-neuronal tissue (e.g., blood vessels, blood, glucose levels, etc.).

In view of the foregoing, the structures and/or functionalities depicted in FIG. 1 illustrate a human-machine interface (or portions thereof) including a neuronal sensing system and other components that can directly or indirectly (e.g., though proxy physiological activities, which may be non-neural activities) detect and characterize neuronal activity of brain 101. According to some embodiments, a neuronal activity sensor 110*a* (or bio-inductance sensor) may be configured to induce currents in a central nervous system through electrodes or magnetic drive coils disposed on or adjacent to a scalp (or a portion thereof), and further configured to detect corresponding induced magnetic fields by magnetic sensing elements at or outside a surface of scalp or skull. In some examples, a sensing elements may be disposed in a range, for example, up to two centimeters (e.g., up to 2 cm or greater) from a skin surface.

According to some examples, stimulus signal generator 122 may be configured to generate an alternating current signal, as a stimulus signal 115*a*, at various frequencies and ranges of frequencies. As such, the greater the alternating frequency of stimulus signal 115*a*, the greater the magnitude of an induced magnetic field that may be generated. Thus, stimulus signal generator 122 may generate an AC signal that is driven at specific ranges of high frequencies to induce a relatively stronger response magnetically (i.e., relative to lower frequencies). Accordingly, stimulus signal generator 122 may be configured to drive stimulus signal at specific frequencies configured to induce certain magnetic responses to detect or measure certain types of biological material through which an induced magnetic field emanates. Stimulus signal generator 122, therefore, can be configured to provide a stimulus signal from which to derive one or more characteristics of a type of tissue through which an induced magnetic field propagates. Examples of various types of biological material or tissue include, but are not limited to, cerebrospinal fluid, axons, dendrites, white cellular brain matter, grey cellular brain matter, as well as blood, glucose, and other materials that may be used either as a proxy for neural activity (e.g., for indirect measurement of neuronal activity) or a contextual characteristic element with which to compare with other sensor data to confirm neuronal activity or a type of neuronal activity, as well as amounts thereof.

Note that data interface 121 of neuronal sensor transceiver 120 may include hardware or software, or both, that is configured to detect an orientation or arrangement of an array of neuronal activity sensors 110*a* relative to one or more reference points, and may be further configured to automatically self-register the array relative to, for example, one or more internal biological structures under a surface of the skin. Therefore, data interface 121 as well as the array of neuronal activity sensors 110*a* facilitates implementation of the human-machine interface (or a portion thereof) as a wearable structure, such as a hat, headband, or the like.

According to yet other examples, response signal element 112 may include multiple components, such as a first component (e.g., a first coil) that may be configured to have a specific sensitivity to surface effects (e.g., scalp or skull currents) and a second component (e.g., a second coil) having another sensitivity to both surface and deeper currents. As such, neuronal activity detector 124 may be configured to subtract one response signal (e.g., induced current at the scalp) from the other response signal to enhance a sensitivity in measuring of particular neuronal activity (or biological material) of interest at a depth from a skin surface. Note that in various examples, an activity sensor may include any number of stimulus signal elements 111 and any number of response signal element 112, and there need not be a one-to-one correspondence to the quantities of stimulus signal elements 111 and response signal element 112. Further, an activity sensor, in some cases, may be composed of either stimulus signal elements 111 or response signal element 112. Different activity sensors may have different amounts of stimulus signal elements 111 and response signal element 112.

According to another example, stimulus signal element 111 may comprise a magnetic drive coil oriented or disposed co-axial (or substantially co-axial) to a response signal element 112. In examples in which response signal element 112 is implemented as a magnetic response coil, stimulus signal element 111 may be position in co-axial alignment with the response signal element 112. Therefore, current induced in response signal element 112 via a stimulus field, such as an induced magnetic field, formed by a stimulus signal originating from stimulus signal element 111. The induced current generated response signal element 112 may be induced through magnetic fields interactions rather than, for example via neuronal activity. Further, the induced current may be minimized, at least in some examples, by ensuring that stimulus signal element 111 is coaxial and substantially centered along an axis with respect to response signal element 112.

Structures and/or functionalities depicted herein set forth a human-machine interface (or portions thereof) that include a neuronal sensing system that can directly or indirectly characterize neuronal activity of brain 101. Consequently, structures and/or functionalities set forth herein may provide central nervous system activity sensing techniques having either enhanced spatial resolution or enhanced temporal resolution, or both. Further, structures and/or functionalities set forth herein may provide for an enhanced dynamic range, as well as an effective direct technique to sense brain activity. Moreover, a human-machine interface according to various examples described herein may provide for a relatively lower cost, lower power, more portable human-machine interface than otherwise may be the case. The human-machine interface also may be able to enhance diagnosis of various disorders, facilitate implementation of enhanced user interfaces, and provide initial insight and analysis of functionality of each human user's central nervous system.

Further to diagram 100, physiological activity processor 130 may also include a neuronal activity correlator 132 and a neuronal activity characterizer 134, according to some examples. Neuronal activity characterizer 134 may include hardware or software, or both, and may be configured to characterize instances of neuronal activity such that each instance of neuronal activity may be decomposed into, or otherwise stored as, a data pattern that is associated with a specific brain activity. In turn, the data pattern may be stored as a data arrangement within neuronal activity pattern library 136. For example, neuronal activity characterizer 134 may be configured to learn (e.g., via deep learning or other types of machine learning, as well as empirically) or otherwise associate identified "thoughts" or "intents" originating from brain 101 with such a pattern. Neuronal activity correlator 132 may include hardware or software, or both, and may be configured to implement the data patterns of repository 136 to identify or categorize detected brain activities from neuronal activity detector 124. Thus, neuronal activity correlator 132 facilitates in-situ operation of an array of neuronal activity sensors 110*a* to effectuate the corresponding human-machine interface, according to various embodiments.

Application controller 140 may include hardware or software, or both, and may be configured to generate command data 146 based on identified neuronal activities, as well as identified non-neuronal activities. Examples of command data 146 data may include instructions (e.g., such as an application programming interface, or API) that invokes a command as a function of detected neuronal or non-neuronal activity. The commands may relate to interface commands, as well as commands or instructions to facilitate communication. In some embodiments, command data 146 may also include instructions to provide an idea or thought that correlates to a particular type of neuronal activity. Therefore, should an organism be thinking of an automobile having a color "blue," the observation (e.g., a thought or idea) may relate to detectable neuronal characteristics constituting neuronal activity states of "blue" and "automobile." Thus, command data 146 may specify the command of presenting a "blue automobile" to a user interface (e.g., a graphical user interface, or GUI).

Figure 2:
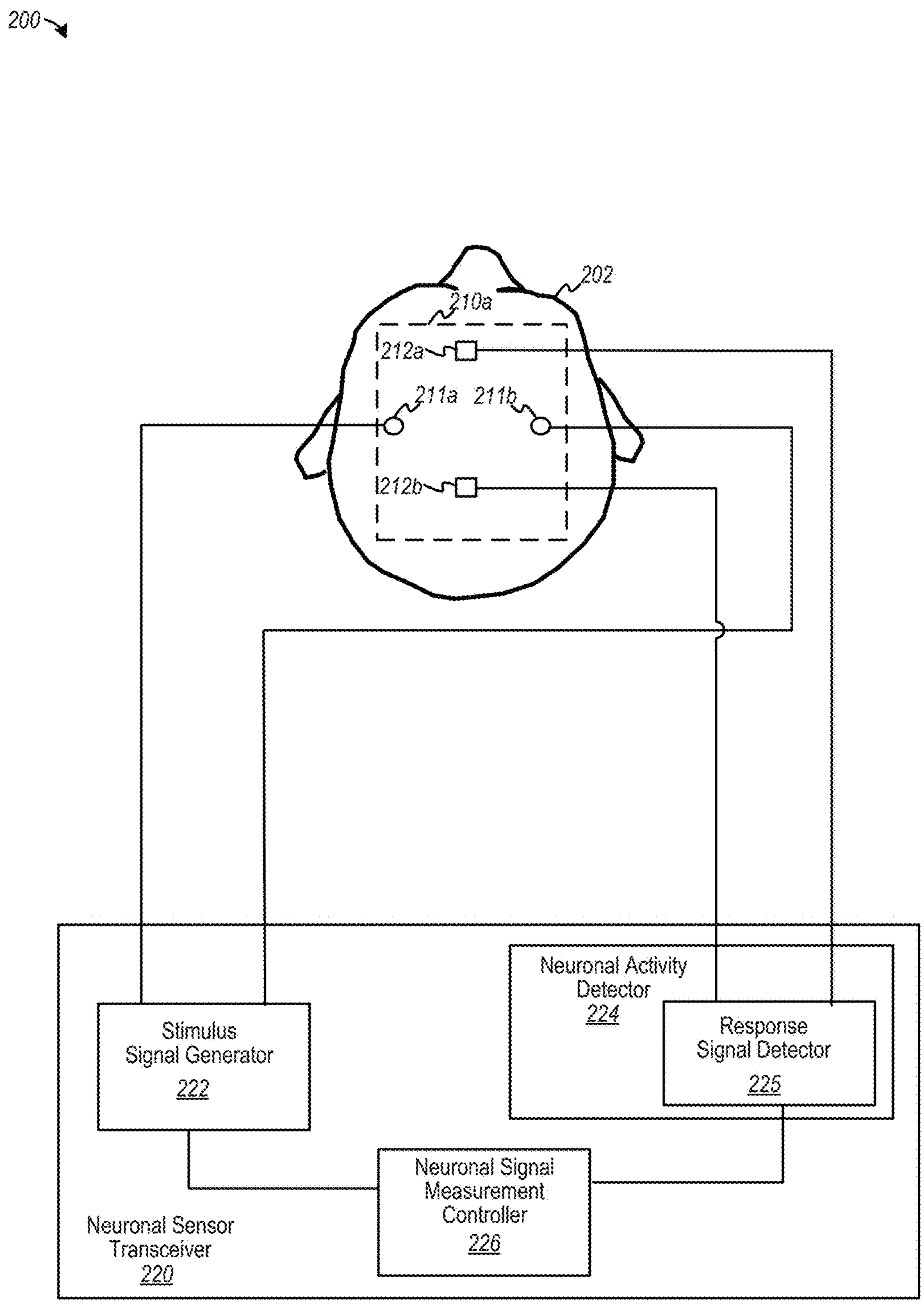
FIG. 2 is a diagram depicting an example of a neuronal sensor transceiver configured to control operation of an example of a neuronal activity sensor, according to some embodiments.

FIG. 2 is a diagram depicting an example of a neuronal sensor transceiver configured to control operation of an example of a neuronal activity sensor, according to some embodiments. Diagram 200 depicts a neuronal activity sensor 210*a* disposed at or adjacent to the surface of skin on the head of a user, and a neuronal sensor transceiver 220. As shown, neuronal sensor transceiver 220 includes a stimulus signal generator 222, a neuronal activity detector 224, which is shown to include a response signal detector 225, and a neuronal signal measurement controller 226. Stimulus signal generator 222 may be configured to generate one or more stimulus signals for driving terminals 211*a* and 211*b*. Response signal detector 225 may be configured to receive one or more response signals from terminals 212*a* and 212*b*. In other examples, neuronal activity sensor 210*a* may include a fewer or greater number of terminals 211 and 212 than is shown. While a single neuronal activity sensor 210*a* is shown, any number of neuronal activity sensors 210*a* may be implemented as part of an array of, for example, 1,000 to 10,000 neuronal activity sensors 210*a*. Note that in some examples, response signal detector 225 may be configured to receive multiple response signals from multiple sensing elements associated with multiple terminals. For example, in some implementations the multiple sensing elements may include multiple coils, at least one of which may be reverse-wound. In this case, neuronal activity detector 224 may be configured to reduce one or more induced currents of one or more coils by an induced current associated with at least one reverse-wound coil, thereby deriving a resultant induced current at a depth of interest. According to some embodiments, stimulus signal generator 222 may be configured to generate one or more stimulus signals at specific frequencies to achieve specific measurements (or detection) of certain types of neural activity at certain depths or regions of a brain. As such, the one or more stimulus signals may be driven at different frequencies to target different depths or materials as the difference frequencies may be absorbed (more or less) at different depths or by certain biological materials.

According to various embodiments, neuronal activity sensor 210*a* may include any type or number of sensing elements. In some examples, terminals 211*a* and 211*b* may be configured as electrodes, and terminals 212*a* and 212*b* may be configured to couple to at least one search coil. Further to this example, electrodes 211*a* and 211*b* may be formed as silver or silver chloride electrodes with or without conducting gel. Electrodes 211*a* and 211*b* may be of any type, including integration into adhesive patches of any configuration or shape. Any other electrode types may be implemented to contact a portion of tissue adjacent a skull, such as electrodes formed as silver-loaded rubber, carbon-loaded rubber, or the like. Further, one or more electrodes 211 may be arranged in any number of implementations. As an example, one or more electrodes 211 may be arranged to effect or tune the sensitivity of neuronal activity sensor 210*a* to a particular activity (e.g., visual activities, auditory activities, tactile sensations, coordinated motor control impulses, memory activities, speech-related activities, emotions, etc.) in a specific part of the central nervous system. A single pair of electrodes 211*a* and 211*b* may be used. Alternatively, any number of pairs of closely-spaced electrodes 211*a* and 211*b* may be disposed at relatively short distance apart from each other at any number of points over a skull.

In accordance with other examples, terminals 211*a* and 211*b* may be configured to couple to a magnetic drive coil as a stimulus element. An example of a magnetic drive coil may be formed from one or more as coils of insulated wire, such as, for example, enameled 32-AWG copper wire. The magnetic drive coil may be configured as circular coil of 100 turns of radius 1 cm, or any other diameter or number of turns. Any other coils configurations may be used. For example, magnetic drive coils may be formed with relatively larger or small radii, with fewer or greater number of turns. Moreover, a magnetic drive coil may include wires of different material compositions or gauges.

Note that in specific implementations, a greater current density may be provided in the layers of the central nervous system near the skull (i.e., near the surfaces of the cerebral cortex). Thus, an array of neuronal activity sensors 210*a* and neuronal sensor transceiver 220 may be adapted to have a greater sensitivity to physiological activity (e.g., neuronal and non-neuronal activity) in the cortex than elsewhere. Stimulus signal generator 222 may be configured to drive the pairs of electrodes 211*a* and 211*b* with either a single drive waveform, or with different waveforms (e.g. different operating frequencies) so as to differentiate current flowing from different electrodes 211 or from magnetic drive coils 211. Electrodes or magnetic drive coils 211*a* and 211*b* may be disposed in groups of relatively larger numbers of electrodes 211 or magnetic drive coils 211 with sufficient density so as to provide greater resolution (e.g., spatial resolution).

In some examples, magnetic sensing element terminals 212*a* and 212*b* may be configured to couple to any type of magnetic sensing element, such as Hall effect sensors, fluxgate sensors, superconducting quantum interference devices ("SQUIDs"), atomic clock-based magnetic field sensors, microelectromechanical systems-based ("MEMS-based") magnetic sensors, among others. Ferrite material may also be used to enhance sensitivity, at least in one example. In implementations in which coils, such as search coils, are used, capacitors may be coupled to a coil to ensure resonance at frequencies that are used in the drive to electrodes 211*a* and 211*b*, and to optionally provide additional gain.

In another example, neuronal activity sensor 210*a* may be configured to operate as a physiological activity sensor to detect either neuronal activity or non-neuronal activity, or both. In one case, terminals 211*a* and 211*b* may be configured to couple to sources of light emission (e.g., one or more LEDs), and terminals 212*a* and 212*b* may be configured to couple to at least one optical sensor (e.g., a photodiode light detector) configured to detect light of various frequencies and/or intensities. Furthermore, stimulus signal generator 222 may be configured to modify the ranges of wavelengths (i.e., frequencies) or the intensity (i.e., magnitude) of light generated at neuronal activity sensor 210*a*. Likewise, neuronal activity detector 224 may be adapted to detect light emanating through biological tissue of interest to determine or characterize an amount of neuronal or non-neuronal activities associated with the tissue. Other types of neuronal activity sensors 210*a* may also be used, such as acoustic sensors, ultrasonic sensors, radio frequency sensors, etc.

Neuronal signal measurement controller 226 may be configured to control which one or more subsets of neuronal activity sensors 210*a* are to receive which stimulus signals having a specific frequency and of specific magnitude. For example, if a specific subset of sensors 210*a* is disposed near a region of interest for a brain, then neuronal signal measurement controller 226 may be configured to enhance the spatial and/or temporal resolution of the subset of sensors 210*a* to sufficiently determine the information of interest. According to various embodiments, neuronal signal measurement controller 226 may cause stimulus signal generator 222 to drive multiple stimulus signals in accordance with frequency division multiplexing ("FDM"), time division multiplexing ("TDM"), code division multiple access ("CDMA"), or any other technique to drive AC stimulus signals into sensor 210*a* associated with a specific location or time. Note that the same frequencies may not be used to drive each set of electrodes 211*a* and 211*b*. As such, different sets of electrodes 211*a* and 211*b* may operate simultaneously (or substantially simultaneously) to scan multiple portions of the brain that may be of interest.

Figure 3A:
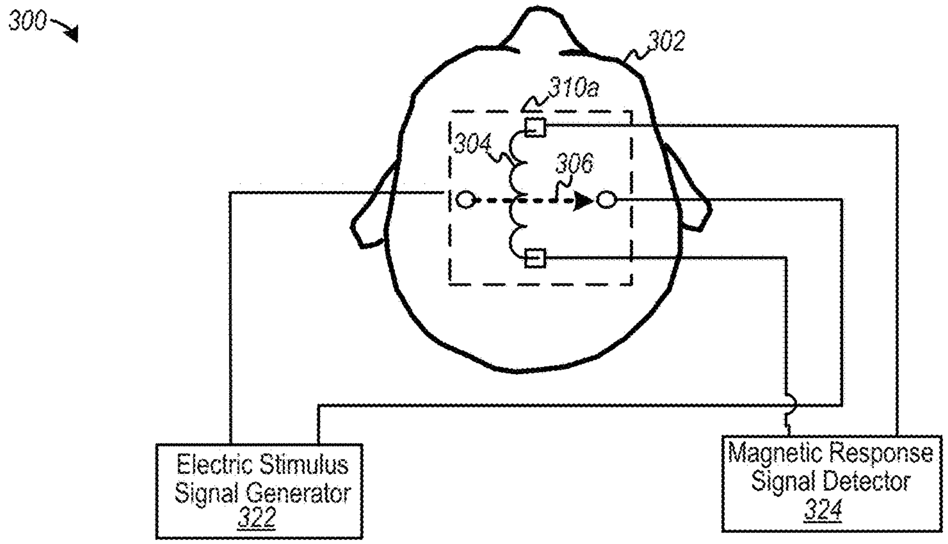
FIG. 3A is a diagram depicting an example of an inductive sensing element of a bio-inductance sensor, according to some embodiments.

FIG. 3A is a diagram depicting an example of an inductive sensing element of a bio-inductance sensor, according to some embodiments. Diagram 300 depicts a bio-inductance sensor 310*a* disposed adjacent to neuronal tissue of the head of a user 302, bio-inductance sensor 310*a* being configured to receive an induced magnetic field generated by current density 306 between electrodes. In this example, electric stimulus signal generator 322 is configured to generate, for example, an alternating current or voltage (e.g., a sinusoidal current of constant amplitude) between electrodes. An exemplary range of stimulus current magnitudes may range from about 1 mA to about 10 mA, or any other suitable range. Magnetic response signal detector 324 may be configured to receive an induced current produced by coil 304 based on an induced magnetic field.

In some embodiments, inductive sensing element 304 may include a coil having a diameter ranging, for example, from 3 mm to 1 cm, or any other range of dimensions. The coil may also include any number of turns. In one example, the coil may include 500 turns. In a specific case, an array may be composed of 3 mm search coils including 500 turns of relatively fine wire disposed at areas to pick up neural activity of interest. In yet another example, coil 304 may be configured as a circular search coil having a 1 cm diameter and about 500 turns of 44-AWG insulated copper wire (e.g., forming a 1 mm×1 mm coil). According to various examples, coil 304 may be implemented with any suitable diameter having any suitable number of turns (i.e., coil 304 is not limited to 500 turns). In view of these exemplary dimensions of coil 304, an array of, for example, 2,000 coils may provide at least 2,000 detectable points of interest over a surface of the head. Other quantities of coils (other than 2,000) are also possible, such as 3,000 to 4,000, or greater, such as 10,000.

Figure 3B:
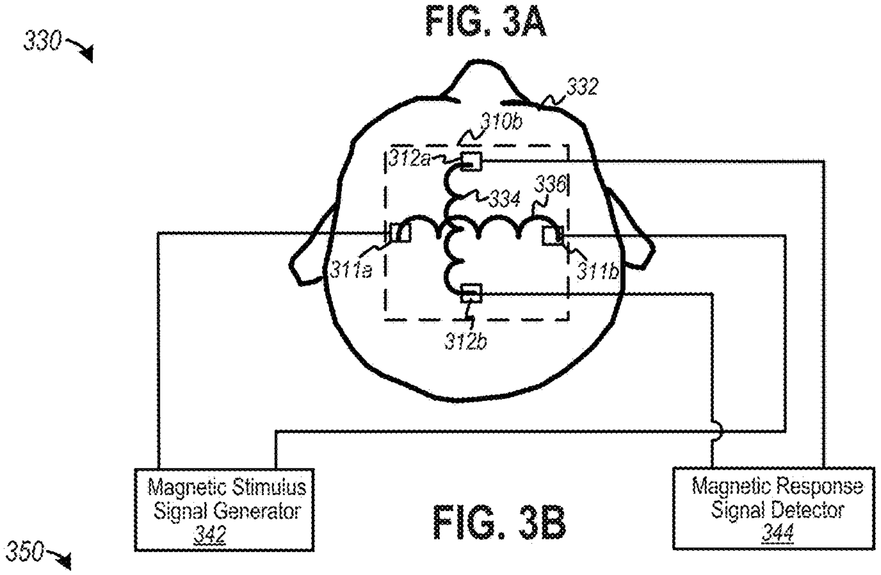
FIG. 3B is a diagram depicting an inductive sensing element and a stimulus signal element of another of a bio-inductance sensor, according to some embodiments.

FIG. 3B is a diagram depicting an inductive sensing element and a stimulus signal element of another of a bio-inductance sensor, according to some embodiments. Diagram 330 depicts a bio-inductance sensor 310*b* disposed adjacent to neuronal tissue of the head of a user 332, bio-inductance sensor 310*b* being configured to receive an induced magnetic field generated by a magnetic drive coil 336. In this example, magnetic stimulus signal generator 342 is coupled via terminals 311*a* and 311*b*, and is further configured to generate, for example, an alternating current or voltage (e.g., a sinusoidal current of constant amplitude) for application to magnetic drive coil 336. An exemplary range of stimulus current magnitudes to apply to a magnetic drive coil may range from 1 mA to about 100 mA, or any suitable range, depending on, for example, a coil size and a number of turns of the magnetic drive coil. Magnetic response signal detector 344 is coupled via terminals 312*a* and 312*b*, and may be further configured to receive an induced current produced by coil 334 based on an induced magnetic field.

Figure 3C:
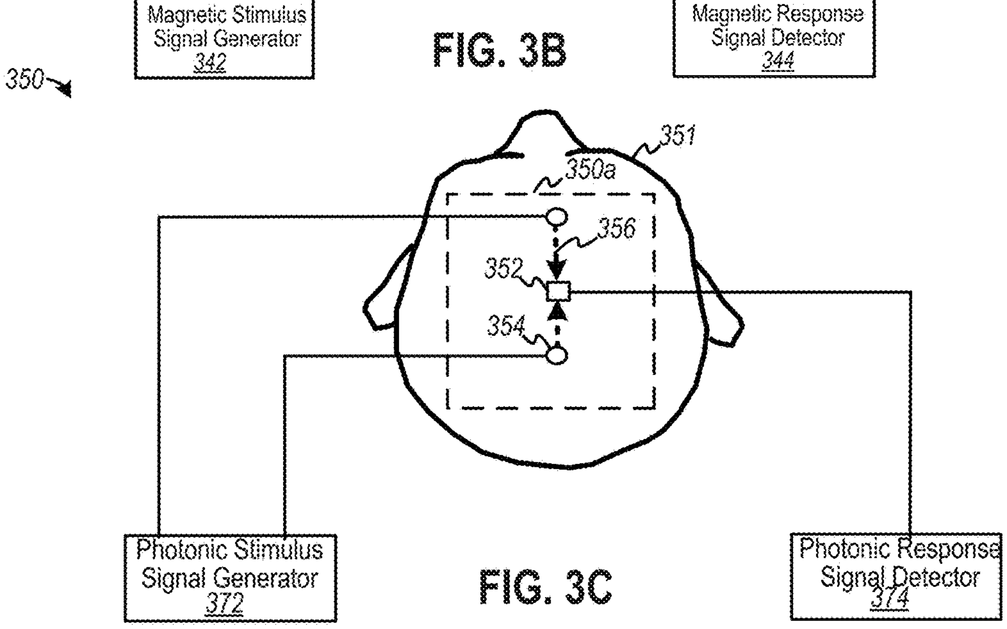
FIG. 3C is a diagram depicting an example of an arrangement of a photonic drive element and a photonic sensing element, according to some embodiments.

FIG. 3C is a diagram depicting an example of an arrangement of a photonic drive element and a photonic sensing element, according to some embodiments. Diagram 350 depicts a physiological activity sensor 350*a* disposed adjacent to neuronal tissue of the head of a user 351, physiological activity sensor 350*a* being configured to receive a light field (e.g., modified by biologic characteristics) originating within or adjacent tissues (e.g., tissue of interest). In this example, photonic stimulus signal generator 372 is coupled via terminals to light-emitting devices 354, and is further configured to generate, for example, one or more light fields having, for example, one or more variable or constant intensities at one or more wavelengths (or ranges of wavelengths) for application to, for example, LEDs 354. An exemplary range of stimulus wavelengths include those for visible light and infrared light spectra. Photonic response signal detector 374 is coupled via terminals to an optical sensor (e.g., one or more photodiodes), and may be further configured to receive the light field from, for example, tissue including a blood vessel (e.g., a cerebral artery or vein).

Figure 3D:
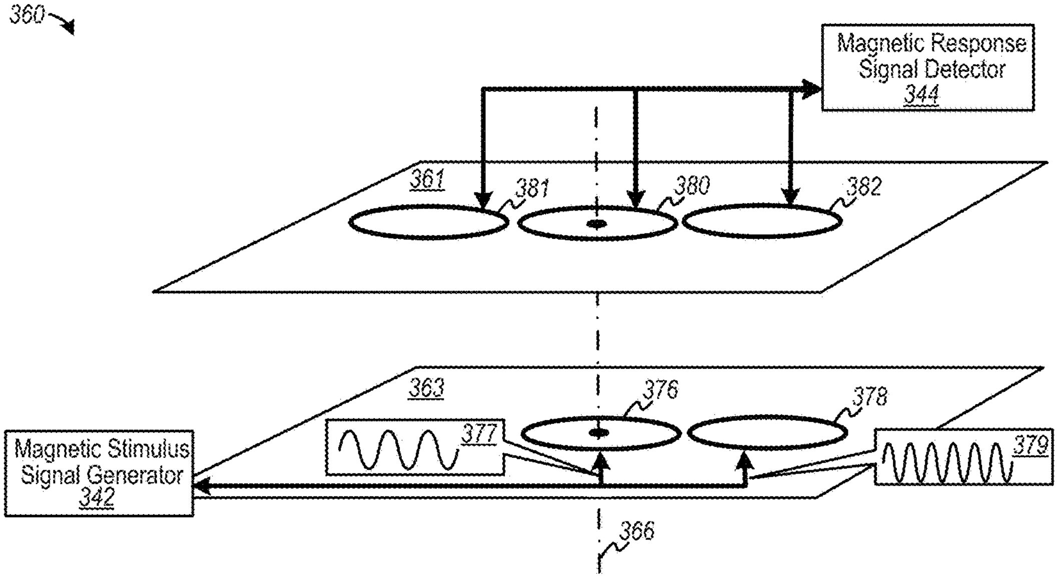
FIG. 3D is a diagram depicting an example of an arrangement of a magnetic drive element and a magnetic sensing element, according to some embodiments.

FIG. 3D is a diagram depicting an example of an arrangement of a magnetic drive element and a magnetic sensing element, according to some embodiments. Diagram 360 depicts a bio-inductance sensor including a magnetic drive coil 376 as a stimuli element, and a magnetic sensing coil 380 (e.g., a search coil) as a response element, both of which are disposed coaxially relative to reference line 366. As shown, magnetic drive coil 376 and magnetic sensing coil 380 are disposed in layers 363 and 361, respectively. As magnetic drive coil 376 is coaxial to magnetic sensing coil 380, the received response signal (e.g., induced magnetic field) into coil 380 may be enhanced or maximized. Drive coil 376 and pickup coil 380 may be arranged such that the net field generated in pickup coil 380 by drive coil 376 may be negligible or zero. For example, drive coil 376 may be constructed in two parts, once reverse wound compared to the other, the first part disposed towards one end of pickup coil 380 and the other part disposed towards the opposite end of pickup coil 380, such that the currents induced in pickup coil 380 by each part of drive coil 376 cancel each other out, while a magnetic field emanating from each end may be non-zero. As another example, pickup coil 380 may be configured to receive induced currents originating in the brain rather than elsewhere. This may provide for enhanced sensitivity.

Further to diagram 360, a magnetic stimulus signal generator 342 may be configured to drive one or more sinusoidal currents into magnetic drive coils 376 and 378, both of which generate a drive magnetic field that enters a head of a user. The induced magnetic fields cause the generation of currents (e.g., eddy currents) in the cerebrospinal fluid, whereby the magnitude of the eddy currents may be related to neuronal activity and an amount thereof. Eddy currents are currents that can be detected similar to currents injected into tissue through an electric field formed using electrodes. Eddy current may, at least in some cases, may be more locally detectable, which may enhance resolution.

Magnetic response signal detector 344 may be configured to receive induced currents, which may include data representing the eddy currents. Magnetic response signal detector 344 may be configured to separate or filter induced magnetic fields having different ranges of frequencies, as well as corresponding induced currents. For example, consider that magnetic sensing coils 381 and 382, which are neighboring pickup coils adjacent coil 380, may receive some of the induced current in the brain. To enhance spatial resolution and signal-to-noise ("SNR"), magnetic stimulus signal generator 342 may be configured to drive stimulus currents into magnetic drive coils 376 and 378 at one or more different frequencies. To illustrate, consider that a first stimulus current is driven into magnetic drive coil 370 at a first frequency 377, whereas a second stimulus current is driven into magnetic drive coil 378 at a second frequency 379.

Magnetic response signal detector 344 may be configured to separate (e.g., filter) the effects of different drive coils 376 and 378 on different pickup coils 381, 380, and 382. Further, Magnetic response signal detector 344 may be configured to combine similar induced current signals at a given frequency (e.g., associated with a particular drive coil) in different combinations to enhance spatial resolution. Also, magnetic response signal detector 344 may be configured to correlate any number of induced current signals (with different frequencies) to corresponding drive coils, whereby the identification, and, thus, location, of each drive coil may be used to enhance spatial resolution. For example, pickup coil 382 may receive magnetic fields originating at drive coils 376 and 378, which have different frequencies and corresponding locations in an array of coils. Also by combining multiple coils over a larger area, the sensitivity may be enhanced equivalent to a larger, and more sensitive pickup while retaining spatial resolution.

Figure 4:
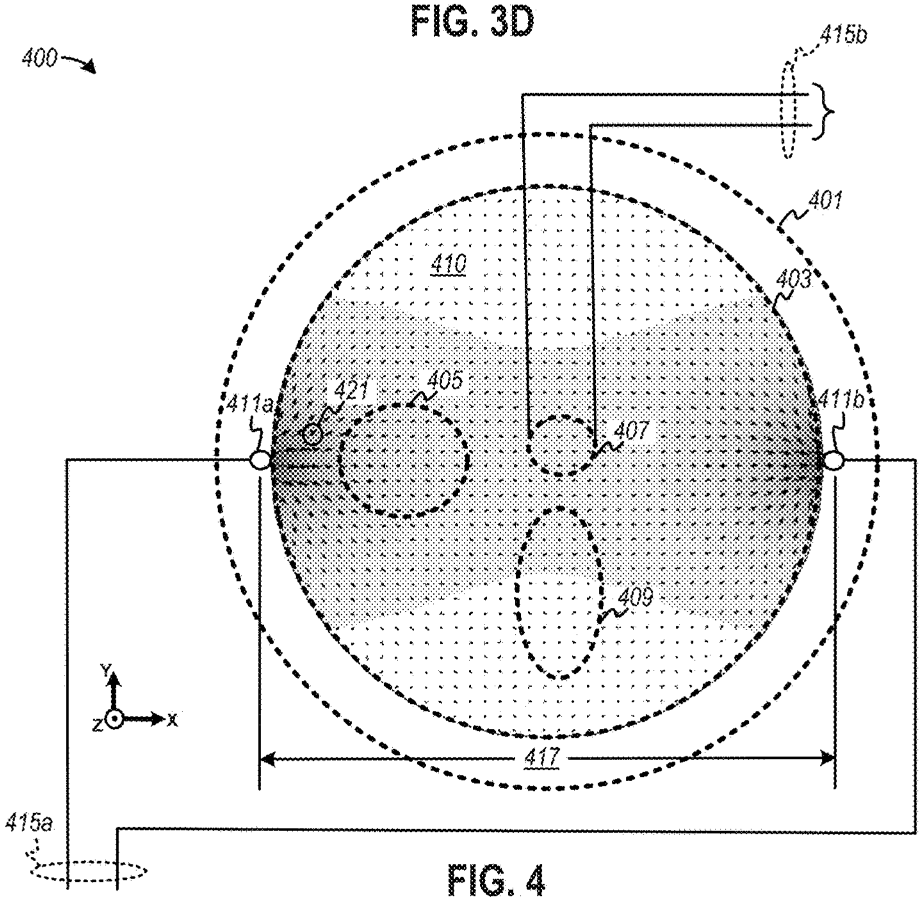
FIG. 4 is a diagram depicting an example of a stimulus field and examples of the dimensions of inductive sensing elements, according to some examples.

FIG. 4 is a diagram depicting an example of a stimulus field and examples of the dimensions of inductive sensing elements, according to some examples. Diagram 400 depicts electrodes 411*a* and 411*b* configured to generate an electric field 410 in which a current (e.g., associated with a certain current density) flows between electrodes 411*a* and 411*b*. As shown, electrodes 411*a* and 411*b* are configured to receive one or more stimulus signals transmitted via paths 415*a*. Magnetically-induced response signal, such as the magnetic field associate with induced currents, may be transmitted to a magnetic response signal detector (not shown) via paths 415*b*. As shown, a magnitude of current may be driven in a direction substantially parallel to a layer (e.g., a layer substantially coextensive with an XY plane) including the one or more electrodes 411*a* and 411*b*. Diagram 400 further depicts a variety of dimensions for different inductive sensors. For example, inductive sensor 401 is shown to have an area that encompasses one or more electrodes 411*a* and 411*b* and thus has a diameter larger than the distance 417 between electrodes 411*a* and 411*b*. Inductive sensor 403 is shown to have an area having a diameter equivalent to distance 417. Inductive sensors 405, 407, and 409 are examples that have dimensions smaller than distance 417. As such, multiple instances of inductive sensors 405, 407, and 409 may be implemented in an area defined by distance 470. Note that while inductive sensors 405, 407, and 409 have reduced cross-sectional areas, which, in turn, may be associated with less magnetic flux, these inductive sensors may be designed to detect, for example, a localized neural activity at relatively shallow depths (e.g., at or near the surface of a brain) with higher resolutions. Furthermore, inductive sensors shown in diagram 400 and need not be limited to circular loops, but may have any shape, such as an elliptical shape of inductive sensor 409.

According to one example, a sinusoidal current of constant amplitude may be applied between electrodes 411*a* and 411*b*, which, in turn, induce current flow in a central nervous system (as well as through a skull and a scalp). An example of current flow is shown in FIG. 4, whereby each arrow 421 represents a vector or gradient (e.g., a direction and a magnitude) of a current referenced with respect to 0 degrees of phase for the stimulus signal. Note that in each region of a central nervous system between electrodes 411*a* and 411*b*, an induced alternating current with a direction and magnitude may be generated as a function of the distribution of conductivity in the central nervous system. Note, too, that the conductivity of a region of the central nervous system may be directly related to central nervous system activity. Thus, when a neuron fires, the transport of ions across a cell wall causes a change in conductance responsive to the changing ion concentrations in nearby extra-cellular space that includes cerebrospinal fluid. As current flow is greater in regions of higher conductance, a current density distribution may be related to a conductance distribution. Hence, a current at each point in an induced electric field 410 may be related to both a local and a global conductivity of a cerebrospinal fluid, and, in turn, a central nervous system activity. The rate at which a current may change at any point may be based on a frequency of a drive/stimulus signal (e.g., a sinusoidal stimulus signal may be associated with a particular frequency).

Moreover, a changing current produces a magnetic field that may be related both to the size of the current and the rate of change of the current. As the magnetic field is a function of the current, the magnetic field at each point within a central nervous system may be a function of the central nervous system activity as well. A magnetic sensor or sensing element disposed at or on a surface of the head may detect a net magnetic field, which may be a combination of the influences of the individual points as detected at the sensor. According to some examples, the magnetic field at a surface of skin may be affected by central nervous system activity, and may vary from one sensor position to another sensor position. Therefore, the use of sensors at different position may produce different "views" of the central nervous system activity.

A net magnetic field (i.e., the magnetic field at any sensor) may vary responsive to the variability of a drive current varies, according to some examples. Correspondingly, the frequency of the magnetically-generated field varied may alternate (e.g., as a sinusoidal waveform) at the same frequency (or substantially the same frequency) as the AC stimulus drive signal. Note, however, the phase of the magnetically-generated field may be shifted relative to the drive signal. Further, a neuronal activity detector (not shown) or a magnetic response signal detector (not shown), such as described herein, may be configured to detect such phase shifts between magnetically-generated fields and corresponding drive signals to select a subset of signals that may correspond to a specific drive waveform. Hence, the sensitivity of the detector may be enhanced, with or without a reduction in noise by, for example, implementing bandpass filtering, synchronous detection, demodulation, and similar known techniques.

In view of the various examples described herein, a neuronal activity sensing system may be relatively immune to other magnetic effects, such as the Earth's magnetic field or stray magnetic fields (e.g., electrical machine-based magnetics) in a particular environment, and thus may have greater suitability (e.g., sensitivity) than, for example, magnetoencephalography sensors and equipment. Note further that, according to some examples, a stimulus signal generator (not shown) may be configured to implement a drive frequency that is higher than a frequency of one or more signals of interest. That is, the frequency of central nervous system activity may response a first range of frequencies, whereas the drive frequency may be a second range of frequencies that are higher than the first range. Thus, a neuronal activity detector and/or a magnetic response signal detector may implement oversampling techniques to enhance the sensitivity of the system.

Figure 5:
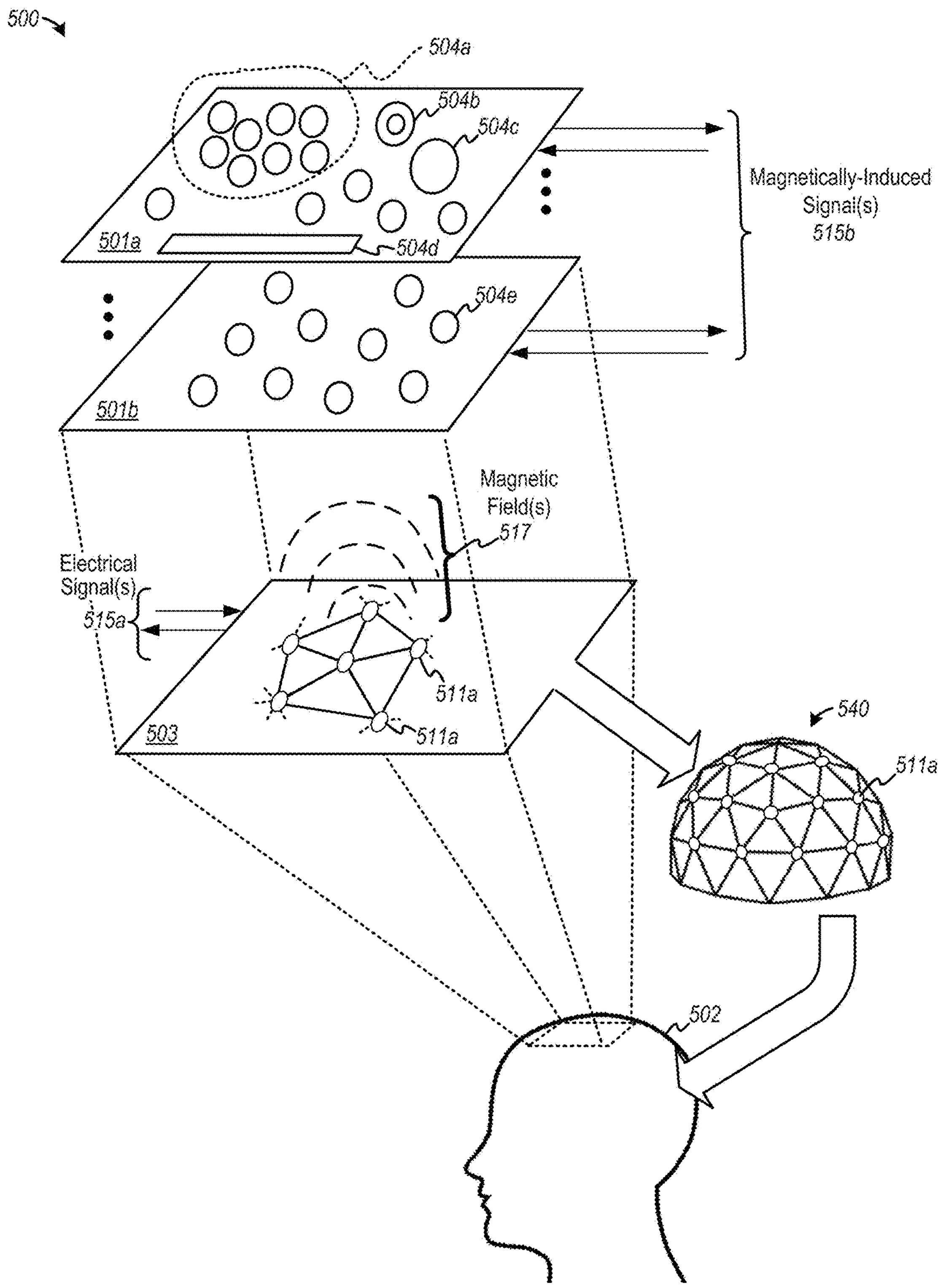
FIG. 5 is a diagram illustrating an example of constituent components of an array of physiological activity sensors adapted to couple to a head of a user, according to some examples.

FIG. 5 is a diagram illustrating an example of constituent components of an array of physiological activity sensors adapted to couple to a head of a user, according to some examples. Diagram 500 depicts examples of layers in which stimulus signal elements, such as electrodes or magnetic drive coils 511*a*, and response signal elements, such as coils 504, are disposed to form a wearable array 540 of physiological activity sensors (e.g., a wearable array of neuronal activity sensors) that is conformed to a head 502 of a user. As shown, one or more layers 503 may include arrays or sub-arrays of any type or shape of electrodes or magnetic drive coils 511*a*, the one or more layers 503 being configured to receive electrical signals 515*a* as, for example, alternating current drive signals at one or more frequencies, which may be driven in accordance with time division multiplexing, frequency division multiplexing, or the like. One or more layers 501*a* and 501*b* may include arrays or sub-arrays of any type or shape of coils 504, the one or more layers 501*a* and 501*b* being configured to receive magnetically-induced fields 517. Coils of 504 may be configured to selectably generate magnetically-induced signals 515*b* as, for example, induced currents (e.g., at one or more frequencies, with optional phased-shifting).

Magnetic-sensing elements may be implemented as any of coils 504, according to some examples. In some examples, layer 501*b* may include similarly-dimensioned coils 504*e* distributed equivalently in layer 501*b* (e.g., coils 504*e* may be evenly-space from each other). As such, the density of coils 504*e* (per unit area) may be relatively constant over the surface of layer 501*b*. According to other examples, coils 504*a* to 504*d* may be each configured with different shapes or dimensions, and may be distributed over the surface of layer 501*a* such that the density of coils 504 may be non-linear or otherwise variable. For example, a portion of layer 501*a* may include a relatively more dense cluster of coils 504*a* than other portions (e.g., to enhance resolution at the clustered portion of layer 501*a*), whereby the density of the cluster of coils 504*a* may be positioned and adapted to sense neuronal activity associated, for example, a specific brain portion (e.g., a speech-related center in a brain). Coils 504*c* and 504*d* may be configured to have different dimensions than other coils. In some cases, magnetic-sensing element 504*b* may include multiple coils, such as one coil nested within another coil. Each of the multiple coils may be formed similarly or differently (e.g., multiple coils may have different number of turns and may be wound in different directions, such as clockwise and counter-clockwise).

In some examples, coils 504 in one layer may be isolated magnetically (or electrically) from other layers of coils 504, whereby coils 504 may be coupled to high-impedance signal receiver circuitry, including amplifiers, when unselected. Thus, subsets of coils 504 may be selected to produce induced currents for purposes of physiological (e.g., neuronal) activity sensing. Note that layers 501*a* and 501*b* may be formed in any fashion with layer 503. Layers 501*a* and 501*b* may be disposed over layer 503 (as shown), under layer 503, or with layer 503 interleaved between layers 501*a* and 501*b*. In some cases, layers 501*a* and 501*b* may be formed in a single or multi-layer spiral coils on a rigid or flexible printed circuit board ("PCB"), which optionally may include layer 503 (e.g., layers 501*a*, 501*b*, and 503 may be integrated into one or more layers). Note that the magnetically-sensing elements may have multiple functionalities, such as operating to detect neuronal activity in a first mode into detect subcranial structures with which to automatically register or orient functionalities of electrodes 511*a* and magnetic-sensing elements 512.

While FIG. 5 depicts layer 503 formed in association with a geodesic structure, the array of physiological activity sensors need not be so limiting and may be form in any type of arrangement or structure. According to some examples, coils 504 may be arranged to be positioned at or on a scalp, or within a suitable distance from either the scalp or skull (e.g., coils 504 may be positioned within 2 cm from the scalp or skull, or greater at a point of interest). As there may be sufficient magnitudes of current passing through the scalp, the current may be dependent (e.g., directly or indirectly) on neural activity. Therefore, the induced current may be an amalgam of what is going on in the brain as indicated by detectable neuronal activity. Further, layer 501*a* or layer 501*b* may include any number of coils (e.g., from a few to hundreds of coils, or up through 3,000 coils or greater, such as 10,000+). An exemplary number of coils is about 2,000 coils. According to some examples, different coils 504 may be driven using different drive signals having different frequencies so as to measure or detect certain types of neural activity at specific depths or regions. In some cases, higher layers of search coils 504 may have larger coils (e.g., larger diameters), which may facilitate deeper sensing of induced magnetic fields (e.g., with lower resolution), whereas lower layers of search coils may be sized with smaller diameters. The smaller coils may facilitate shallower sensing of induced magnetic fields (e.g., skull currents) at relatively finer degrees of resolution to detect activity response signals.

Figure 6:
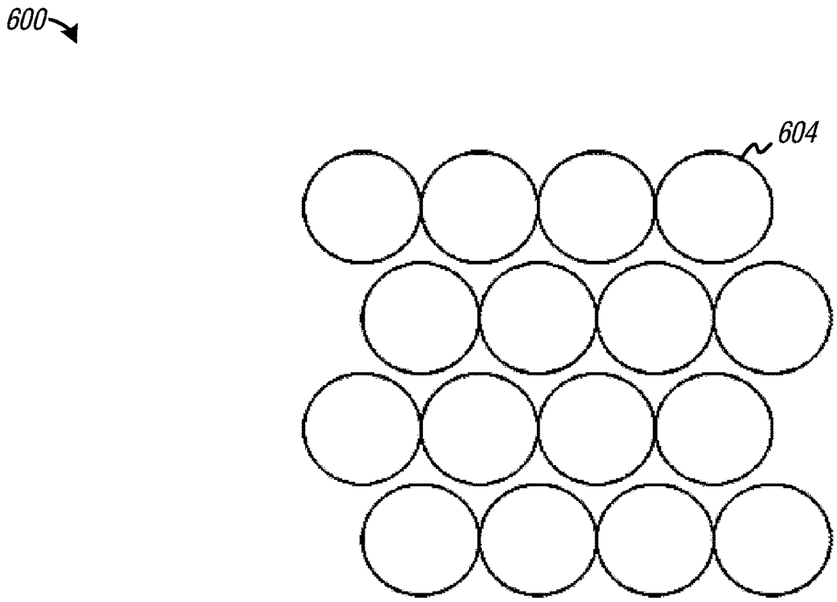
FIG. 6 illustrates an example of an arrangement of inductive-sensing elements, according to some examples.

FIG. 6 illustrates an example of an arrangement of inductive-sensing elements, according to some examples. Diagram 600 depicts an array of coils 604 (e.g., search coils) that may include similarly-dimensioned coils 604 distributed evenly (e.g., substantially evenly) in the array. As such, the density of coils 604 (per unit area) may be relatively constant over a surface of the array.

Figure 7:
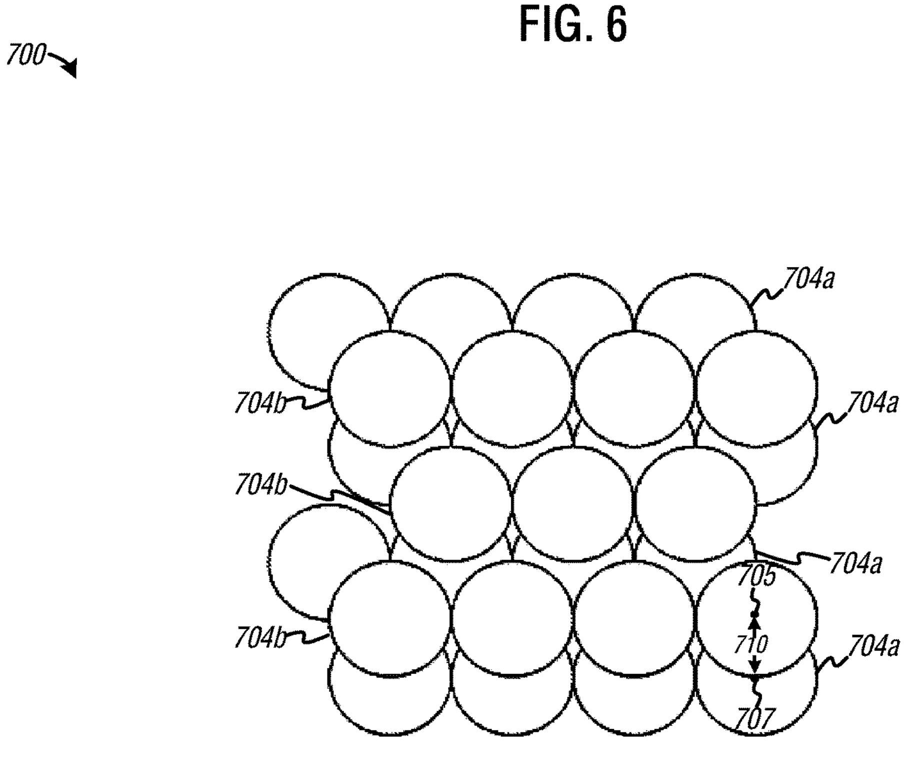
FIG. 7 illustrates another example of an arrangement of inductive-sensing elements, according to some examples.

FIG. 7 illustrates another example of an arrangement of inductive-sensing elements, according to some examples. Diagram 700 depicts a first array of coils 704*b* (e.g., search coils) disposed over a second array of coils 704*a*. Further to the example shown, centers 705 of coils 704*b* may be offset by a distance 710 relative to centers 707 of coils 704*a*. The arrangement of coils 704 depicted in FIG. 7, as well as variants thereof, may effectively increase a number of coils 704 per unit area, thereby enhancing resolution of data derived from the arrangement of inductive-sensing elements. Also, the arrangement of coils 704 depicted in FIG. 7 may also enhance sensitivity of detecting and/or measuring response signals including data representing a magnitude of neuronal activity.

Figure 8:
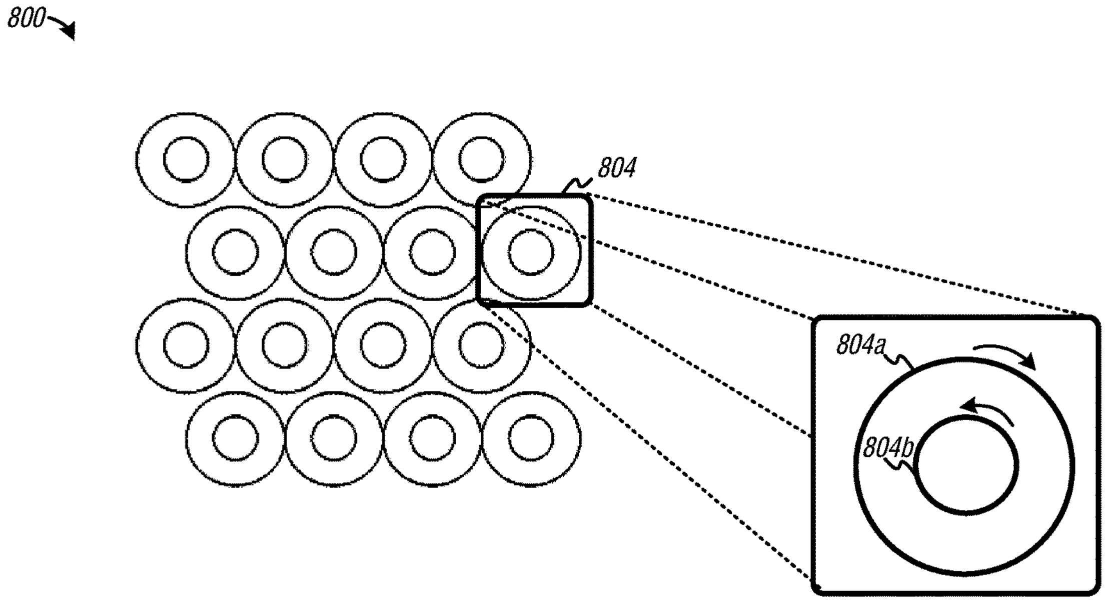
FIG. 8 illustrates yet another example of an arrangement of inductive-sensing elements, according to some examples.

FIG. 8 illustrates yet another example of an arrangement of inductive-sensing elements, according to some examples. Diagram 800 depicts an array of inductive-sensing elements 804 each including a first coil 804*a* (e.g., search coil) having a second coil 804*b* disposed within coil 804*a*. Further to the example shown, first coil 804*a* may be wound clockwise, whereas second coil 804*b* may be reverse-wound in a counter-clockwise direction. According to some examples, inductive-sensing elements 804 may be configured to cancel skull currents. For example, first coil 804*a* may be a larger-sized coil that may sense induced magnetic fields relatively deeper into a scalp (or skull/cranium) than second coil 804*b*, which is smaller in size. In this example, second coil 804*b*, which is a smaller-sized coil, is shown disposed inside larger coil 804*a*. Further, smaller coil 804*b* may be reversed-wound and include more turns than larger coil 804*a*. With more turns, smaller second coil 804*b* may be equally sensitive to a skull current as larger first coil 804*a*, but in the opposite direction. Therefore, smaller reversed-wound coil 804*b* may be disposed in larger coil 804*a* to provide skull current cancellation, whereby the current from the skull current can be canceled out to provide an enhanced dynamic range of operation.

Figure 9A:
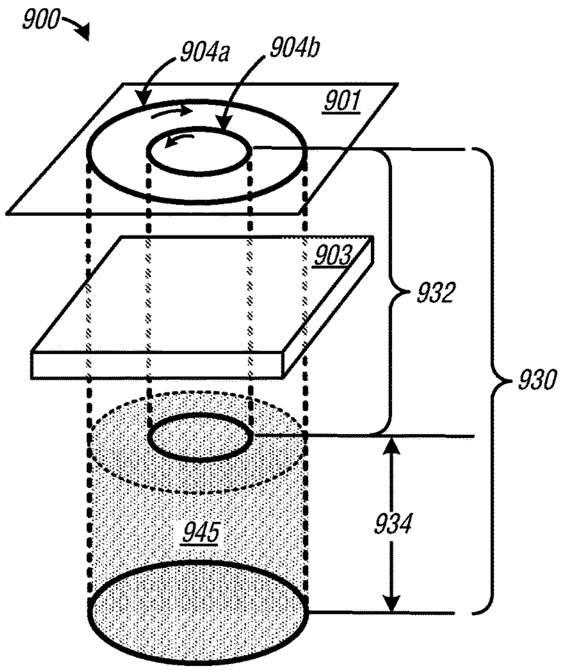
FIGS. 9A and 9B are diagrams depicting examples of various implementations of multiple inductive-sensing elements, according to various examples.
Figure 9B:
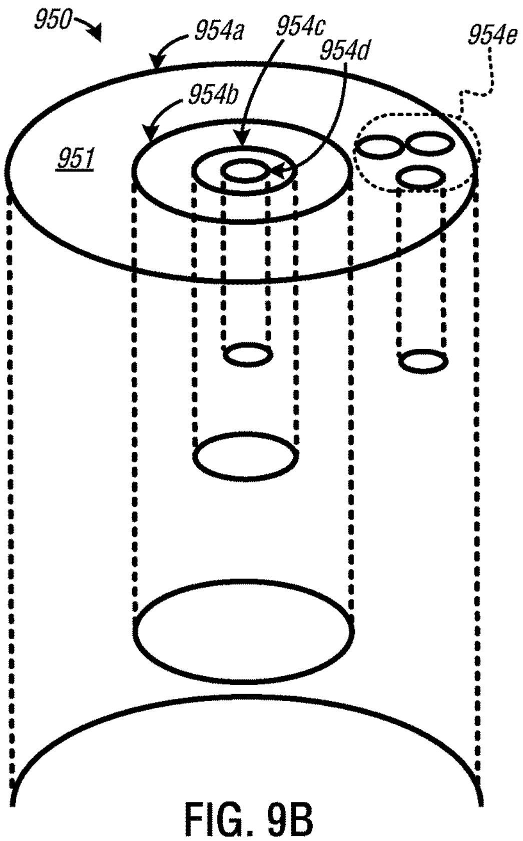

FIGS. 9A and 9B are diagrams depicting examples of various implementations of multiple inductive-sensing elements, according to various examples. Diagram 900 of FIG. 9A depicts inductive-sensing elements including a first coil 904*a* and a second coil 904*b* disposed on, at, or within a range of distances from scalp surface 901. Second coil 904*b*, which is a smaller-sized coil, is shown disposed inside larger coil 904*a*. Further, smaller coil 904*b* may be reversed-wound and include more turns than larger coil 904*a*. With more turns, smaller second coil 904*b* may be equally sensitive to a skull current as larger first coil 904*a*, but in the opposite direction. Therefore, smaller reversed-wound coil 904*b* may be disposed in larger coil 904*a* to provide skull current cancellation, whereby the skull current associated skull portion 903, which includes bone tissue, can be canceled out.

Note that a sensitive region of a search coil 904 may be approximately the same depth along the axis of the coil as the coil diameter, according to some examples. Thus, larger coil 904*a* may be configured to sense deeper into a central nervous system than smaller coil 904*b*. According to at least one specific example, a coil 904 may be configured to receive induced magnetic fields at high frequencies to provide for shorter sensing depths (e.g., shallower cylindrical sensing regions). Or, coil 904 may be configured to receive induced magnetic fields at lower frequencies to provide for longer sensing depths (e.g., deeper cylindrical sensing regions). Therefore, coil 904*a* may be configured to sense induced magnetic fields from surface 901 to depth 930, whereas coil 904*b* may be configured to sense induced magnetic fields from surface 901 to depth 932. Based on the number of turns and the directions of windings for coils 904*a* and 904*b*, induced currents cancel each other out within a region 932. For example, a comparison of depth resolutions of induced currents having high frequencies to induced currents having low frequencies results in region 932 of a cylindrical sensing region being canceled out. Therefore, the difference is portion 945 of the cylindrical sensing region with a depth of 934 (e.g., for induced currents based on low-frequency induced magnetic fields). Further, the sensitivity of the combination of coils 904*a* and 904*b* may be tuned to predominantly sense tissue under skull portion 903 (e.g., with less or negligible sensitivity to scalp currents). In view of the foregoing, such an arrangement may enhance the sensitivity of a neuronal activity sensing system relative to coils 904 configured to sense single frequencies or at common depths.

According to some other embodiments, coil 904*a* may be configured to sense induced magnetic fields from surface 901 to depth 932, whereas coil 904*b* may be configured to sense induced magnetic fields from surface 901 to depth 930, whereby the sensing region is decreased in volume relative to portion 945 of the cylindrical sensing region. Further, coils 904*a* and 904*b* may be configured (e.g., sized, number of turns, etc.) to operate at different frequencies. For example, an induced magnetic field originating from deeper in the brain may be relatively either stronger or weaker than induced currents associated with shallower depths when compared to other frequencies (depending on the effects of central nervous system tissues that attenuate induced magnetic fields at those frequencies). Thus, choosing a frequency may facilitate sensing with variable fidelity relative to different regions that include biological tissue.

Diagram 950 of FIG. 9B depicts an example of another arrangement of inductive-sensing elements including a first coil 954*a*, a second coil 954*b*, a third coil 954*c*, and a fourth coil 954*d*, each of which may be disposed on, at, or within a range of distances from scalp surface 951. As shown, coils 954*a* to 954*d* are arranged as concentric coils configured as an "inverse wedding cake structure" that may implement coil structures 954*a* to 954*d* to provide different levels of sensitivity at different depths into a central nervous system relative to a point or localized region. Therefore, coils 954*a* to 954*d* may be arranged to provide different resolutions at specific locations adjacent a point on interest at or on a portion of a brain.

In some examples, pairs of coils may be selected such that one clockwise coil and one counter-clockwise coil may be selected. For example, consider that coils 954*b* and 954*d* are wound counter-clockwise and coils 954*a* and 954*c* are wound clockwise. Thus, different regions of sensing may be selected by canceling induced currents from one of coils 954*b* and 954*d* with induced currents in one of coils 954*a* and 954*c*. Note while first coil 954*a*, second coil 954*b*, third coil 954*c*, and fourth coil 954*d* are shown to sense depth in decreasing magnitude, other implements of such coils may provide any combination of sensing depths (e.g., by tuning the size and number of turns of each coil). For example, coil 954*d* may be configured to sense induced magnetic fields deeper than coil 954*a*, or any other coil. In some cases, multiple smaller coils 954*e* may be implement within any of coils 954 to enhance amounts of data (and resolution) with which to measure neuronal activity.

Figure 10:
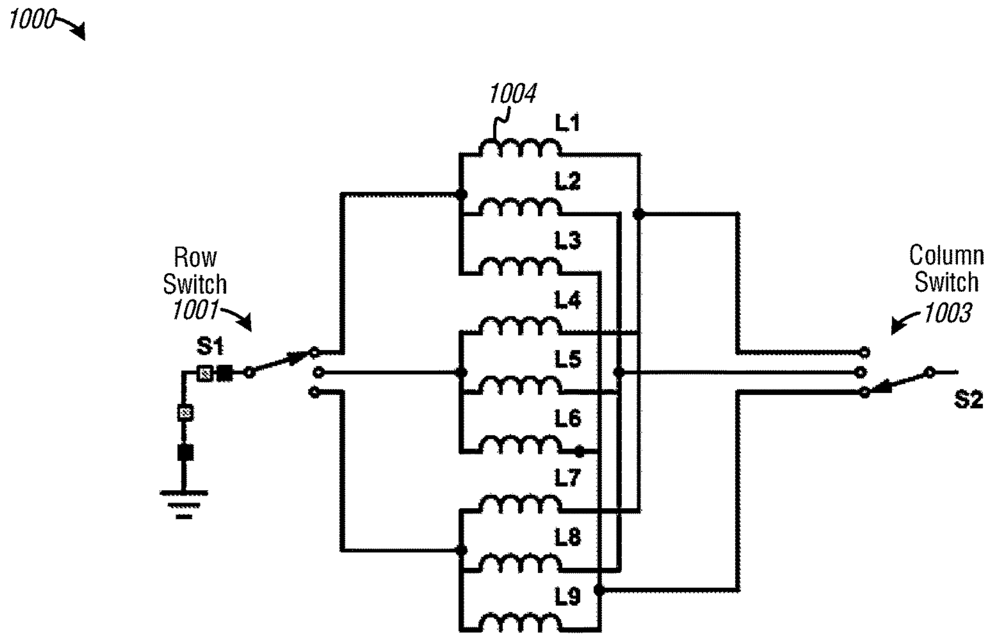
FIG. 10 is a diagram of an example of the configuration of inductive-sensing elements each of which is selectable, according to some examples.

FIG. 10 is a diagram of an example of the configuration of inductive-sensing elements each of which is selectable, according to some examples. Diagram 1000 including a reconfigurable array of magnetic-sensing elements 1004, such as search coils. As shown, magnetic-sensing elements 1004 may be connected in a matrix fashion, indexed by switches, whereby switch 1001 is configured to select a row and switch 1003 is configured to select a column (e.g., row switch 1001 and column switch 1003 are configured to select one coil 1004 from the array). Thus, an induced current associated with a selected coil 1004 may be transmitted to a neuronal activity transceiver (not shown). Accordingly, the reconfigurable array depicted in diagram 1000 facilitates a reduction in a number of measurements systems, system costs, power consumption, weight, size, complexity, etc.

In some examples, the reconfigurable array diagram 1000 may be configured to form larger sensors (e.g., larger-sized coils) using an aggregation of smaller sensors. To illustrate, consider selecting four (4) coils next to each other, such that they can be coupled to form a larger coil to obtain a sensitivity that may be similar to the sensitivity of a larger coil covering the same area. According to some examples, coils 1004 may be disposed in any arrangement described herein, such as arrangements described in FIGS. 6, 7, 8, 9A and 9B, among others.

According to at least some embodiments, coils such as coils 1004 or any other coil described herein may be configured to operate as either a resonant coil or a non-resonant coil (e.g., depending on a specific time interval or mode of operation). As such, coils can be made to operate in or out of resonance with each other. Given a coil size of 1 cm coil and 500 turns, such a coil may have a self-resonance that, when applied to a typical amplifier, may be below the frequencies of interest. However, in some cases, that coil may be operated as a coil out-of-resonance, and the coil may operate using multiple different frequencies. In some cases, these frequencies may have similar responses. Alternatively, according to some other examples, a coil may be operated in a resonance associated with a single band of frequencies of interest, or any frequency of interest that may provide an optimal response. So in this case, a coil may operate in a resonance with a response that may be, for example, a hundred times better than a coil operating out-of-resonance. Note that operating a coil out-of-resonance may provide enhanced temporal resolutions than if operated in resonance. Optionally, the coil may be reconfigured or switched into a resonance to provide for a finer degree of sensitivity.

Figure 11A:
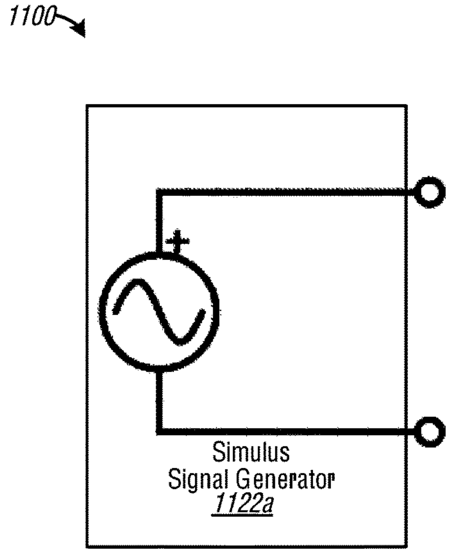
FIGS. 11A and 11B are diagrams depicting examples of various implementations of multiple inductive-sensing elements, according to various examples.
Figure 11B:
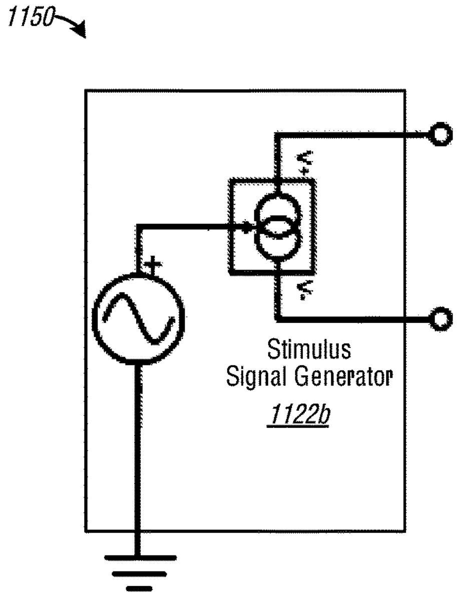

FIGS. 11A and 11B are diagrams depicting examples of various implementations of multiple inductive-sensing elements, according to various examples. Diagram 1100 of FIG. 11A depicts an example of a stimulus signal generator 1122*a* configured to, for example, generate an alternating current signal that may be driven at a specific range of frequencies. As shown, stimulus signal generator 1122*a* may be implemented as an AC voltage source. Diagram 1150 of FIG. 11B depicts another example of a stimulus signal generator 1122*b* configured to, for example, generate another alternating current signal having a configurable range of frequencies with which to drive a stimulus signal. As shown, stimulus signal generator 1122*b* may be implemented as an AC current source.

According to some examples, stimulus signal generators 1122*a* and 1122*b* may be configured to generate a current that induces magnetic signals responsive to operation of stimulus signal generators 1122*a* and 1122*b*, whereby the induced magnetic signals are synchronous (or are substantially synchronous) with the stimulus signal. As such, either synchronous detection may be implemented, or code division multiple access ("CDMA") code may be implemented if using a spread-spectrum technique. Oversampling techniques may be used to improve the signal to noise ratio. Stimulus signal generator 1122*a* may be implemented as a voltage source, including, but not limited to, a waveform generator configured to produce, for example, a sinusoid of 1 V at 50 kHz. Stimulus signal generator 1122*b* may also be implemented as a current source, including a sinusoidal waveform generator that is configured to, for example, generate 1 mA at 50 kHz. According to various examples, any other frequencies, signal shapes and implementations are possible, including square waves, summed sinusoids, ramps, spread spectrum signals and Gaussian noise coded signals, among others. A number of known techniques may be used to control operation of stimulus signal generators 1122*a* and 1122*b*, including direct-digital synthesis, crystal oscillators, microcontroller-based timers, etc. Current source 1122*b* may include operational amplifiers configured as to operate as a currents source, for example. Alternatively, a voltage waveform may be placed on the electrodes using an operational amplifier configured as a voltage source or the like.

FIGS. 12A to 12F are diagrams depicting examples of various implementations of multiple inductive-sensing elements as magnetic pick-up devices, according to various examples. A neuronal activity detector in accordance with various examples may be implemented using any number of structures and/or functionalities, such as any suitable arrangement of analog and mixed signal components, including, but not limited to, instrumentation amplifiers, gain amplifiers, analog-to-digital ("ADC") converters, digital signal processing ("DSP") elements, etc.

Figure 12A:
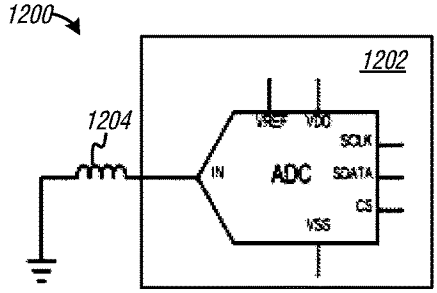
FIGS. 12A to 12F are diagrams depicting examples of various implementations of multiple inductive-sensing elements as magnetic pick-up devices, according to various examples.
Figure 12B:
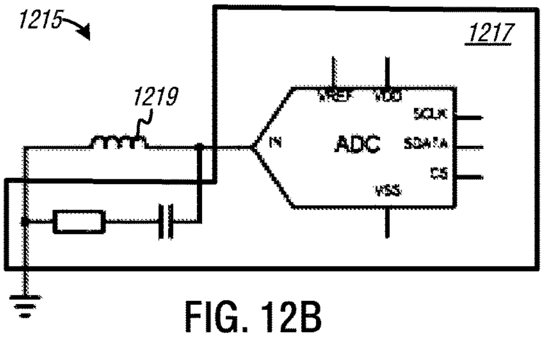

FIG. 12A is a diagram 1200 depicting an example of a neuronal activity detector, according to some examples. In the example shown, neuronal activity detector 1202 may include an analog-to-digital ("ADC") converter (and optional amplifier, which is not shown) configured to couple to a magnetic-sensing element, such as search coil 1204. FIG. 12B is a diagram 1215 depicting another example of a neuronal activity detector, according to some examples. As shown, neuronal activity detector 1217 may include an analog-to-digital ("ADC") converter and a coil 1219 tuned to a resonance provided to the ADC.

Figure 12C:
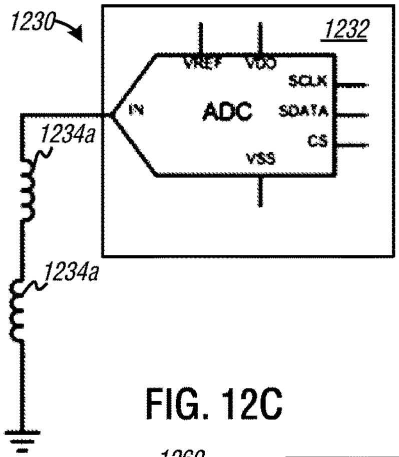

FIG. 12C is a diagram 1230 depicting an example of a neuronal activity detector, according to some examples. In the example shown, neuronal activity detector 1232 may include an analog-to-digital ("ADC") converter configured to couple to multiple a magnetic-sensing elements, such as search coils 1234*a* and 1234*b*, whereby one of search coils 1234*a* and 1234*b* is wound opposite in direction than the other. Thus, search coils 1234*a* and 1234*b* are implemented in a differential manner, which may enhance the dynamic range. In some cases in which coil sensitivities may be sufficiently high enough, coils 1234*a* and 1234*b* may be connected in an opposing fashion. The result is the difference between the two corresponding induced currents, the difference being indicative of a measure of central nervous system activity. Note that this arrangement may be effective for highly-sensitive coils as neuronal activity detector 1232 may configure each coil to have an induced voltage sufficiently above a maximal voltage of the analog-to-digital ("ADC") converter. According to some examples, a single coil 1234 may be used as the "negative" (or cancellation coil) for a number of other coils. Alternatively, any number of coils 1234 may be connected in pairs (e.g., each pair of coils 1234 may be implemented as "deep-shallow" pairs as described above). Note that in some cases in which the coil sensitivity may be less than sufficient, a differential or instrumentation amplifier may be used with two coils as described in FIGS. 12E and 12F.

Figure 12D:
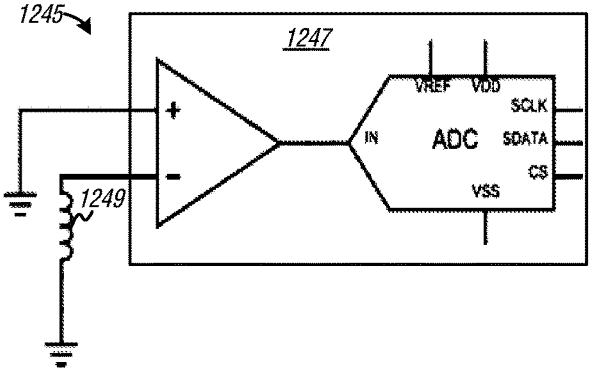
Figure 12E:
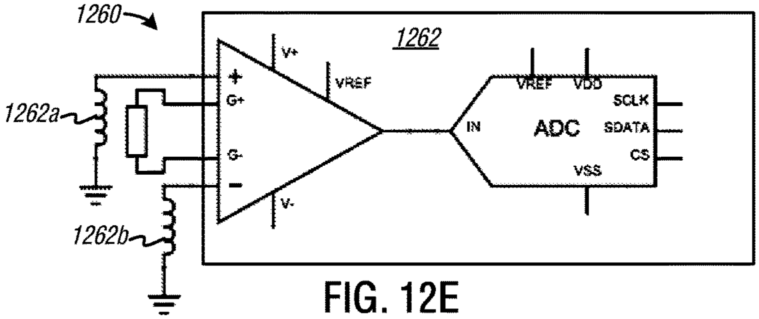
Figure 12F:
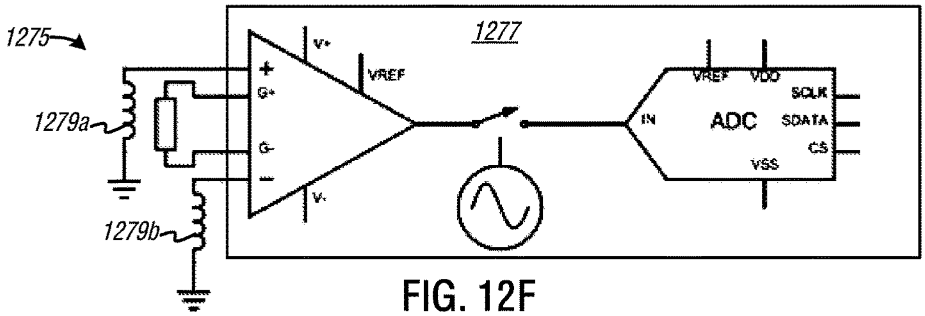

FIG. 12D is a diagram 1245 depicting another example of a neuronal activity detector, according to some examples. As shown, neuronal activity detector 1247 may include an amplifier coupled between an analog-to-digital ("ADC") converter and a coil 1249. FIG. 12E is a diagram 1260 depicting an example of a neuronal activity detector, according to some examples. Neuronal activity detector 1262 of diagram 1260 may include an amplifier coupled between an analog-to-digital ("ADC") converter and coils 1262*a* and 1262*b*. In this example, the amplifier is configured as an instrumentation amplifier. FIG. 12F is a diagram 1277 depicting an example of a neuronal activity detector, according to some examples. As shown, neuronal activity detector 1277 may include an amplifier coupled between an analog-to-digital ("ADC") converter and coils 1279*a* and 1279*b*. The amplifier of diagram 1277 is also configured as an instrumentation amplifier, however, the amplified output may be modulated prior to input into the analog-to-digital ("ADC") converter.

According to various embodiments, an induced magnetic field detected at magnetic sensing elements may be proportional to the frequency of driving signal (e.g., a stimulus signal). Thus, the sensitivity of a neuronal sensing system can be improved by increasing the drive frequency. Hence, the neuronal activity detectors described here need not be limited (as is magnetoencephalography using SQUIDs) to sensing the naturally-occurring, intrinsic magnetic field frequencies (e.g., 1 to 100 Hz or so) originating in the central nervous system. In another example, multiple sensors may be used, the multiple sensors being arranged around a head. Sensors disposed at different positions may receive different net magnetic fields depending on the influences by regions of the central nervous system that are closer to a specific sensor. Therefore, multiple sensors may be used to provide spatially-differentiated sensing of central nervous system activity, including brain activity.

According to various embodiments, a frequency (or range of frequencies) of a driving signal (e.g., a stimulus signal) may be different for each of a number of subsets of stimulus signal elements, which may include, for example, electrodes, magnetic drive coils, light emitting devices, etc. Hence, each response signal element may receive a response signal at a number of different frequencies, each specific frequency or frequency range corresponding to a net magnetic field induced at that a response signal element by the subsets of stimulus signal elements using that specific frequency. Therefore, an induced magnetic fields may be "weighted" according to the relative placements of one or more response signal elements relative to a subset of stimulus signal elements based on the particular frequency. Hence, an individual response signal element may form multiple different "views" of neuronal activity simultaneously (or nearly simultaneously). Each of the different views may correspond to a specific frequency of a number of different frequencies. For each frequency corresponding to a subset of stimulus signal elements, the magnetically-induced signals having the same frequency may be received by a number of different response signal elements. As such, the magnetically-induced signals generating induced currents may be combined in various combinations to provide additional spatial resolution about the distributions of neuronal activity.

Figure 13:
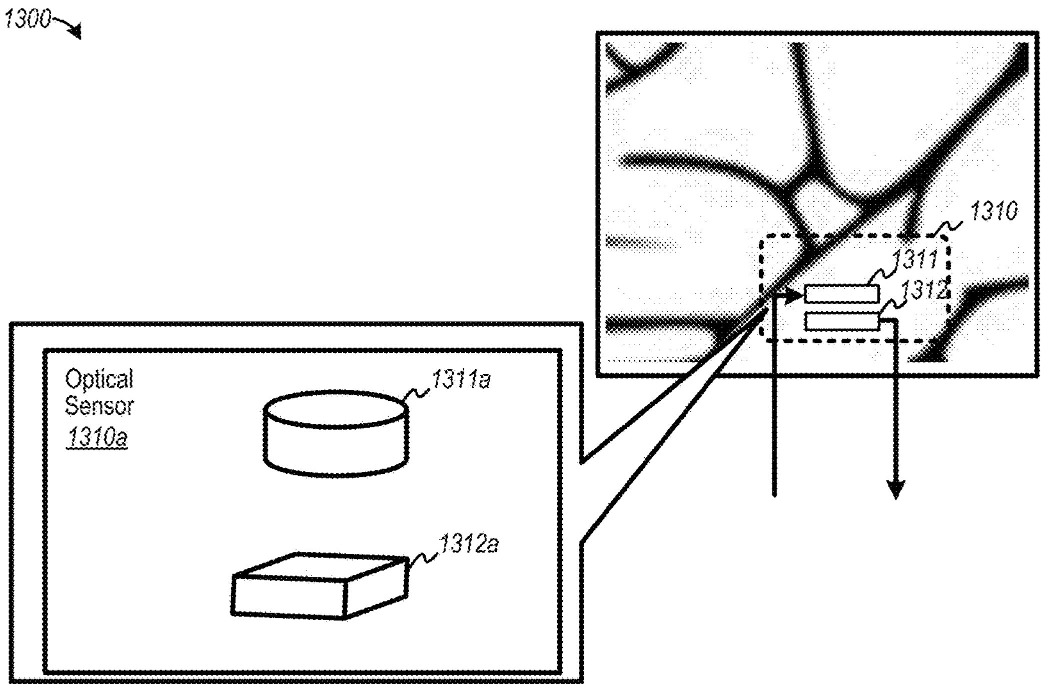
FIG. 13 is a diagram depicting another example of a different type of neuronal activity sensor in accordance with some embodiments.

FIG. 13 is a diagram depicting another example of a different type of neuronal activity sensor in accordance with some embodiments. Diagram 1300 depicts a neuronal activity sensor 1310 including a stimulus signal element 1311 and a response signal element 1312. Stimulus signal element 1311 may be configured to propagate stimulus signals into a target region that includes biological tissues. Response signal element 1312 may be configured to transmit response signals from the biological tissues, whereby the response signal includes data representing a physiological activity characteristic that may describe, for example, a neuronal activity characteristic. According to some embodiments, neuronal activity sensor 1310 may be referred to as a an "optical" sensor that may be configured to sense modified light fields that include data indicative of neural activity (or any physiological activity, such as blood flow, glucose uptake, etc.), for example, associated with activity sensor 1310. As shown, optical sensor 1310*a* may include one or more light emitting sources 1311*a* as stimulus signal element 1311, and may further include one or more light-detecting devices 1312*a*. Optical sensor 1310*a* may be implemented to detect neuronal activity (e.g., using blood flow, or a characteristic thereof, as a proxy whereby blood-related characteristics may be detectable by optical sensor 1310*a*). In other cases, optical sensor 1310*a* may be implemented to detect physiological activity generally (e.g., either neuronal or non-neuronal activities) to correlate with brain activity or any other physiological activity.

Figure 14:
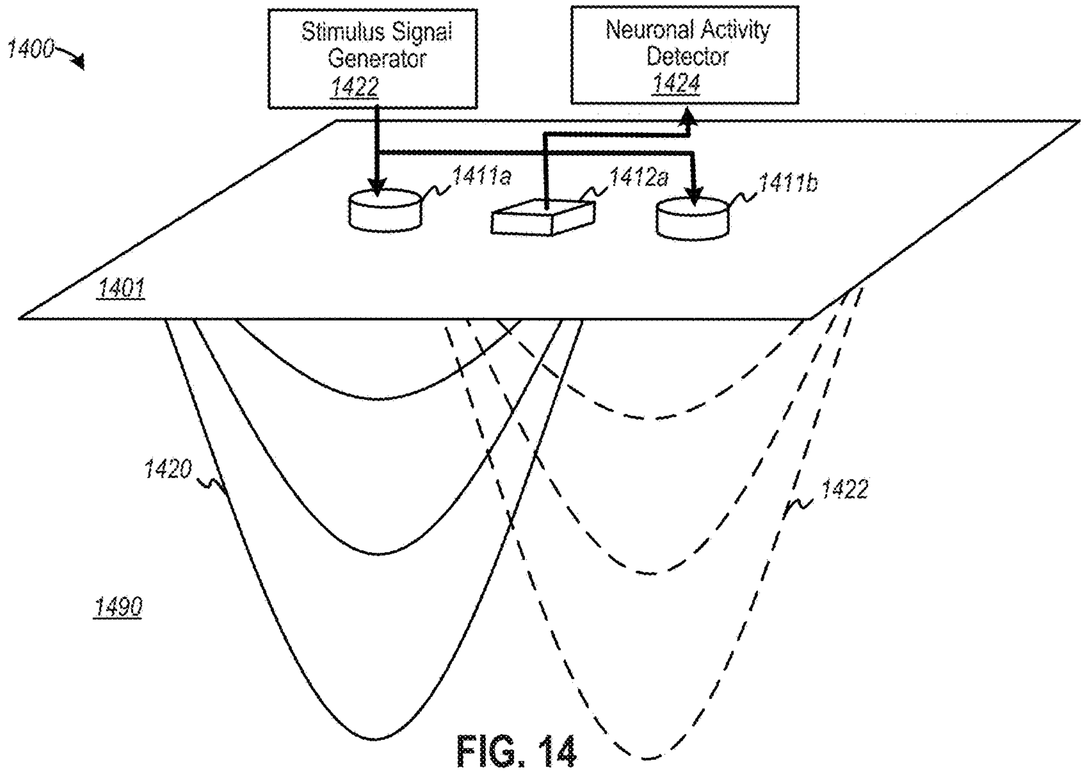
FIG. 14 is a diagram depicting an example of an optical-based neuronal activity sensor in accordance with some embodiments.

FIG. 14 is a diagram depicting an example of an optical-based neuronal activity sensor in accordance with some embodiments. Diagram 1400 depicts a neuronal activity sensor including light emitting diodes ("LEDs") as stimulus signal elements 1411*a* and 1411*b* and a photodiode device as response signal element 1412*a*, which is configured to detect light emanating through biological tissue. Stimulus signal elements 1411*a* and 1411*b* and response signal element 1412*a* are shown to be disposed at or near surface 1401 of skin. Further, stimulus signal generator 1422 may be configured to cause light sources 1411*a* and 1411*b* to inject light field 1420 and light field 1422, respectively, into tissue 1490. Stimulus signal generator 1422 may be configured to cause light field 1420 and light field 1422 to generate light a specific ranges of wavelengths (or frequencies) as well as specific ranges of intensity, whereby certain subcranial or subcutaneous biological structures may be detectable using certain wavelengths of light and/or certain intensities of light. Further to FIG. 14, neuronal activity detector 1424 is coupled to photodiode device 1412*a* to receive a response signal based on detected light that has been modified by the characteristics of the biological tissue through which the light passed. Hence, a modified light field signal may be indicative of an amount of neuronal activity or physiological activity associated with the biological tissue.

Figure 15:
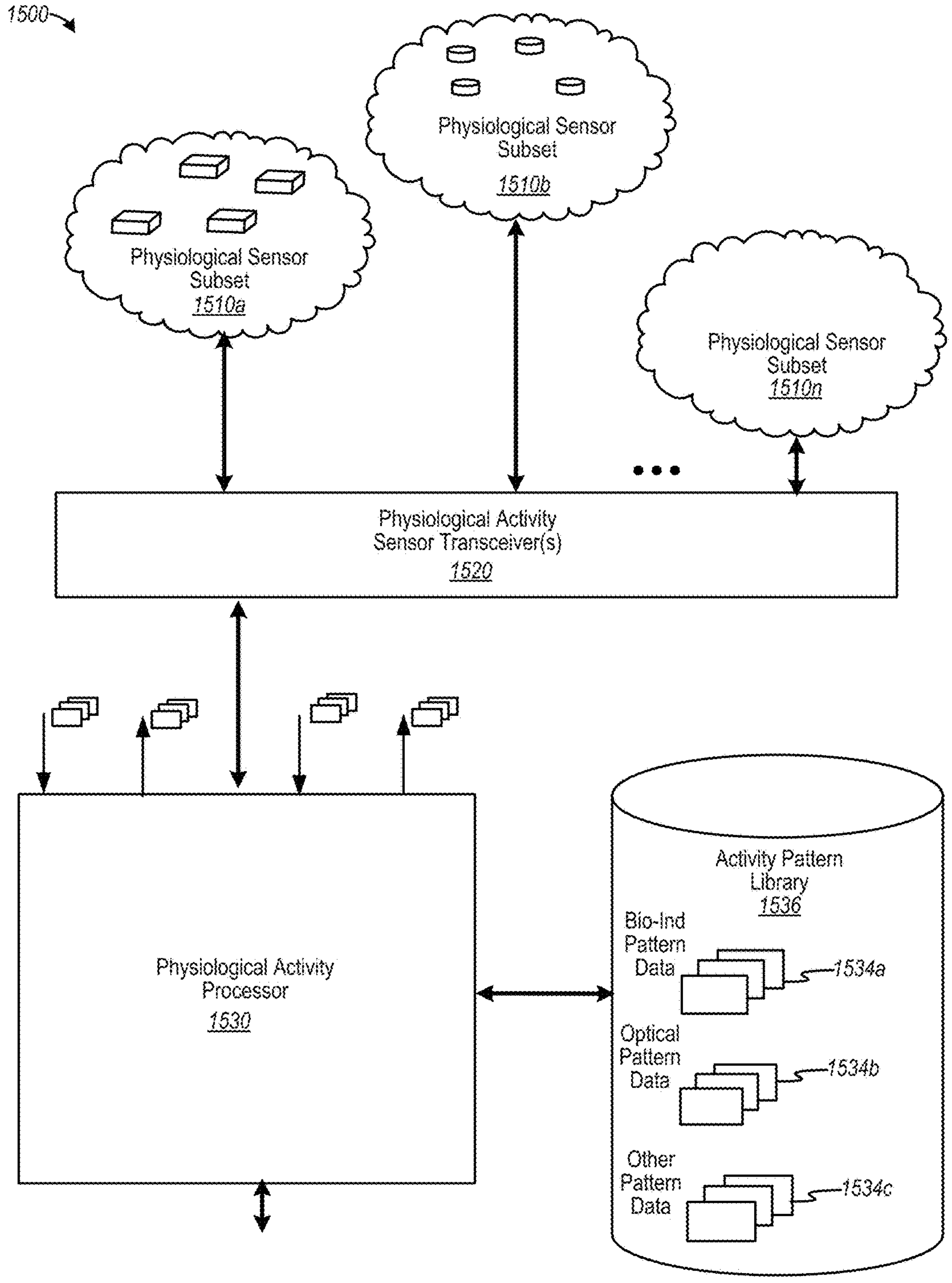
FIG. 15 is a diagram depicting at least one example of a physiological activity sensor system configured to detect neuronal activity as well as other physiological activities, according to various examples.

FIG. 15 is a diagram depicting at least one example of a physiological activity sensor system configured to detect neuronal activity as well as other physiological activities, according to various examples. Diagram 1500 includes any number of physiological sensors subsets 1510*a* to 1510*n* that include any type of different neuronal activity sensors and/or non-neuronal physiological sensors (e.g., that may be used to correlate to neuronal activity). Examples physiological sensors subsets 1510*a* to 1510*n* include, but are not limited to, "bio-inductance" sensors, as described herein, "optical" activity sensors, and other suitable sensors (e.g., acoustic sensors) that may be used to correlate, confirm, or predict that one or more patterns of neuronal activities may identify an "intent" or a "command." According to various embodiments, any one or more of sensors subsets 1510*a*, 1510*b*, and 1510*n* may be used either individually or in combination (as a proxy or to confirm other sensor data).

Physiological activity sensor transceivers 1520 include any number of transceivers to exchange certain stimulus and response signals for particular types of sensors 1510*a* to 1510*n*. Physiological activity processor 1530 may be configured to receive patterns of subsets of response signals, whereby physiological activity processor 1530 and its constituent components may match the patterns against data patterns stored in activity pattern library repository 1526 to identify an associated or linked "intent" or "command." As shown, activity pattern library repository 1536 includes data 1534*a* representing bio-inductance pattern data to match against bio-inductance response signal data, data 1534*b* representing optical pattern data to match against light field response signal data, and data 1534*c* representing other pattern data to match against any other type of response signal data. Subsequent to identifying "intent" or "command," physiological activity processor 1530 may transmit that data to an application controller (not shown) to provide, for example, a human-machine interface for a particular application or software program.

Figure 16:
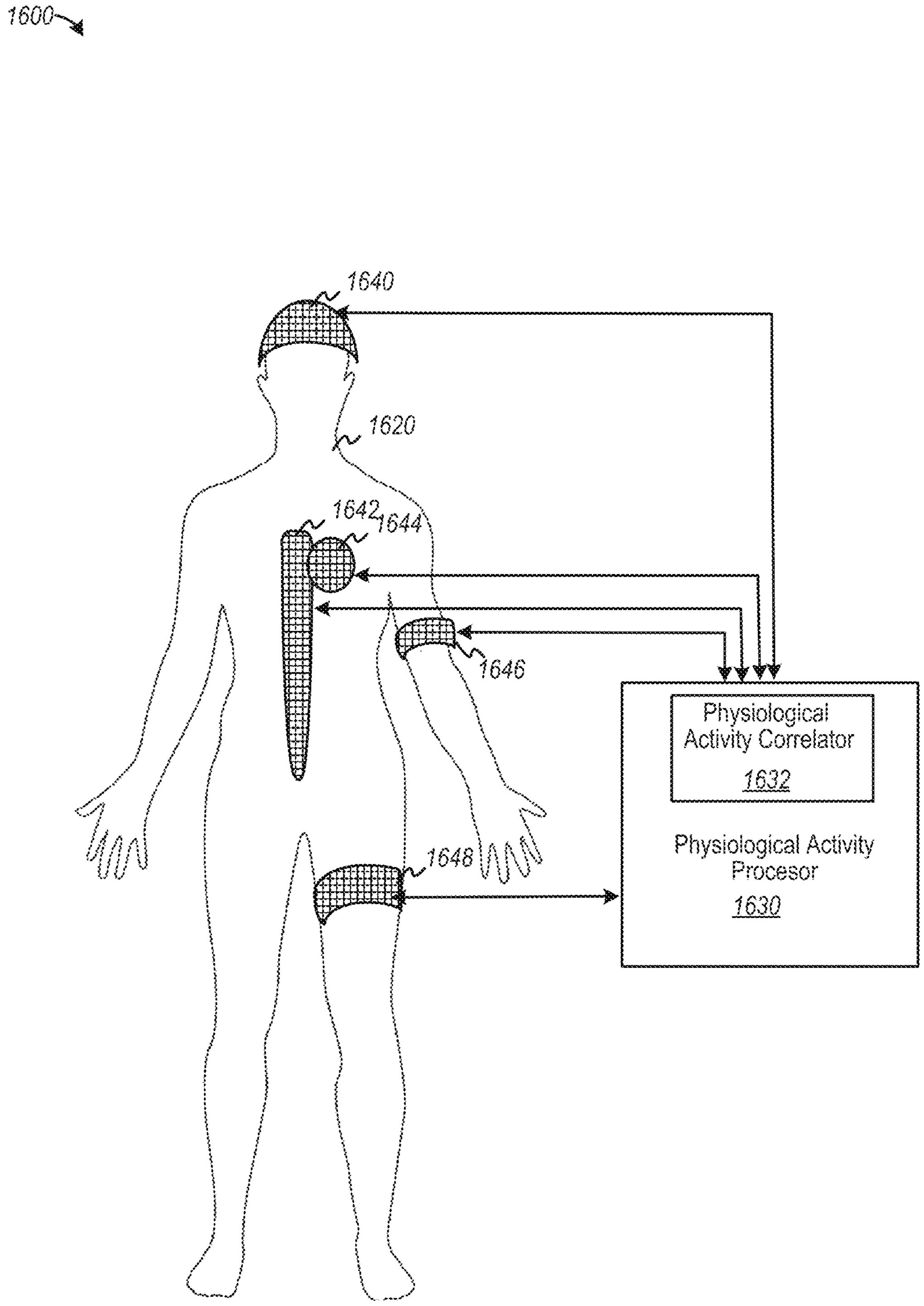
FIG. 16 is a diagram depicting a number of neuronal activity sensor arrangements disposed at various portions of an organism to detect and provide feedback relating to neuronal activity, according to some examples.

FIG. 16 is a diagram depicting a number of neuronal activity sensor arrangements disposed at various portions of an organism to detect and provide feedback relating to neuronal activity, according to some examples. Diagram 1600 depicts an organism 1620 associated with a number of neuronal activity sensor arrangements 1640 (e.g., at or near a brain), 1642 (e.g., at or near a spinal cord), 1644 (e.g., at or near neuronal-related portions of a heart), 1646 (e.g., at or near biological tissue including nerves in a forearm), and 1648 (e.g., at or near biological tissue including nerves in a leg). Any of the sensors described herein, as well as other sensor types, may be implemented in the above-described arrangements of diagram 1600. Physiological activity processor 1630 includes physiological activity correlator 1632, which is configured to correlate neuronal activity at the brain with other sites at which neuronal activity may be detected, such as at an arm. As an example, physiological activity correlator 1632 may determine that neuronal activity and a portion of the brain matches a pattern that includes a "command" to raise an arm. Thus, physiological activity correlator 1632 may receive data representing neural activity at the forearm to determine whether that specific arm is associated with corresponding neuronal activity indicative of a motor command to move the arm. If match between a pattern of response signals from sensor arrangements 1646 matches data representing neuronal activity associated with "raising an arm," then physiological activity processor 1630 may correlate, for example, the instances of action potentials in the brain with those in an upper arm. Note that the example shown in FIG. 16 is merely an example and is not intended to be limiting, and any type of sensor arrangement be disposed on any portion of user 1620 to determine, correlate, confirm, or predict neuronal activity at, for example, a portion of a brain.

Figure 17:
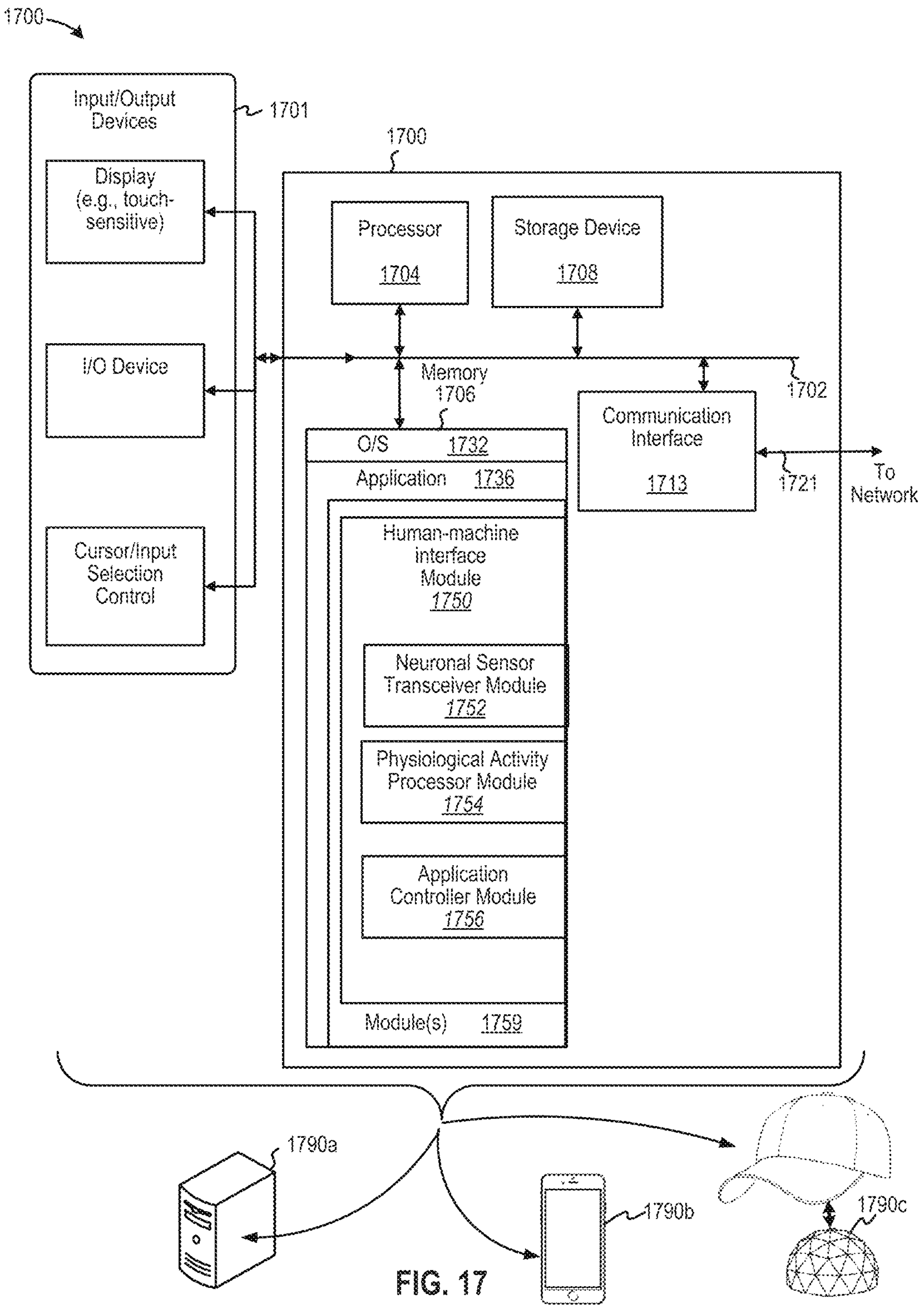
FIG. 17 illustrates examples of various computing platforms configured to provide various functionalities to components of a human-machine interface, according to various embodiments.

FIG. 17 illustrates examples of various computing platforms configured to provide various functionalities to components of a human-machine interface, according to various embodiments. In some examples, computing platform 1700 may be used to implement computer programs, applications, methods, processes, algorithms, or other software to perform the above-described techniques.

In some cases, computing platform 1700 or any portion (e.g., any structural or functional portion) can be disposed in any device, such as a computing device 1790*a*, mobile computing device 1790*b*, and/or a processing circuit disposed in association with a wearable neuronal sensor array 1790*c*.

Computing platform 1700 includes a bus 1702 or other communication mechanism for communicating information, which interconnects subsystems and devices, such as processor 1704, system memory 1706 (e.g., RAM, etc.), storage device 1708 (e.g., ROM, etc.), an in-memory cache (which may be implemented in RAM 1706 or other portions of computing platform 1700), a communication interface 1713 (e.g., an Ethernet or wireless controller, a Bluetooth controller, NFC logic, etc.) to facilitate communications via a port on communication link 1721 to communicate, for example, with a computing device, including mobile computing and/or communication devices with processors. Processor 1704 can be implemented with one or more graphics processing units ("GPUs"), with one or more central processing units ("CPUs"), such as those manufactured by Intel® Corporation, or one or more virtual processors, as well as any combination of CPUs and virtual processors. Computing platform 1700 exchanges data representing inputs and outputs via input-and-output devices 1701, including, but not limited to, keyboards, mice, audio inputs (e.g., speech-to-text devices), user interfaces, displays, monitors, cursors, touch-sensitive displays, LCD or LED displays, and other I/O-related devices.

Note that in some examples, input-and-output devices 1701 may be implemented as, or otherwise substituted with, a human-machine interface in accordance with the various examples described herein.

According to some examples, computing platform 1700 performs specific operations by processor 1704 executing one or more sequences of one or more instructions stored in system memory 1706, and computing platform 1700 can be implemented in a client-server arrangement, peer-to-peer arrangement, or as any mobile computing device, including smart phones and the like. Such instructions or data may be read into system memory 1706 from another computer readable medium, such as storage device 1708. In some examples, hard-wired circuitry may be used in place of or in combination with software instructions for implementation. Instructions may be embedded in software or firmware. The term "computer readable medium" refers to any tangible medium that participates in providing instructions to processor 1704 for execution. Such a medium may take many forms, including but not limited to, non-volatile media and volatile media. Non-volatile media includes, for example, optical or magnetic disks and the like. Volatile media includes dynamic memory, such as system memory 1706.

Common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer can read. Instructions may further be transmitted or received using a transmission medium. The term "transmission medium" may include any tangible or intangible medium that is capable of storing, encoding or carrying instructions for execution by the machine, and includes digital or analog communications signals or other intangible medium to facilitate communication of such instructions. Transmission media includes coaxial cables, copper wire, and fiber optics, including wires that comprise bus 1702 for transmitting a computer data signal.

In some examples, execution of the sequences of instructions may be performed by computing platform 1700. According to some examples, computing platform 1700 can be coupled by communication link 1721 (e.g., a wired network, such as LAN, PSTN, or any wireless network, including WiFi of various standards and protocols, Bluetooth®, NFC, Zig-Bee, etc.) to any other processor to perform the sequence of instructions in coordination with (or asynchronous to) one another. Computing platform 1700 may transmit and receive messages, data, and instructions, including program code (e.g., application code) through communication link 1721 and communication interface 1713. Received program code may be executed by processor 1704 as it is received, and/or stored in memory 1706 or other non-volatile storage for later execution.

In the example shown, system memory 1706 can include various modules that include executable instructions to implement functionalities described herein. System memory 1706 may include an operating system ("O/S") 1732, as well as an application 1736 and/or logic module(s) 1759. In the example shown in FIG. 17, system memory 1706 includes what human-machine interface module 1750 and/or its components (e.g., a neuronal sensor transceiver module 1752, a physiological activity processor module 1754, an application controller module 1756, etc.), any of which, or one or more portions of which, can be configured to facilitate a human-machine interface by implementing one or more functions described herein.

The structures and/or functions of any of the above-described features can be implemented in software, hardware, firmware, circuitry, or a combination thereof. Note that the structures and constituent elements above, as well as their functionality, may be aggregated with one or more other structures or elements. Alternatively, the elements and their functionality may be subdivided into constituent sub-elements, if any. As software, the above-described techniques may be implemented using various types of programming or formatting languages, frameworks, syntax, applications, protocols, objects, or techniques. As hardware and/or firmware, the above-described techniques may be implemented using various types of programming or integrated circuit design languages, including hardware description languages, such as any register transfer language ("RTL") configured to design field-programmable gate arrays ("FPGAs"), application-specific integrated circuits ("ASICs"), or any other type of integrated circuit. According to some embodiments, the term "module" can refer, for example, to an algorithm or a portion thereof, and/or logic implemented in either hardware circuitry or software, or a combination thereof. These can be varied and are not limited to the examples or descriptions provided.

In some embodiments, module 1750 of FIG. 17, or one or more of their components, or any process or device described herein, can be in communication (e.g., wired or wirelessly) with a mobile device, such as a mobile phone or computing device, or can be disposed therein.

In some cases, a mobile device, or any networked computing device (not shown) in communication with one or more modules 1759 (module 1750 of FIG. 17) or one or more of its components (or any process or device described herein), can provide at least some of the structures and/or functions of any of the features described herein. As depicted in the above-described figures, the structures and/or functions of any of the above-described features can be implemented in software, hardware, firmware, circuitry, or any combination thereof. Note that the structures and constituent elements above, as well as their functionality, may be aggregated or combined with one or more other structures or elements. Alternatively, the elements and their functionality may be subdivided into constituent sub-elements, if any. As software, at least some of the above-described techniques may be implemented using various types of programming or formatting languages, frameworks, syntax, applications, protocols, objects, or techniques. For example, at least one of the elements depicted in any of the figures can represent one or more algorithms. Or, at least one of the elements can represent a portion of logic including a portion of hardware configured to provide constituent structures and/or functionalities.

For example, module 1750 of FIG. 17 or one or more of its components, or any process or device described herein, can be implemented in one or more computing devices (i.e., any mobile computing device, such as a wearable device, such as a hat or headband, or mobile phone, whether worn or carried) that include one or more processors configured to execute one or more algorithms in memory. Thus, at least some of the elements in the above-described figures can represent one or more algorithms. Or, at least one of the elements can represent a portion of logic including a portion of hardware configured to provide constituent structures and/or functionalities. These can be varied and are not limited to the examples or descriptions provided.

As hardware and/or firmware, the above-described structures and techniques can be implemented using various types of programming or integrated circuit design languages, including hardware description languages, such as any register transfer language ("RTL") configured to design field-programmable gate arrays ("FPGAs"), application-specific integrated circuits ("ASICs"), multi-chip modules, or any other type of integrated circuit.

For example, module 1750 of FIG. 17, or one or more of its components, or any process or device described herein, can be implemented in one or more computing devices that include one or more circuits. Thus, at least one of the elements in the above-described figures can represent one or more components of hardware. Or, at least one of the elements can represent a portion of logic including a portion of a circuit configured to provide constituent structures and/or functionalities.

Figure 18:
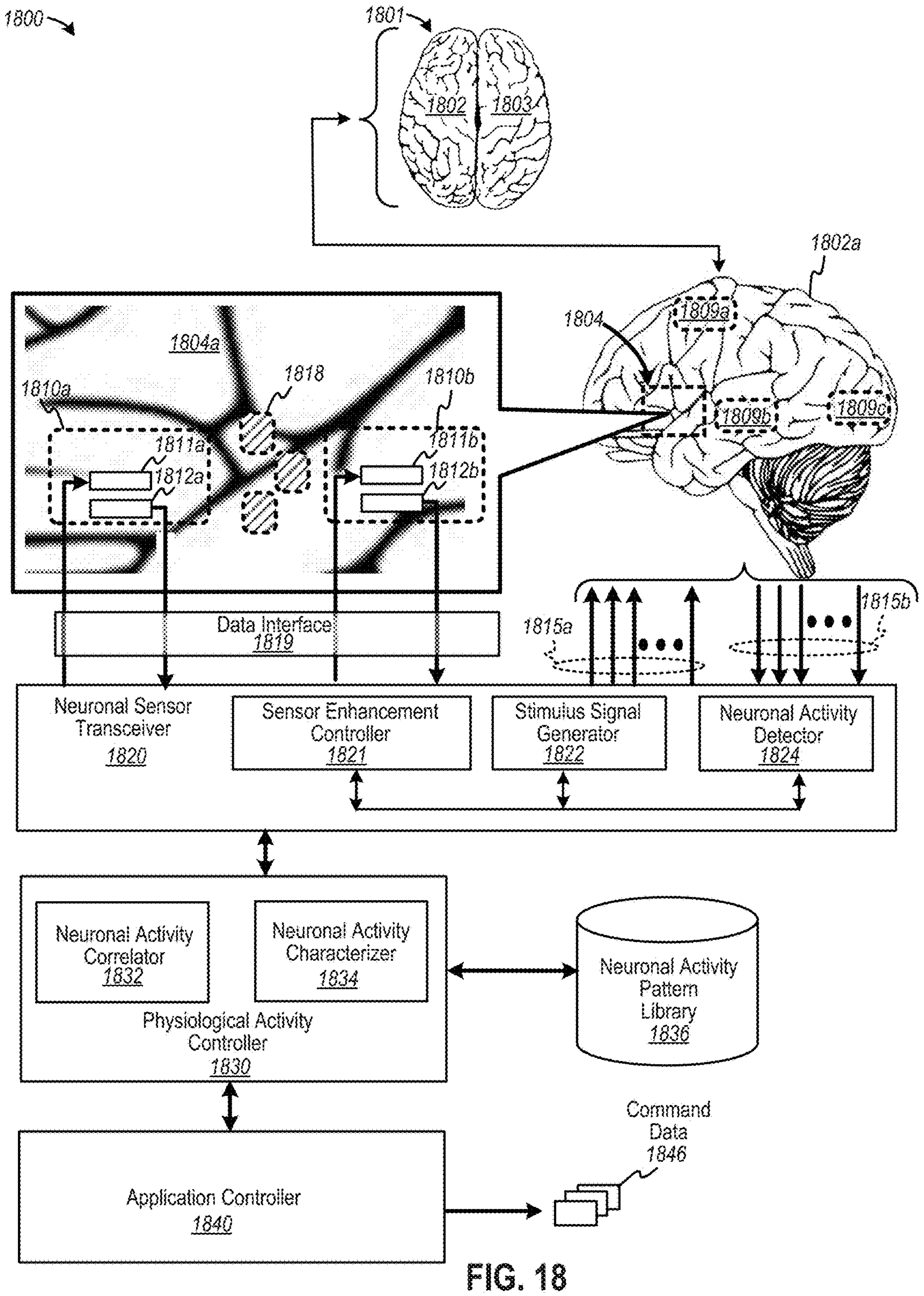
FIG. 18 is a diagram depicting a neuronal activity sensing system to facilitate a human-machine interface, according to some embodiments.

FIG. 18 is a diagram depicting a neuronal activity sensing system to facilitate a human-machine interface, according to some embodiments. Diagram 1800 depicts a brain 1801 of an organism (e.g., a human user), brain 1801 including a left cerebral hemisphere 1802 and a right cerebral hemisphere 1803, from which neuronal activity of a central nervous system may be sensed to determine a neuronal state. According to various examples, a human-machine interface may include one or more arrays (not shown) of one or more subsets 1810*a* and 1810*b* of physiological activity sensors, which are shown to be configured to sense a portion of activity (e.g., neuronal activity) in region 104*a* of left cerebral hemisphere 1802*a*.

FIG. 18 also depicts a neuronal sensor transceiver 1820 configured to control operations of subsets 1810*a* and 1810*b* of physiological activity sensors. Neuronal sensor transceiver 1820 may be configured to implement a sensor enhancement controller 1821 to enhance the sensed data originating from subsets 1810*a* and 1810*b* of physiological activity sensors to enhance resolution of the neuronal sensing system. For example, sensor enhancement controller 1821 may be configured to modulate the characteristics of physiological activity sensors 1810*a* or 1810*b*, including response signal elements 1812*a* and 1812*b*, to derive an increased amount (e.g., a multiplicative amount) of induced current signal as "derived induced current signals." Therefore, sensor enhancement controller 1821 may provide enhanced sensing capabilities as "virtual sensors" that may provide the derived induced current signals. In some examples, sensor enhancement controller 1821 may be configured to modulate or vary an induced current density or induced magnetic field so as to detect corresponding changes, which may enhance the resolution of the neuronal sensing system greater than a resolution provided by a number of physiological activity sensors 1810*a* and 1810*b* disposed in an array that, for instance, is disposed over one or more portions of brain 1801. In the examples in which subsets 1810*a* and 1810*b* are electrodes, consider that sensor enhancement controller 1821 may be configured to vary induced currents so as to perturb an arrangement of currents, which may generate moving regions of higher or lower current densities (e.g., gradients of current densities). Further, by correlating the detected magnetic field(s) induced by such current densities with the perturbation(s), neuronal sensor transceiver 1820 may increase the effective resolution of a neuronal sensing system, as described herein.

Examples of physiological activity sensors are depicted as subset 1810*a* of physiological activity sensors and subset 1810*b* of physiological activity sensors. A physiological activity sensor may include any sensor configured to detect neuronal activity or non-neuronal activity, or both. Thus, either subset 1810*a* or subset 1810*b* of physiological activity sensors, or both, may be implemented as neuronal activity sensors configured to, among other things, detect activity (and magnitudes thereof) of a central nervous system. Further, a neuronal activity sensor may also be configured to sense non-neuronal activity that, for example, provides information regarding neuronal activity. Such a neuronal activity sensor may sense non-neuronal activity, such as oxygenation levels of blood, glucose levels, etc., as proxies for one or more characteristics of the activities of a central nervous system. The term "physiological activity sensor" may be used interchangeably with the term "neuronal activity sensor," according to at least some example implementations. Note further, at least one of subset 1810*a* and subset 1810*b* of physiological activity sensors may be implemented (e.g., as contextual activity sensors) to sense non-neuronal activity to provide a context in which neuronal activity may be sensed. For example subset 1810*a* may be configured to detect orientation and/or placement of physiological features such as skull, scalp, gyri and/or sulci and subset 1810*b* may be configured to detect brain activity that may be localized in conjunction with signals from subset 1810*a*. For example, subset 1810*a* may be configured to detect brain activity relating to motor coordination and subset 1810*b* may include motion sensors (e.g., accelerometers disposed on a leg) that may be configured to detect movement correlated with the brain activity relating to motor coordination (e.g., an intent to pick up the user's foot). According to various examples, one of subset 1810*a* and subset 1810*b* of physiological activity sensors need be implemented. Or, any number or type of physiological activity sensor may be implemented in associated with the human-machine interface or any component thereof.

Neuronal sensor transceiver 1820 may be coupled to the arrays of physiological activity sensors 1810*a* and 1810*b* to apply stimuli to one or more portions of brain 1801 at configurable degrees of resolution, such as portions 1804, 1809*a*, 1809*b*, and 1809*c*. Further, the array of physiological activity sensors 1810*a* may be configured to receive responses from the one or more portions of brain 1801, whereby the responses may include characteristics of neuronal activity with which a type of neuronal activity and/or a neuronal state may be associated. Examples of neuronal activity types include, but are not limited to, visual activities, auditory activities, tactile sensations, coordinated motor control impulses, memory activities, speech-related activities, emotions, among others, whereby at least some of the aforementioned types may be determined through localized portions of brain 1801. A neuronal state may refer, at least in some examples, to a set of one or more patterns of a central nervous system (e.g., spatial and/or temporal patterns of action potentials) that may be associated with a detectable thought, idea, intent (e.g., command), or the like. In some cases, a neuronal state may be identified as a function of the one or more patterns of brain activity (e.g., spatially-related patterns or temporally-related patterns, or both). As an example, consider that neuronal sensor transceiver 1820 may be configured to spatially and/or temporally control the application of stimulus signals and response signals in association with brain portions 1809*a*, 1809*b*, and 1809*c*. Examples of brain portions 1809*a*, 1809*b*, and 1809*c* include a portion of a motor cortex, a portion of an auditory cortex, and a portion of a visual cortex, respectively. Hence, these portions of the brain, which are spatially disposed at different locations, may be sensed temporally (e.g., simultaneously or sequentially) to detect and or correlate neuronal activity associated with, for example, a user's intent to look and speak, as well as move a muscle (e.g., to point a finger). In some cases, neuronal activity sensors 1810*a* or 1810*b* may be referred to as a central nervous system ("CNS") sensor.

In accordance with some examples, physiological activity sensors 1810*a* and 1810*b* and neuronal sensor transceiver 1820 may be configured to detect neuronal activity indirectly from biological tissues that include blood vessels and other non-neuronal tissue as, for example, a proxy for neural activity. As different physiological materials may have different impedance frequency responses, the conductivity of such physiological materials may respond differently to different ranges of drive frequencies responsive to, for example, the electromagnetic characteristics of non-neuronal physiological material, such as oxygenated blood, deoxygenated blood, glucose, etc. Therefore, a set of one or more drive frequencies of electric or magnetic fields can be selected to identify activities related to the different physiological materials. In some embodiments, multiple drive frequencies may be provided simultaneously or in sequence to track these different physiological materials simultaneously (or substantially simultaneously). In some examples, the various different frequencies may be injected into biological tissue using one or more sets of electrodes or using magnetic drive coils. Hence, blood flow, glucose uptake, and other (e.g., non-neuronal) physiological activities may be used a proxy to indirectly detect or predict neural activity. Furthermore, neuronal activity sensors 1810*a* and neuronal sensor transceiver 1820 may be configured to detect and characterize neuronal activity based on induced magnetic fields originating from and/or modified by activity associated with both neuronal tissue (e.g., cerebrospinal fluid, neurons, axons, dendrites, etc.) and non-neuronal tissue (e.g., blood vessels, blood, glucose levels, etc.).

In some embodiments, subset 1810*a* of activity sensors may include a stimulus signal element 1811*a* and a response signal element 1812*a*. Similarly, subset 1810*b* of activity sensors may include a stimulus signal element 1811*b* and a response signal element 1812*b*. Stimulus signal elements 1811*a* and 1811*b* each may be configured to propagate one of stimulus signals 1815*a* into the target region that includes biological tissues or components. Response signal elements 1812*a* and 1812*b* may be configured to transmit at least one of response signals 1815*b*, whereby a response signal may include data representing a physiological activity characteristic that may describe, for example, a neuronal activity characteristic. According to some embodiments, one of activity sensors 1810*a* and 1810*b* may be a "bio-inductance" sensor that is configured to sense induced magnetic fields that include data indicative of neural activity. In some examples, a magnetic carrier signal or field may originate or emanate from currents in biological tissues including but not limited to induced currents, synaptic currents, cerebrospinal fluid eddy currents, and other current sources in a central nervous system that may be modified (e.g., modulated) by the changing localized conductivity of, for example, cerebrospinal fluid due to neural activity, including, but not limited to, one or more action potentials (e.g., via transportation of potassium and sodium ions), any of which may be isolated or aggregated for purposes of quantifying an amount of neuronal activity, according to various examples.

In a specific example, one or more of stimulus signal elements 1811*a* and 1811*b* may include one or more electrodes to apply an electric current density (e.g., an electric field) as a stimulus signal field into biological tissue. The electric current density is injected into biological tissues via one or more electrodes, and may be further configured to form an induced magnetic field. According to some examples, an alternating current or voltage signal is applied as a stimulus signal to one of stimulus signal elements 1811*a* and 1811*b* to generate alternating induced magnetic fields of various frequencies (e.g., ranging from a few Hz to a few hundred MHz, or any suitable other range, such as 100 kHz to 5 MHz or the like). Response signal elements 1812*a* and 1812*b* of FIG. 18 may include one or more magnetic sensing elements. Further to the above example, response signal elements 1812*a* and 1812*b* may include, but are not limited to, one or more coils (e.g., one or more search coils) configured to receive one or more alternating magnetic fields with magnetic portions attributable to neural current.

In other examples, one or more of stimulus signal elements 1811*a* and 1811*b* may include one or more magnetic drive coils to receive an electric current density and propagate a magnetic field, as a stimulus signal field, into biological tissue. The magnetic field (e.g., as an induced magnetic field) is propagated into biological tissues via one or more magnetic drive coils. Similarly, at least in some cases, an alternating current or voltage signal may be applied as a stimulus signal to one of stimulus signal elements 1811*a* and 1811*b* that is formed as magnetic drive coils to generate alternating induced magnetic fields of various frequencies (e.g., ranging from a few Hz to a few hundred MHz, or any suitable other range, such as 100 kHz to 5 MHz or the like). Response signal elements 1812*a* and 1812*b*, as magnetic sensing elements (e.g., coils) are configured to receive the induced fields from the magnetic drive coil.

In yet another example, one or more of stimulus signal elements 1811*a* and 1811*b* may include one or more photonic drivers to receive a stimulus signal for purposes of propagating a light field, as a stimulus signal field, into biological tissue. An example of a photonic driver includes one or more light emitting diodes ("LEDs"), which may be of the same or different wavelengths, or any other light emitting source. Correspondingly, response signal elements 1812*a* and 1812*b* may include photonic sensing elements, such as one or more light sensing elements. Further to the above example, response signal elements 1812*a* and 1812*b* may include, but are not limited to, one or more photodiodes configurable to receive one or more wavelengths or ranges of wavelengths of light, which may include data attributable to neural current or other physical activities. In at least one example, one of sensors 1810*a* or 1810*b* may an optical sensor that may be used on combination with another type of sensor, such as a neuronal activity sensor.

Diagram 1800 also depicts a neuronal sensor transceiver 1820 that is shown to include a sensor enhancement controller 1821, a stimulus signal generator 1822, and a neuronal activity detector 1824. Sensor enhancement controller 1821 may be configured to form "virtual sensors" 1818 that provide derived induced current signals (or any other derived response signals) to enhance the resolution of the neuronal sensing system greater than, for example, a resolution associated with physiological activity sensors 1810*a* and 1810*b*. Stimulus signal generator 1822 may be configured to selectably drive a stimulus signal 1815*a*, such as an alternating current signal, in association with one or more stimulus signal elements 1811, such as one or more electrodes, magnetic drive coils, light emitting sources, to generate a stimulus field (e.g., an alternating electric or magnetic or optic field having varying magnitudes) in the biological tissues with which neuronal activity may be measured. Neuronal activity detector 1824 may be configured to receive a response signal that includes data representing an amount of neuron activity. According to some examples, response signal 1815*b* received by neuronal activity detector 1824 may be an induced current signal indicative of the modified induced magnetic or optic field received into, for example, a coil, photodiode, or any other sensory circuit or device.

Diagram 1800 further depicts a physiological activity processor 1830 and an application controller 1840 to facilitate a human-machine interface, according to some examples. Physiological activity processor 1830 may be configured to identify instances of neuronal activity that may be used to determine a neuronal state or any other physiological state. According to some embodiments, physiological activity processor 1830 may be configured to access a database repository 1836 including a neuronal activity pattern library to, for example, match responses received from the array of one or more neuronal activity sensors 1810*a*. The matched responses constitute one or more states of neuronal activity that may be aggregated to identify a thought or command, whether at an atomic level (e.g., a unit level) or at a macro-level (e.g., multiple thoughts or commands). Physiological activity processor 1830 may be further configured to transmit data representing one or more thoughts or commands to application processor 1840, which, in turn, may be configured to map one or more thoughts or commands to a function of a particular interface or application, such as a text editor application. Therefore, application processor 1840 can generate command data 1846 suitable for the text editor application. Examples of command data 1846 may include interface commands to navigate an interface (e.g., user interface commands such as up, down, left, right, pan, zoom, etc.). Other examples of command data 1846 may include application-specific commands (e.g., identifying a word and performing an "insert" word operation, a back space command, select text command, text formatting commands, etc.). Another example of an application for which command data 1846 is generated includes a computer tomography application configured to build a 3D model of activity (e.g., neuronal or non-neuronal activities) within the central nervous system. Thus, diagram 1800 depicts examples of various components that may implement a neuronal activity sensing system that facilitates a neuronal-based human-machine interface.

In view of the foregoing, the structures and/or functionalities depicted in FIG. 18 illustrate a human-machine interface (or portions thereof) including a neuronal sensing system and other components that can directly or indirectly (e.g., though proxy physiological activities, which may be non-neural activities) detect and characterize neuronal activity of brain 1801. According to some embodiments, a physiological activity sensor 1810*a* or 1810*b*, any of which may be implemented as a "bio-inductance sensor," may be configured to induce currents in a central nervous system through electrodes, magnetic drive coils, or other suitable sensors disposed on or adjacent to a scalp (or a portion thereof), and further configured to detect corresponding induced magnetic fields by magnetic sensing elements at or outside a surface of scalp or skull. In some examples, a sensing elements may be disposed in a range, for example, up to two centimeters (e.g., up to 2 cm or greater) from a skin surface.

According to some examples, stimulus signal generator 1822 may be configured to generate an alternating current signal, as a stimulus signal 1815*a*, at various frequencies and ranges of frequencies. As such, the greater the alternating frequency of stimulus signal 1815*a*, the greater the magnitude of an induced magnetic field that may be generated. Thus, stimulus signal generator 1822 may generate an AC signal that is driven at specific ranges of high frequencies to induce a relatively stronger response magnetically (i.e., relative to lower frequencies). Accordingly, stimulus signal generator 1822 may be configured to drive stimulus signal at specific frequencies configured to induce certain magnetic responses to detect or measure certain types of biological material through which an induced magnetic field emanates. Stimulus signal generator 1822, therefore, can be configured to provide a stimulus signal from which to derive one or more characteristics of a type of tissue through which an induced magnetic field propagates. Examples of various types of biological material or tissue include, but are not limited to, cerebrospinal fluid, axons, dendrites, white cellular brain matter, grey cellular brain matter, as well as blood, glucose, and other materials that may be used either as a proxy for neural activity (e.g., for indirect measurement of neuronal activity) or a contextual characteristic element with which to compare with other sensor data to confirm neuronal activity or a type of neuronal or physiological activity, as well as amounts thereof.

Further, sensor enhancement controller 1821 may be configured to enhance resolution of the neuronal sensing system by, for example, controlling operation of stimulus signal generator 1822 and neuronal activity detector 1824 to increase (e.g., selectively) a number of sensor measurements associated with each physical sensor to a larger number of virtual sensor measurements. Such "virtual sensors" may provide more data than, for example, a practical limit, if any, to a number of physical sensors that can be coupled to a scalp. In some examples, sensor enhancement controller 1821 may be configured to interpolate sensed data spatially and/or temporally as if one or more physical sensor is located at positions of virtual sensors 1818. Therefore, consider an example in which a number of activity sensors 1810*a* and/or 1810*b* in an array may include about 2,000 physical sensors. Accordingly, sensor enhancement controller 1821 may be configured to facilitate implementation of a number of "virtual sensors" from 4,000 to 5,000, up to 10,000, or greater, thereby increasing a number of sensed response signals (and resolution).

Diagram 1800 also depicts a data interface 1819 of neuronal sensor transceiver 1820 may include hardware or software, or both, that is configured to detect an orientation of physiological activity sensors 1810*a* and 1810*b* relative to a reference point, and may be further configured to automatically self-register the array relative to, for example, one or more internal biological structures under a surface of the skin. Therefore, data interface 1819 as well as arrays or sub-arrays of physiological activity sensors 1810*a* and 1810*b* facilitate implementation of the human-machine interface (or a portion thereof) as a wearable structure, such as a hat, headband, or the like.

According to yet other examples, response signal elements 1812*a* and 1812*b* may include multiple components, such as a first component (e.g., a first coil or photodiode) that may be configured to have a specific sensitivity to surface effects (e.g., scalp or skull currents, or a specific sensitivity to frequency or wavelength) and a second component (e.g., a second coil or photodiode) having another sensitivity to both surface and deeper effects (e.g., currents). As such, neuronal activity detector 1824 may be configured to subtract or otherwise account for one response signal (e.g., induced current at the scalp) relative to other response signal(s) to enhance a sensitivity in measuring of particular neuronal activity (or biological material) of interest at a depth from a skin surface.

Structures and/or functionalities depicted herein set forth a human-machine interface (or portions thereof) that include a neuronal sensing system that can directly or indirectly characterize neuronal activity of brain 1801 or other portions of a body with sufficient neuronal activity (e.g., a group of neurons firing). Consequently, structures and/or functionalities set forth herein may provide central nervous system activity sensing techniques having either enhanced spatial resolution or enhanced temporal resolution, or both. Further, structures and/or functionalities set forth herein may provide for an enhanced dynamic range, as well as an effective direct technique to sense brain activity. Moreover, a human-machine interface according to various examples described herein may provide for a relatively lower cost, lower power, more portable human-machine interface than otherwise may be the case. The human-machine interface also may be able to enhance diagnosis of various disorders, facilitate implementation of enhanced user interfaces, and provide initial insight and analysis of functionality of each human user's central nervous system.

Further to diagram 1800, physiological activity processor 1830 may also include a neuronal activity correlator 1832 and a neuronal activity characterizer 1834, according to some examples. Neuronal activity characterizer 1834 may include hardware or software, or both, and may be configured to characterize instances of neuronal activity such that each instance of neuronal activity may be decomposed into, or otherwise stored as, one or more data patterns that are associated with a specific brain activity. In turn, the data patterns may be stored as data arrangements within neuronal activity pattern library 1836. For example, neuronal activity characterizer 1834 may be configured to learn (e.g., via deep learning or other types of machine learning, as well as empirically) or otherwise associate identified "thoughts" or "intents" originating from brain 1801 with such a pattern. Neuronal activity correlator 1832 may include hardware or software, or both, and may be configured to implement the data patterns of repository 1836 to identify or categorize detected brain activities from neuronal activity detector 1824. Thus, neuronal activity correlator 1832 facilitates in-situ operation of an array of physiological activity sensors 1810*a* to effectuate the corresponding human-machine interface, according to various embodiments.

Application controller 1840 may include hardware or software, or both, and may be configured to generate command data 1846 based on identified neuronal activities, as well as identified non-neuronal activities. Examples of command data 1846 may include instructions (e.g., such as an application programming interface, or API) that invokes a command as a function of detected neuronal or non-neuronal activity. The commands may relate to interface commands, as well as commands or instructions to facilitate communication. In some embodiments, command data 1846 may also include instructions to provide an idea or thought that correlates to a particular type of neuronal activity. Therefore, should an organism be thinking of an automobile having a color "blue," the observation (e.g., a thought or idea) may relate to detectable neuronal characteristics constituting neuronal activity states of "blue" and "automobile." Thus, command data 1846 may specify the command of presenting a "blue automobile" to a user interface (e.g., a graphical user interface, or GUI).

Figure 19:
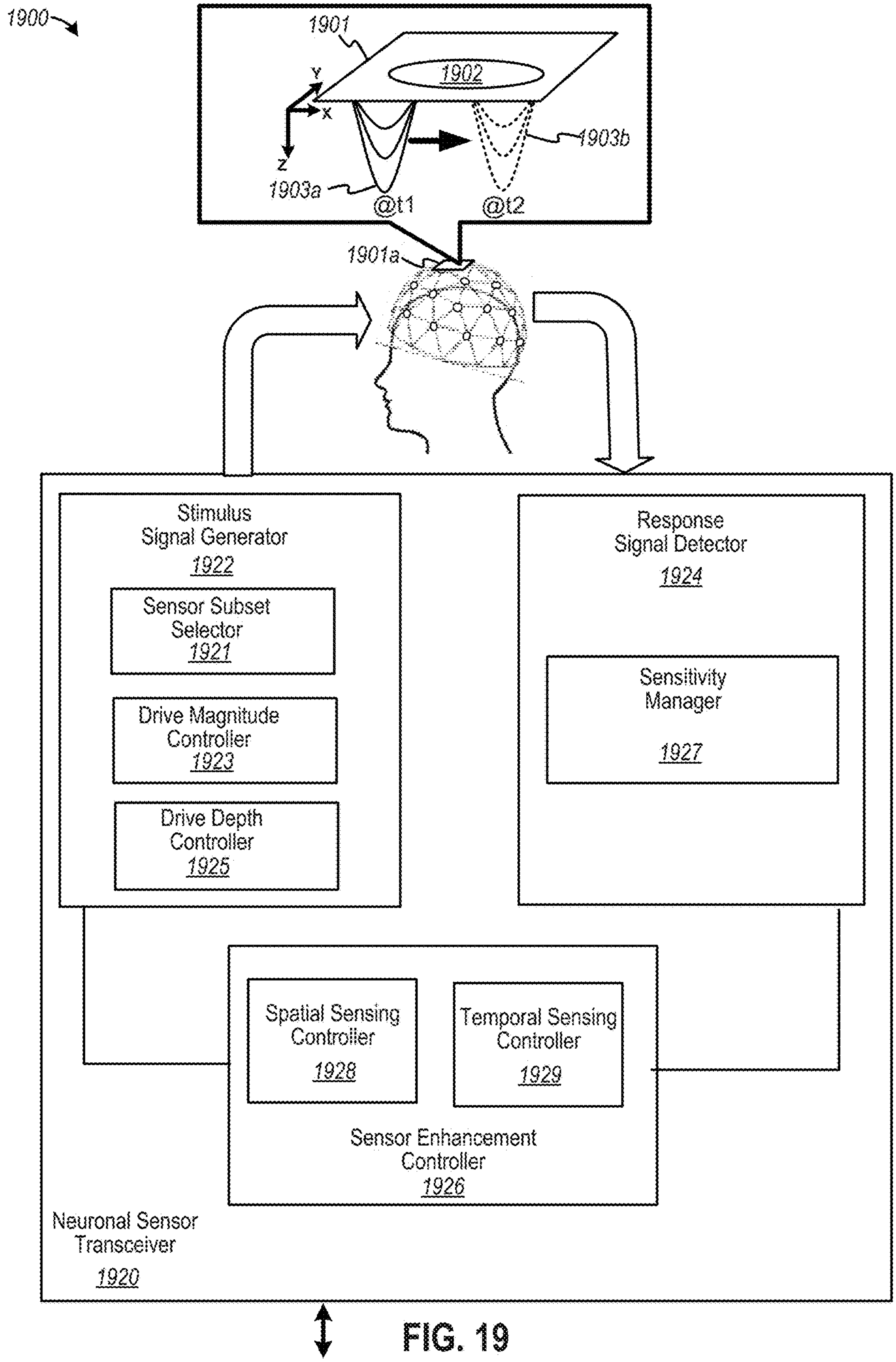
FIG. 19 is a diagram depicting an example of a neuronal sensor transceiver configured to control operation of physiological activity sensors, according to some embodiments.

FIG. 19 is a diagram depicting an example of a neuronal sensor transceiver configured to control operation of physiological activity sensors, according to some embodiments. Diagram 1900 depicts a neuronal activity transceiver 1920 configured to facilitate enhanced sensing capabilities, thereby increasing resolution beyond abilities of physical sensors. Thus, neuronal activity transceiver 1920 facilitates implementation of "virtual sensors" that may provide derived characteristics (e.g., computed or indirect characteristics) of neuronal activity.

In the example shown, neuronal sensor transceiver 1920 includes the stimulus signal generator 1922, a response signal detector 1924, and a sensor enhancement controller 1926. Sensor enhancement controller 1926 may be configured to control stimulus signal generator 1922 or response signal detector 1924 (e.g., a neuronal activity detector) to modulate, vary, or otherwise process stimulus signals or response signals to enhance the resolution of the neuronal sensing system. Stimulus signal generator 1922 includes a sensor subset selector 1921, a drive magnitude controller 1923, and a drive depth controller 1925. Sensor subset selector 1921, responsive to control signals from sensor enhancement controller 1926. Sensor subset selector 1921 configured to select subsets of neuronal activity sensors at, for examples, areas of the brain at which certain neuronal activities of interest generally occur (e.g., visual cortex, etc.). The selection of such subsets of sensors may be simultaneous or sequential, in any combination.

Drive magnitude controller 1923 is configured to control the magnitude or intensity of the stimulus signal drive so to generate variable or unequal distributions of a stimulus field in the head such that, for example, a specific sensor can be configured to be more sensitive to a given region. By modulating a drive current or voltage, or modulating the drive field magnitude distribution, a single sensor can gain resolution because the detection of the response signal can be localized differently based on the drive field. For example, drive magnitude controller 1923 may modify a current magnitude or current density of stimulus signal that drives electrodes to generate a variable or unequal distribution of an electric field in the head. As another example, drive magnitude controller 1923 may modify a current magnitude or current density with which to modify generation of a magnetic field by a magnetic drive element (e.g., magnetic drive coil) to generate a variable or unequal distribution of a magnetic field in the head. In yet another example, drive magnitude controller 1923 may modify operation of a light-emitting source to vary a magnitude or intensity of light to cause a variable or unequal distribution of a light field in the head. According to some embodiments, drive magnitude controller 1923 may be configured to modify the drive signals of any number and types of sensors (e.g., acoustic sensors or any type of sensor suitable to detect neuronal or non-neuronal activity). As shown in diagram 1900, variable or unequal distribution of the stimulus field may sweep across face 1902 of sensor 1901*a* (e.g., XY plane), the magnitude sweeping from a density 1903*a* at time 1 ("t1") to a density 1903*b* at time 2 ("t2"). In one example, consider that a neuronal activity sensing system includes an array of 2,000 sensors. With a modulated drive field, an effective resolution of 10,000 sensors or more, and associated sensor data, provides for enhanced resolution based on the 10,000 "virtual sensors."

Drive depth controller 1925 is configured to control a depth of a stimulus or drive signal into a head of a user. In some examples, drive depth controller 1925 may be configured to modify a frequency (or range of frequencies) of a stimulus signal, which, in turn, may cause a stimulus field to vary in depth. As different biological materials respond differently to different frequencies, sensor subset selector 1921 and depth drive controller 1925 may operate cooperatively to sense a certain region and depth of the brain such as, for example, a hippocampus, which is located under the cerebral cortex. Depth drive controller 1925 may configure a drive signal to sense relatively shallow, such as surface features, or sense more deeper (e.g., using deeper frequencies) to sense deeper features. According to various embodiments multiple frequencies may be driven simultaneously to retrieve information from different depths. As shown in diagram 1900, the stimulus field may drive at different depths and may do so at differently at time 1 ("t1") and time 2 ("t2").

Sensor enhancement controller 1926 is shown to include a spatial sensing controller 1928 and a temporal sensing controller 1929, according to some examples. A spatial sensing controller 1928 is configured to configure one or more subsets of the sensors to drive sensing signals spatially (e.g., at regions of specific interest), with some regions employing more sensors than other regions so as to enhance resolution. In some cases, spatial sensing controller 1928 may control drive magnitude controller 1923 and drive depth controller 1925 to apply specific drive currents or voltages to different subsets of neuronal activity sensors at specific frequencies during, for example, an interval of time. Temporal sensing controller 1929 may control drive magnitude controller 1923 and drive depth controller 1925 to select different subsets of neuronal activity sensors at different times to apply specific drive currents or voltages at specific frequencies at the different times. As an example, temporal sensing controller 1929 may select sensing of brain portions 1809*a*, 1809*b*, and 1809*c* of FIG. 18 in a sequential pattern to sequentially sense neuronal activities associated with a motor cortex, a portion of an auditory cortex, and a portion of a visual cortex. Hence, these portions of the brain, which are spatially disposed at different locations, may be sensed temporally (e.g., simultaneously or sequentially) to detect and or correlate neuronal activity. In some examples, sensor enhancement controller 1926 may cause stimulus signal generator 1922 to drive multiple stimulus signals in accordance with frequency division multiplexing ("FDM"), time division multiplexing ("TDM"), code division multiple access ("CDMA"), or any other technique to drive AC stimulus signals into sensor 1901*a* associated with a specific location or time. Note that the same frequencies may not be used to drive each set of electrodes 1901*a*. As such, different sets of electrodes 1901*a* may operate simultaneously (or substantially simultaneously) to scan multiple portions of the brain that may be of interest.

Response signal detector 1924 includes a sensitivity manager 1927 that may be configured to detect characteristics of the response signals to, for example, filtering or enhancing data related to specific sensed attributes. For example, response signal detector 1924 may be configured to select response signals of selected ranges of frequencies of interest (e.g., specific ranges of frequencies may relate to specific types of biological materials of interest). In some cases, sensitivity manager 1927 may sense, for example, phase shifts between magnetically-generated fields and corresponding drive signals to select a subset of signals that may correspond to a specific drive waveform. Hence, sensitivity manager 1927 may control the sensitivity by, for example, implementing bandpass filtering, synchronous detection, demodulation, and similar known techniques. In some examples, sensitivity manager 1924 may control variable input impedances (e.g., to enhance sensitivities of sensors in certain regions) and sensitivities of response signal amplifiers or any number of structures and/or functionalities, such as any suitable arrangement of analog and mixed signal components, including, but not limited to, instrumentation amplifiers, gain amplifiers, analog-to-digital ("ADC") converters, digital signal processing ("DSP") elements, etc.

Response signal detector 1924 may also modify input impedances or vary differential gain when sensing magnetic or optical signals.

In view of the foregoing, neuronal activity transceiver 1920 may be configured to facilitate enhanced sensing capabilities either in the drive or pick up, whereby varying degrees of temporal resolution or spatial resolution are selectable to change the sensitivity and resolution of a neuronal activity sensing system. In some examples, neuronal activity transceiver 1920 may reduce temporal resolution (e.g., sweeping and changing fields from left, center, right, etc. along the XY plane portion). With drive magnitude controller 1923 configured to generate a drive stimulus signal in a range of MHz frequencies, spatial resolution may be enhanced with a minimal or negligible effects of a reduction in temporal resolution, according to at least one example.

Figure 20A:
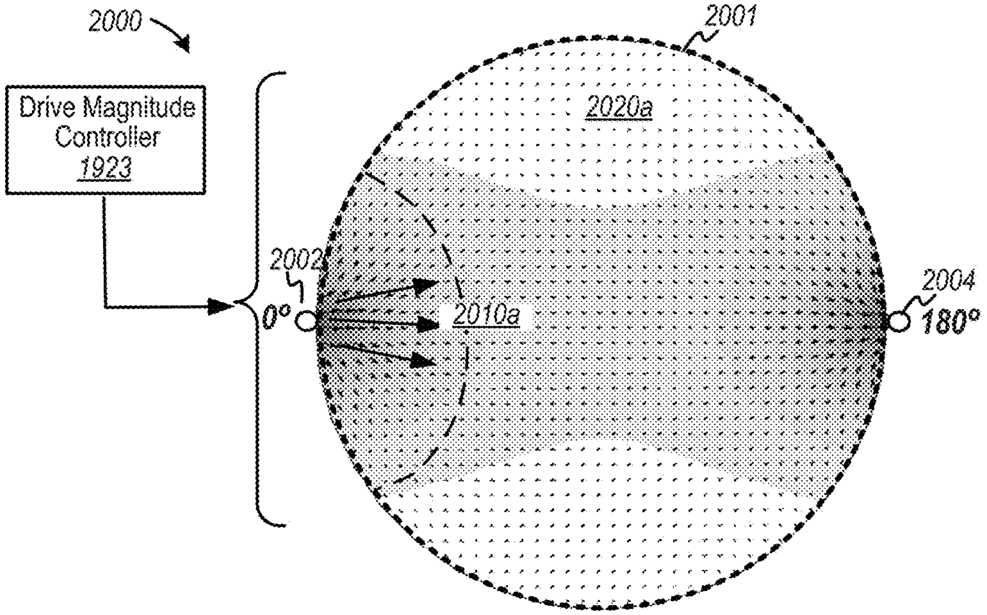
FIGS. 20A and 20B are diagrams depicting operation of an example of a drive magnitude controller, according to some embodiments.
Figure 20B:
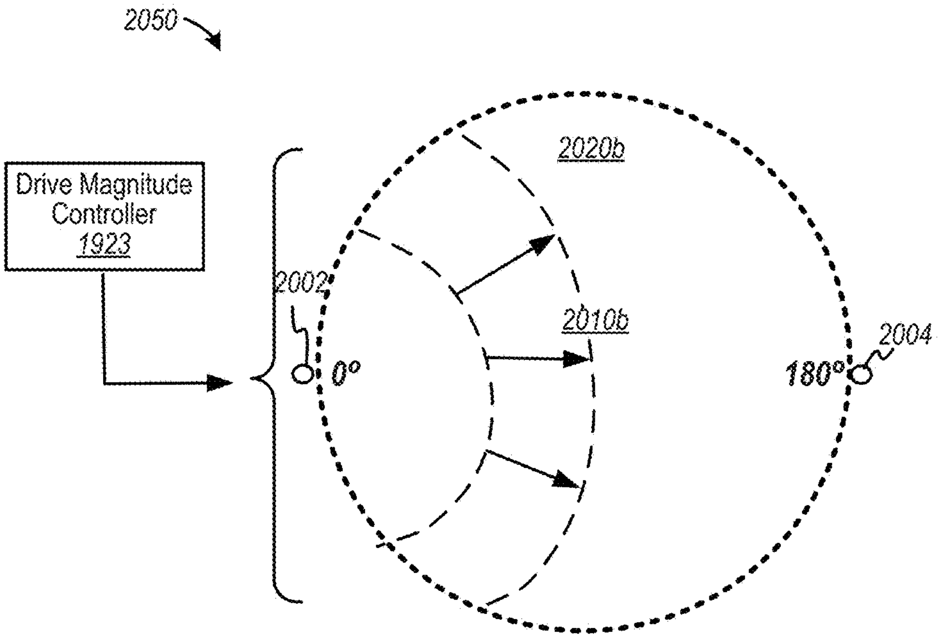

FIGS. 20A and 20B are diagrams depicting operation of an example of a drive magnitude controller, according to some embodiments. Diagram 2000 of FIG. 20A depicts a drive magnitude controller 1923 configured to generate an electric field 2020*a*, as a stimulus field, in region 2001 between electrodes 2002 and 2004. Drive magnitude controller 1923 is further configured to modulate a current density differently in different locations due to a change in magnitude and/or phase of currents/voltages/phases produced on electrodes 2002 and 2004. A maximal current density at time 1 is depicted as density 2010*a*. Diagram 2050 of FIG. 20B depicts a drive magnitude controller 1923 configured to generate a modulated or modified electric field 2020*b* at time 2. Drive magnitude controller 1923 is shown to propagate a maximal current density 2010*b* to a different location at time 2.

Drive magnitude controller 1923 is configured to change the manner in which the electrodes are driven such that initially there is more current at one edge of a sensor, and a next point or duration in time, there may be more current more in the middle of the sensor (e.g., in the middle of a surface area of a pickup coil). In subsequent time intervals, there will be more current at the opposite edge of the sensor. So, by changing a drive stimulus, there is a change in a distribution of the stimulus signal that is being detected. As the change in drive sweeps across a sensor, the resolution of a neuronal activity sensing system may be enhanced.

Figure 21A:
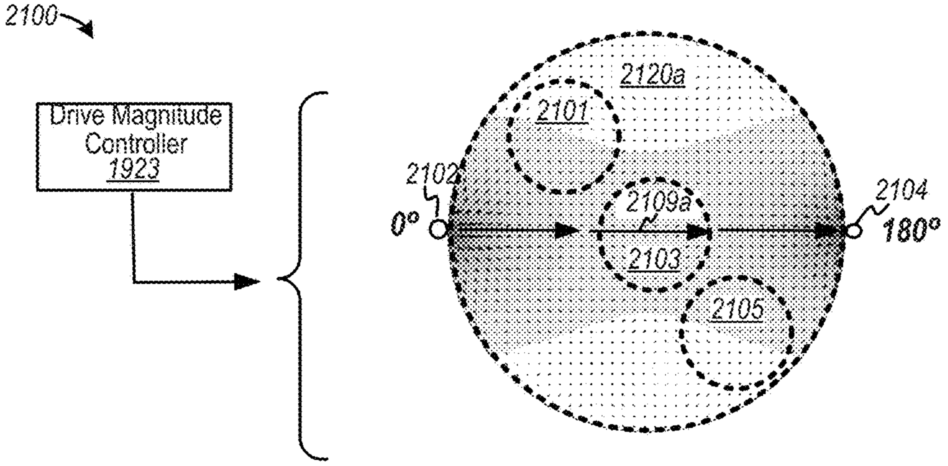
FIGS. 21A to 21C are diagrams depicting operation of another example of a drive magnitude controller, according to some embodiments.
Figure 21B:
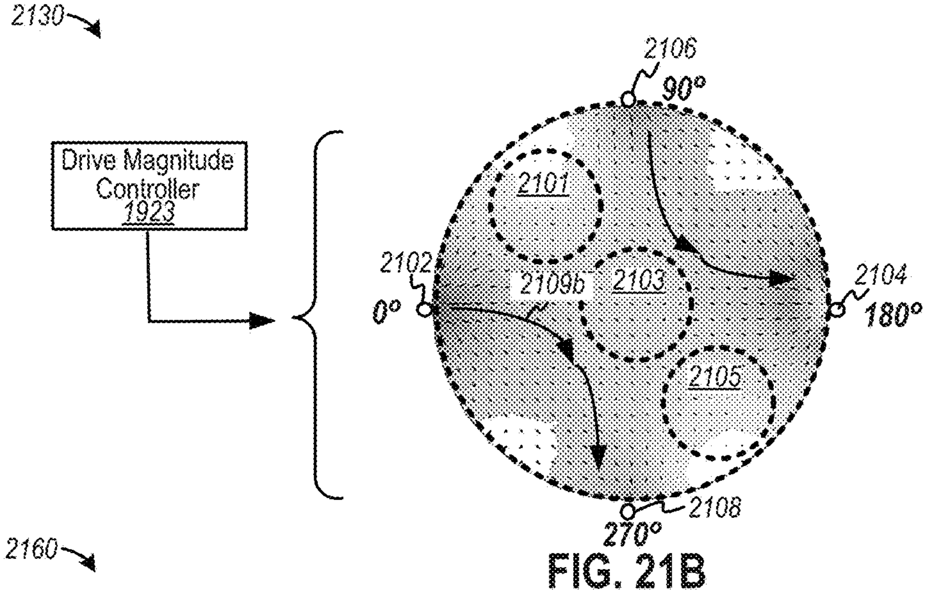
Figure 21C:
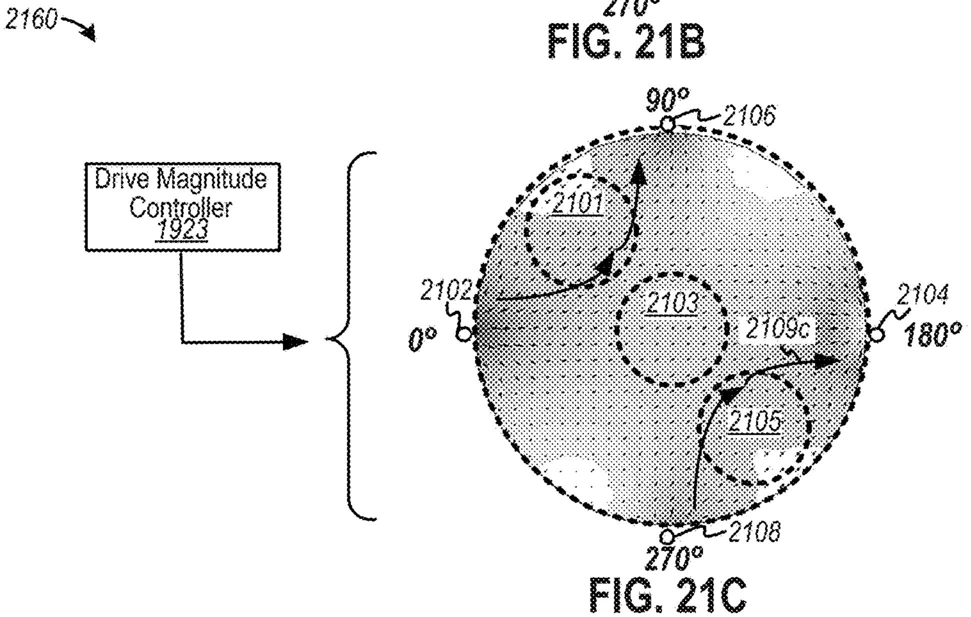

FIGS. 21A to 21C are diagrams depicting operation of another example of a drive magnitude controller, according to some embodiments. Diagrams 2100, 2130, and 2160 depict a drive magnitude controller 1923 configured to modulate current distributions, to, for example, move a current density along a face of magnetic sensing element (e.g., a search coil). Diagrams 2100, 2130, and 2160 further depict changing currents that moves, or is "swept," through a surface area (e.g., a sensor face) of magnetic sensing elements 2101, 2103, and 2105, each of which may be implemented as search coils. As shown in diagram 2100, an electric field 2120*a* generated between electrodes 2102 and 2104 produces a current density 2109*a* that is sensed by pickup coil 2103.

FIGS. 21B and 21C depict changing current densities implementing multiple electrodes, such as electrodes 2102, 2104, 2106, and 2108. As is shown, a current density is different in different places in each of FIGS. 21B and 21C due to a change in the magnitude and phase of an additional current or voltage injected via electrodes 2106 and 2108 at the 90 and 270 degree positions. The modulation of current density may be achieved by differing currents, voltages, and/or phases produced on the electrodes. A difference in sensitivity to different regions is illustrated in diagrams 2130 and 2160. By creating a non-uniform current field and changing the field over time, it is possible to determine relative contributions of different regions to an overall detected signal, thereby increasing an effective resolution of a neuronal activity sensing system. For example, changing an injected sinusoidal current signal at electrodes 2106 and 2108 of FIGS. 21B and 21C (e.g., the 90 and 270 degree positions), which has a magnitude less than the current injected between electrodes 2102 and 2104 (e.g., from 0 degrees to 180 degrees), then a secondary signal may be modulated at a rate slower than a carrier signal rate (e.g., modulating the secondary signal at 100 kHz). Hence, a primary pair of electrodes may be driven with a first current and a secondary pair of electrodes may be driven with a second current, whereby the voltage between a first electrode pair (e.g., electrodes 2102 and 2104) may be varied relative to a second pair (e.g., electrodes 2106 and 2108). Thus, as current at a region is increased, brain activity at that region may cause of the conductivity of, for example, the cerebrospinal fluid to change. Thus, increased current includes the changes in conductivity to yield detected brain activity.

FIG. 21B depicts a general path of current density 2109*b* between electrodes 2102 and 2108 and between electrodes 2106 and 2104. Note that current density 2109*b* is shown to pass at areas other than in surface areas within search coils 2101, 2103, and 2105. FIG. 21C depicts another general path of current density 2109*c* between electrodes 2102 and 2106 and between electrodes 2108 and 2104. Note that current density 2109*c* is shown to pass at surface areas within search coils 2101 and 2105. Again, creating a non-uniform current field over time facilitates different contributions at different regions to enhance an effective resolution.

Figure 22:
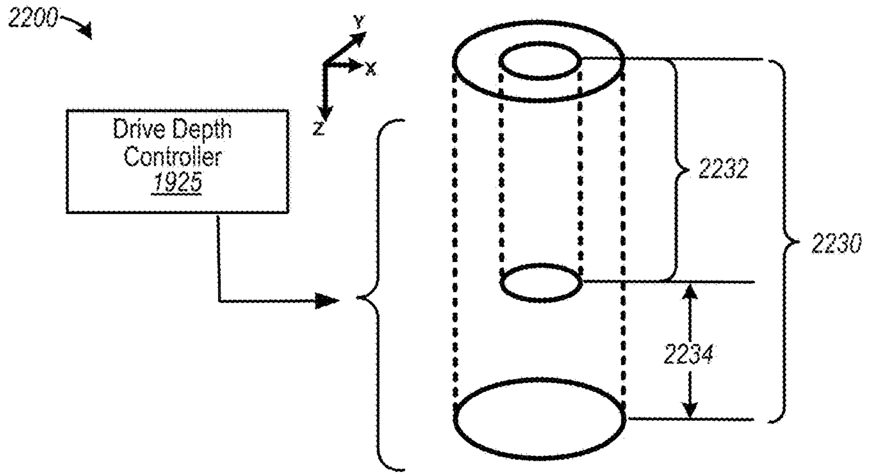
FIG. 22 is a diagram depicting operation of a drive depth controller, according to some embodiments.

FIG. 22 is a diagram depicting operation of a drive depth controller, according to some embodiments. Diagram 2200 depicts inductive-sensing elements including a first coil and a second coil disposed on, at, or within a range of distances from a scalp surface. The second coil may be a smaller-sized coil and is shown disposed inside a larger coil. Further, the smaller coil may be reversed-wound and include more turns than the larger coil. With more turns, the smaller second coil may be equally sensitive to a skull current as the larger first coil, but in the opposite direction. Therefore, the smaller reversed-wound coil may be disposed in the larger coil to provide skull current cancellation, whereby a skull current associated with a skull portion, which includes bone tissue, can be canceled out. The larger coil may be configured to sense induced magnetic fields from the skin surface to depth 2230, whereas the smaller coil may be configured to sense induced magnetic fields from the surface to depth 2232. Based on the number of turns and the directions of windings for the coils, induced currents cancel each other out within a region 2232. Note further, that drive depth controller 1925 may be configured to modulate (e.g., spatially modulate) the depths 2232 and 2230 to different values, for example, by varying the gains applied to the larger coil and smaller coils before combining their responses.

Figures 23A, 23B, 23C:
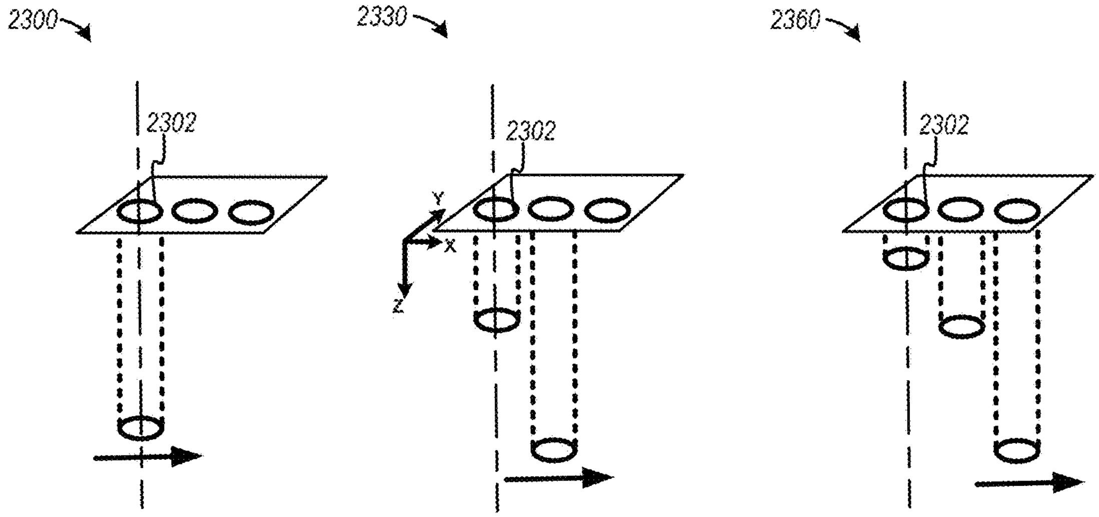
FIGS. 23A, 23B, and 23C are diagrams depicting another example operation of a drive depth controller, according to some embodiments.

FIGS. 23A, 23B, and 23C are diagrams depicting another example operation of a drive depth controller, according to some embodiments. Diagrams 2300, 2330, and 2360 depict a drive depth controller configured to modulate a drive depth for which a magnetic sensing element 2302, such as a search coil, senses over time. As shown, a drive depth for which a magnetic sensing element 2302 senses progressively becomes more shallow from diagram 2300 to diagram 2360.

Therefore, a stimulus signal may be generated to spatially modulate a drive depth temporally.

Figure 24:
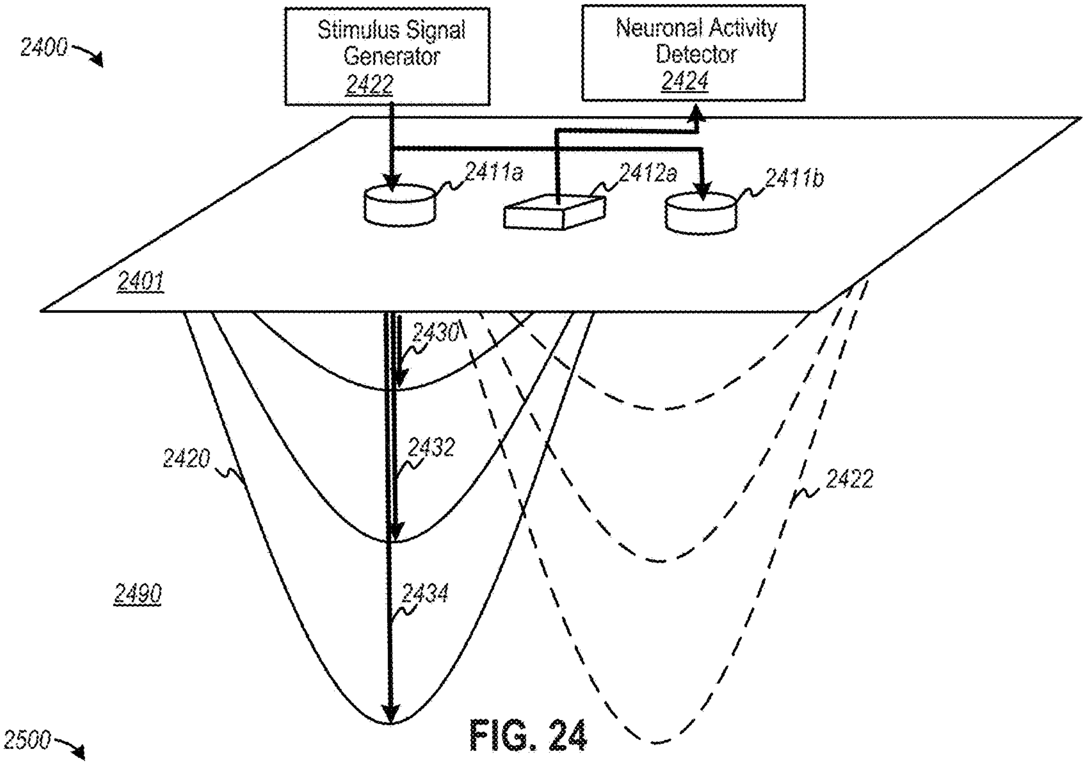
FIG. 24 is a diagram depicting an example of an optical-based physiological activity sensor in accordance with some embodiments.

FIG. 24 is a diagram depicting an example of an optical-based physiological activity sensor in accordance with some embodiments. Diagram 2400 depicts a physiological activity sensor including light emitting diodes ("LEDs") as stimulus signal elements 2411*a* and 2411*b* and a photodiode device as response signal element 2412*a*, which is configured to detect light emanating through biological tissue. As shown, a drive depth controller of stimulus signal generator 2422 may be configured to spatially modulate a light intensity or magnitude to drive a light field, at a specific location, to different depths 2430, 2432, and 2434.

Stimulus signal elements 2411*a* and 2411*b* and response signal element 2412*a* are shown to be disposed at or near surface 2401 of skin. Further, stimulus signal generator 2422 may be configured to cause light sources 2411*a* and 2411*b* to inject light field 2420 and light field 2422, respectively, into tissue 2490. Stimulus signal generator 2422 may be configured to cause light field 2420 and light field 2422 to generate light at a specific ranges of wavelengths (or frequencies) as well as specific ranges of intensity, whereby certain subcranial or subcutaneous biological structures may be detectable using certain wavelengths of light and/or certain intensities of light. Further to FIG. 24, neuronal activity detector 2424 is coupled to photodiode device 2412*a* to receive a response signal based on detected light that has been modified by the characteristics of the biological tissue through which the light passed. Hence, a modified light field signal may be indicative of an amount of neuronal activity or physiological activity associated with the biological tissue.

Figure 25A:
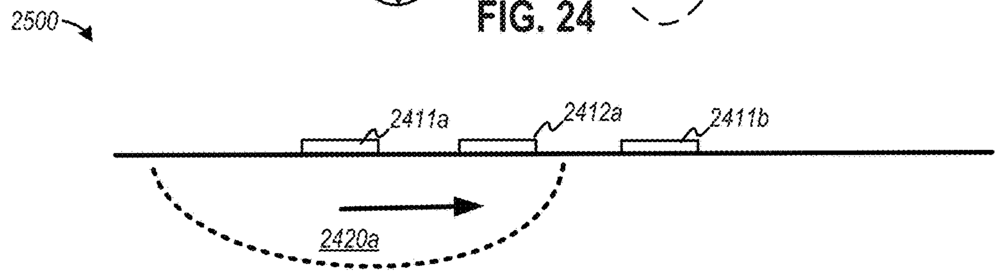
FIGS. 25A, 25B, and 25C are diagrams example operation of a drive magnitude controller for an optical-based physiological activity sensor, according to some embodiments.
Figure 25B:
Figure 25C:
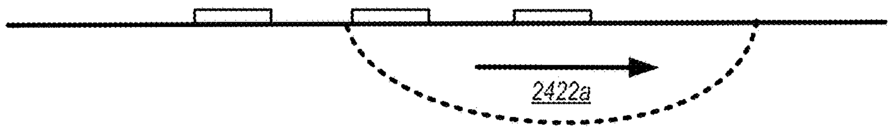

FIGS. 25A, 25B, and 25C are diagrams that show example operation of a drive magnitude controller for an optical-based physiological activity sensor, according to some embodiments. Diagrams 2500, 2530, and 2560 depict a physiological activity sensor including light emitting diodes ("LEDs") as stimulus signal elements 2411*a* and 2411*b* and a photodiode device as response signal element 2412*a*, which is configured to detect light emanating through biological tissue. As shown, a drive magnitude controller may be configured to drive a modulated light field, at a specific location associated with response signal element 2412*a*, whereby the light field initially received is light field 2420*a* (of light source 2411*a*), with a progressive mix of light field 2422*a* (of light source 2411*b*). In particular, consider that an LED 2411*b* starts at zero illumination and the other LED 2411*a* starts a full illumination, and causes different levels of intensity and illumination to sweep across the face of sensing element 2412*a*. Over time, more information is picked up as the light intensity sweeps from the left (i.e., only LED 2411*a* is on), to a middle region (a mix of both), and to the right (i.e., only LED 2411*b* is on). Thus, multiple "views" (or sets of sensed data) may be detected over the duration in which a driving voltage sweeps from one region to other region. Note that stimulus signal elements 2411*a* and 2411*b* may drive light sources with different frequencies and/or magnitudes.

In some examples, a differential gain of a neuronal activity detector may be implemented. For example, in view of the characteristics of the receive light fields (e.g., relating to magnitudes due to, for example, Lambertian emissions or other characteristics), a differential gain may be selected so as to enhance sensitivity in an overlap or combination, with sensitivity reduced in regions in which there is no overlap. As such, the combination of the light fields may be "weighted" (e.g., weighted sensor combination).

Figure 26:
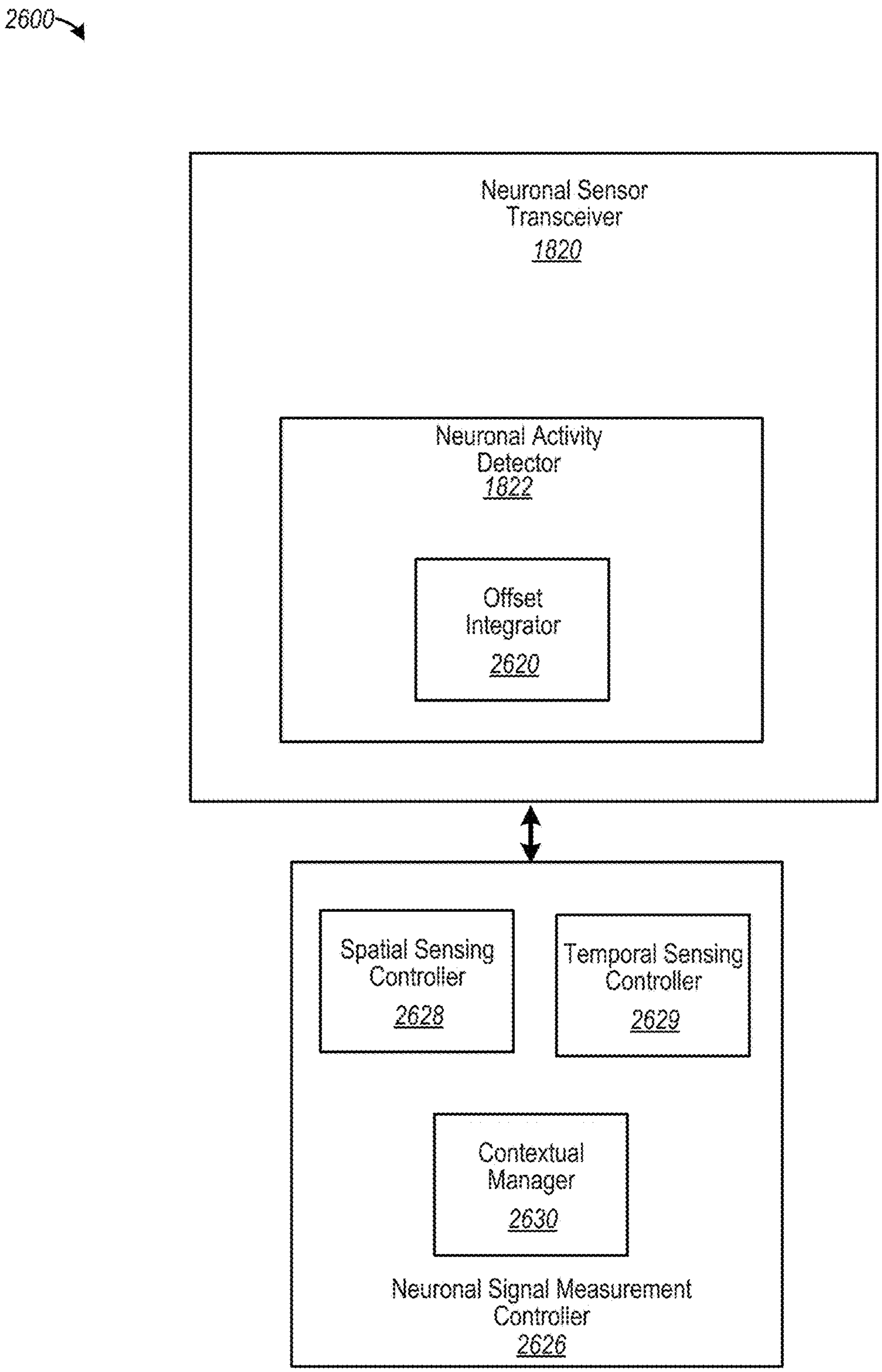
FIG. 26 is a diagram depicting an example of a neuronal sensor transceiver operationally coupled to a neuronal signal measurements controller, according to some examples.

FIG. 26 is a diagram depicting an example of a neuronal sensor transceiver operationally coupled to a neuronal signal measurements controller, according to some examples. Note that elements depicted in diagram 2600 of FIG. 26 may include structures and/or functions as similarly-named or similarly-numbered elements depicted in other drawings. Contextual manager 2630 may be configured to receive sensor data from other sources of data, such as non-neuronal sources of data, such as heart rate data, accelerometer data, and many other types of sensor data to provide a context in which to evaluate neuronal activity so as to more accurately match the temporal and spatial patterns of brain activity to data patterns representing an intent or a thought. Offset integrator 2620 is configured to estimate a size of a carrier so as to facilitate integration that "integrates out" the carrier signal. For example, consider that a response signal is rectified so that when it goes negative the signal may be rectified to be made positive. A digital-to-analog ("DAC") converter may be configured to receive the rectified signal and feed an output into an integrator. Since value of the digital-to-analog conversion is an average of the rectified signal, the result stays relatively level. As such, there is an offset value as an input into an integrator so that the estimated size of the carrier can be integrated out. Thus, a residual value can be amplified (e.g., "gained up) and fed through a DAC to arrive at an estimate amount of brain activity. As there need not be filtering, offset integrator 2620 may operate in a single cycle or multiple cycles so as to offset the integration with a negative value.

According to some embodiments, sensors and sensor arrays described herein may be modified further to enhance operation of a neuronal activity sensing system. For example, operating points of a neuronal activity sensor may be configurable. In the case of magnetic sensing elements, a coil may include ferrite and/or may operate as a fluxgate sensor. A magnetic sensing element may operate in relation to a point at which the ferrite saturates. In the presence of a background magnetic field, and there is an induced magnetic field applied, a linear response is available until a point of saturation, after which the response is non-linear. So, as a background magnetic field changes, the operation point may be moved at which the saturation point occurs. Thus, the sensor may be configured to be more or less sensitive a biological material in front of it.

For an optical-based physiological activity sensor, optical gradients may be implemented. A piece of plastic may be oriented across a face of a sensor that has a darker feature in one region at one or more frequencies and then gradually (e.g., as a gradient) moves to a more translucent or transparent feature at the other end, different frequencies having a similar or different gradient. By changing the intensity or frequency of illumination, a sensitivity of a photo diode may be changed relative to different positions. A photodiode may be provided with an optical filter configured to reduce intensity of light that may not match a filter frequency, and this may be used to further enhance the spatial resolution.

Figure 27:
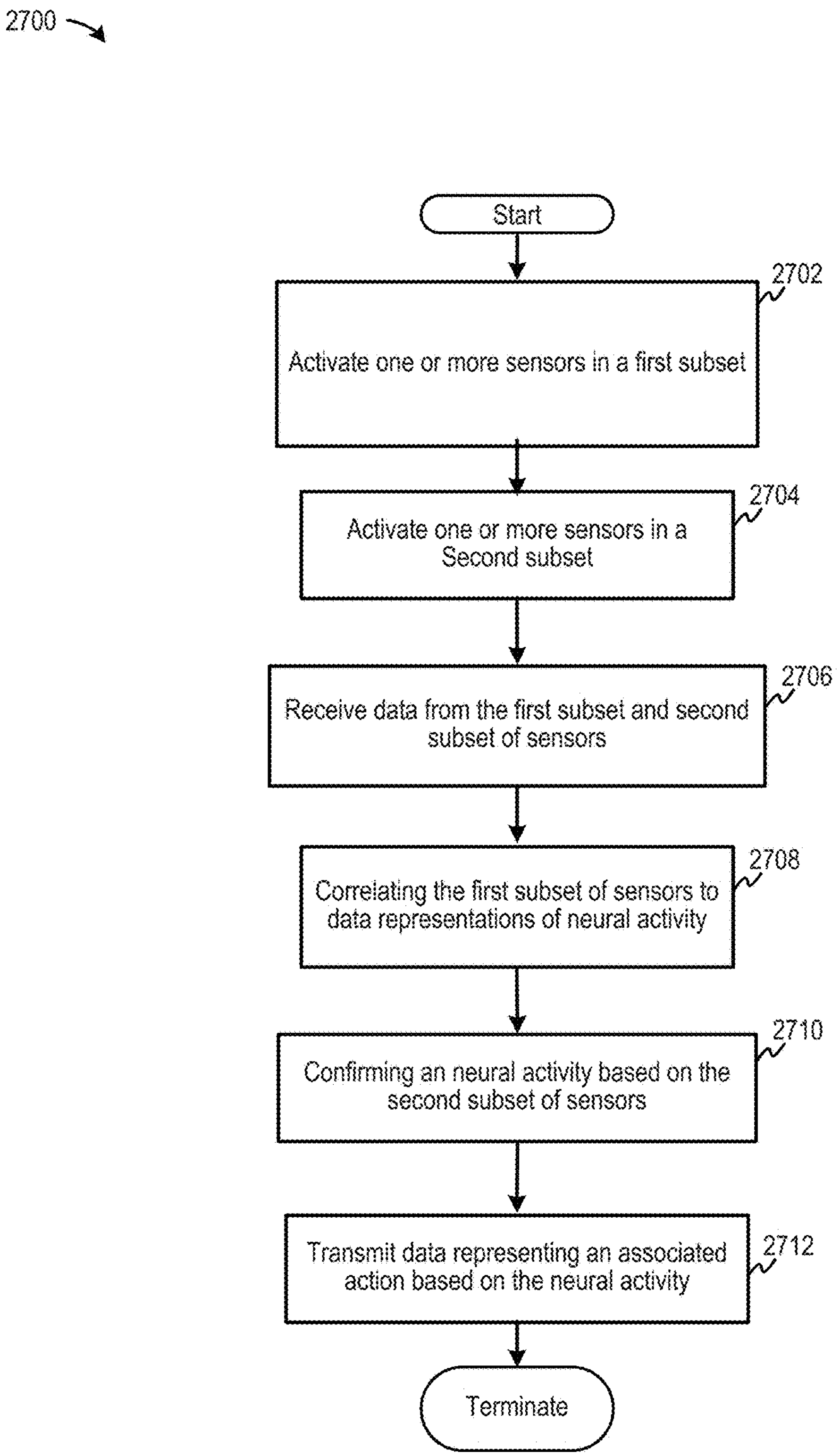
FIG. 27 is an example flow diagram, according to some examples.

FIG. 27 is an example flow diagram, according to some examples. Flow 2700 begins at 2702, at which one or more sensors in a first subset is activated. At 2704, one or more sensors in a second subset is activated to provide, for example, contextual sensors or other neuronal or non-neuronal activity sensors to enhance accuracy of determining an "intent," "command," or "thought," based on detect neuronal activity. At 2706, data is received from the first and second subsets of sensors, whereby the data may be an induced current that includes data that may be indicative of conductivity (or a change in conductivity) of a portion of the central nervous system, such as cerebrospinal fluid. At 2708, data from the first subset of sensors may be correlated to data representations of neural activity, such as data stored as patterns of brain activity. At 2710, neural activity may be confirmed using the second subset of sensors. At 2712, data representing associated action based on the neural activity may be transmitted, for example, to the user interface to provide interactions with the interface based on brain activity.

Figure 28:
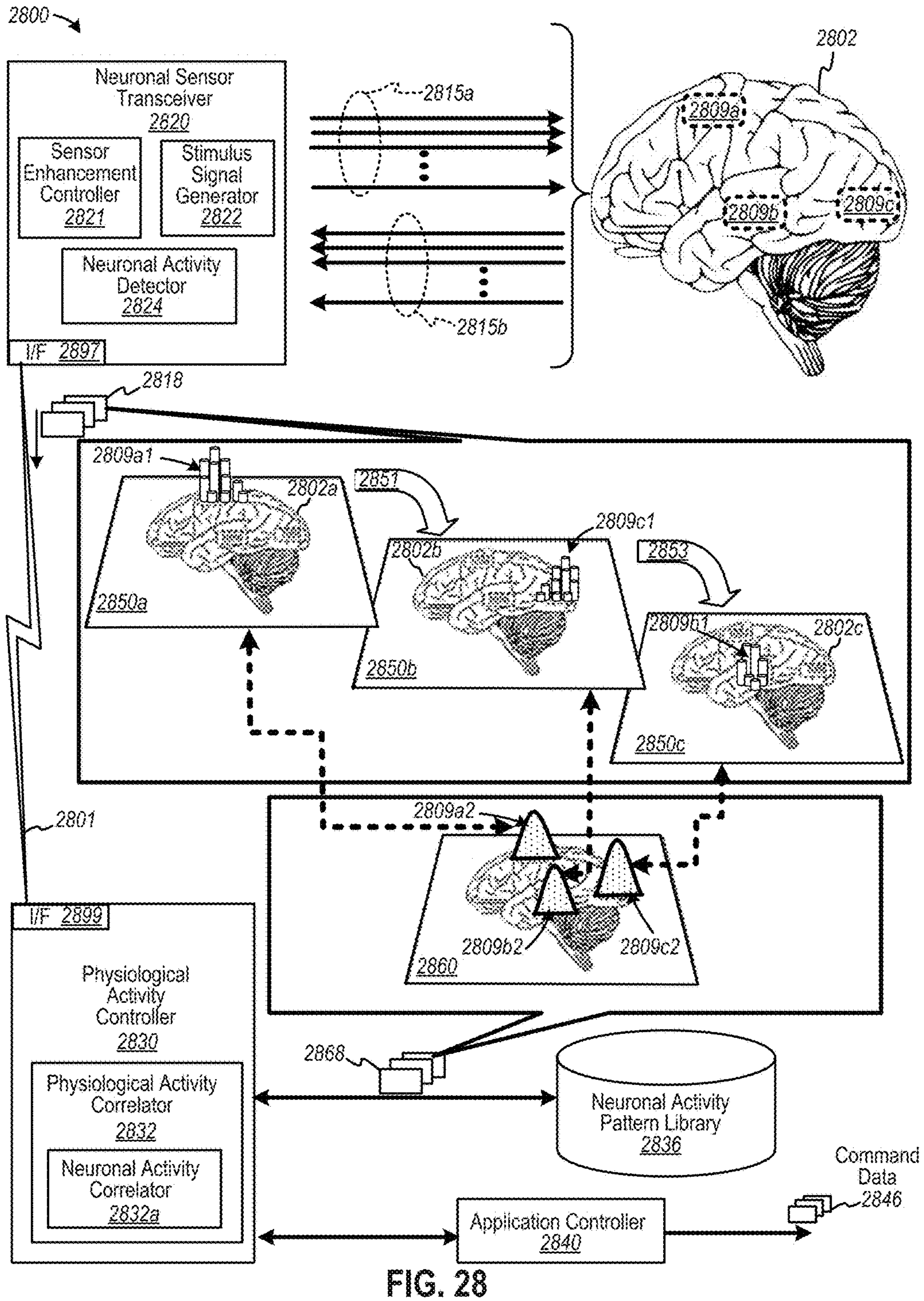
FIG. 28 is a diagram depicting an example of a physiological activity controller to identify neuronal states for facilitating a human-machine interface, according to some embodiments.

FIG. 28 is a diagram depicting an example of a physiological activity controller to identify neuronal states for facilitating a human-machine interface, according to some embodiments. Diagram 2800 depicts a physiological activity controller 2830 configured to receive physiological activity data, including neuronal activity data 2818, and to determine one or more neuronal states associated with, for example, an intent, a thought, an emotion, or a command, associated with a central nervous system of an organism. In this diagram, a portion of a central nervous system is depicted as a left cerebral hemisphere 2802 from which a subset of neuronal activity may be sensed to determine a neuronal state. In the example shown, physiological activity controller 2830 may include an interface ("I/F") 2899 configured to receive via a communication link 2801 (e.g., a wired or wireless communication channel) one or more subsets of data 2818 representing neuronal activity. In the example shown, data 2818 may be transmitted from an interface 2897 of a neuronal sensor transceiver 2820, which is configured to apply stimulus signals 2815*a* to one or more portions of biological tissues or components. Further, neuronal sensor transceiver 2820 may be configured to receive response signals 2815*b* from portions 2809*a*, 2809*b*, and 2809*c* of a central nervous system, whereby a response signal 2815*b* may include data representing a physiological activity characteristic that may describe, for example, a neuronal activity characteristic (e.g., a type of neuronal activity, an amount of neuronal activity, such as associated with action potentials, or any other characteristics of a central nervous system or any other physiological structure or component).

According to some embodiments, physiological activity controller 2830 may be configured to access a database repository 2836 to, for example, retrieve data 2868. Repository 2836 may include various data arrangements defined by a data model that organizes and relates neuronal activity data elements and neuronal activity data sub-elements so as to facilitate neuronal state identification for implementing a human-machine interface. The data model may also organize and relate neuronal activity data elements with respect to physiological activity data elements, non-neuronal activity data elements, contextual data elements, etc. In some examples, the data model may provide for data arrangements that include unique arrangements of data that form patterns of neuronal activity. These data patterns form at least a portion of a neuronal activity pattern library that may be used to, for example, match data generated by an array of one or more neuronal activity sensors (not shown).

In the example shown, physiological activity controller 2830 may include one or more of a physiological activity correlator 2832 and a neuronal activity correlator 2832*a*. As to the latter, neuronal activity correlator 2832*a* may include hardware or software, or both, and may be configured to correlate data 2868 representing data patterns of repository 2836 to sensed neuronal activity data to identify or categorize detected brain activities. The sensed neuronal activity data may be based on response data 2818 via neuronal sensor transceiver 2820 from an array of neuronal activity sensors (not shown). Thus, neuronal activity correlator 2832*a* may facilitate determination (e.g., in-situ determination) of one or more neuronal states by analyzing and correlating data from an array of physiological activity sensors with respect to data patterns representative of neuronal states.

In the example shown, physiological activity controller 2830 may receive data 2818, which may include subsets of neuronal activity sensed by neuronal sensor transceiver 2820. As shown, subset 2850*a* of neuronal activity data includes a graphic representation 2802*a* of a brain depicting neuronal activity data, such as neuronal activity 2809*a*1. Similarly, subsets 2850*b* and 2850*c* of neuronal activity data include graphic representations 2802*b* and 2802*c* of the brain, which, in turn, respectively depict neuronal activity data 2809*c*1 and 2809*b*1. As shown, subsets 2850*a*, 2850*b*, and 2850*c* depict different groups of neuronal activity data 2809*a*1, 2809*c*1, and 2809*b*1 that spatially emanate from respective surface portions 2809*a*, 2809*c*, and 2809*b* of left cerebral hemisphere 2802. In this example, neuronal activity data 2809*a*1, 2809*c*1, and 2809*b*1 are depicted as each having varied amounts of neuronal activity at a certain spatial resolution (e.g., a resolution corresponding to an area at which a value of neuronal activity is sensed). Note that other portions of left cerebral hemisphere 2802 (or a right cerebral hemisphere) may also be sensed contemporaneous (or substantially contemporaneous) with the sensing of neuronal activity data 2809*a*1, 2809*c*1, and 2809*b*1, but in this example, the associated neuronal activity with portions of the right cerebral hemisphere and other portions of cerebral hemisphere 2802 are not shown in this example. Note that while subsets 2850*a*, 2850*b*, and 2850*c* of neuronal activity data may be sensed (e.g., at sensors) or received at physiological activity controller 2830 contemporaneously (or substantially contemporaneously), diagram 2800 depicts arrows 2851 and 2853 to show a sequential temporal relationship such that subset 2850*a* is prior to subsets 2850*b* and 2850*c*, chronologically, and subset 2850*b* is prior to subset 2850*c*. Note that subsets 2850*a*, 2850*b*, and 2850*c* may be separated temporally by any amount of time.

In furtherance of the above-described example, pattern data 2868 is shown to include pattern data 2809*a*2, 2809*c*2, and 2809*b*2 of data representation 2860, which depicts patterns of neuronal activity amounts relative to general locations of a surface area of left cerebral hemisphere 2802. One or more subsets of pattern data may be correlated to identify a thought, an emotion, or command, whether at an atomic level (e.g., a unit level, such as an intent or a word) or at a macro-level (e.g., multiple thoughts or commands, or multiple intents or words). In various examples, pattern data 2809*a*2, 2809*c*2, and 2809*b*2 each may represent a neuronal state, or may, in combination, represent a single neuronal state based on spatial and/or temporal characteristics of the neuronal activity. Pattern data 2809*a*2, 2809*c*2, and 2809*b*2 may respectively correspond to neuronal states of "move" (e.g., right), "item" (e.g., a mouse or cursor), and "activate movement" (e.g., of hand).

Examples of brain portions 2809*a*, 2809*b*, and 2809*c* of hemisphere 2802 include a portion of a motor cortex, a portion of an auditory cortex, and a portion of a visual cortex, respectively. Hence, these portions of the brain, which are spatially disposed at different locations, may be sensed temporally (e.g., simultaneously or sequentially) to detect and or correlate neuronal activity associated with, for example, a user's intent to move a cursor in a right direction on a graphical user interface by moving the user's hand to the right. Neuronal sensor transceiver 2820 can transmit data 2818 that includes subsets 2850*a*, 2850*b*, and 2850*c* of neuronal activity that substantially coincides with the user's intent. Therefore, neuronal activity correlator 2832*a* may be configured to compare neuronal activity data 2809*a*1, 2809*c*1 and 2809*b*1 to pattern data 2809*a*2, 2809*c*2, and 2809*b*2, respectively. Neuronal activity correlator 2832*a* may detect a match based on the comparison, thereby identifying a user's intent to "move" an "item" to the right by "moving the hand" of the user.

In view of the foregoing, the structures and/or functionalities depicted in FIG. 28 illustrate a human-machine interface (or portions thereof) including a neuronal sensing system and a physiological activity controller 2830 that can directly or indirectly detect, characterize, and correlate neuronal activity of a brain to a data model that includes, for example, patterns of neuronal activity data or any other patterns of data that may assist in determining neuronal state, such as detecting, characterizing, and correlating patterns of non-neuronal activity data, physiological activity data, contextual activity data, etc., to identify one or more neuronal states (i.e., one or more thoughts, ideas, intents, emotions, commands, etc.). Indirect detection, characterization, and correlation of neuronal activity may be though the use of proxy physiological activities, which may include non-neural activities. In some examples, a neuronal state may represent a thought, an idea, and intent, an emotion, a command, or other brain-based activity, such as an archetype or concept that may be described by a word or phrase, or a group of related words and phrases. Note, too, that a neuronal state (e.g., "raise right arm to turn off light using a light switch") may be composed of multiple neuronal states (e.g., "move," "arm," "light off"). As such, a subset of pattern data for a neuronal state may be composed of multiple subsets of pattern data. Thus, physiological activity controller 2830 may be configured to match various types of sensed data against various types of pattern data to determine a neuronal state, such as a thought or intent, whereby the sensed data and pattern data may be based on data sensed via a "bio-inductance sensor" configured to induce currents in a central nervous system through electrodes. The bio-inductance sensor may implement a magnetic pick-up coil to receive magnetic field signals that include neuronal activity data. According to some examples, a human-machine interface (or portions thereof) including a physiological activity controller 2830 may implement a data model that includes data based on a 2-dimensional map of a brain to form and detect patterns of neuronal activity with which to predict, for example, an intent. Thus, 3-D spatialization of a brain need not be required, and may be performed as an optional implementation of the various structures and/or functionalities described herein. The structures and/or functionalities described herein further facilitate the performance of pattern recognition on finer subsets of data (e.g., lower-level neuronal or physiological activities). In some examples, spatial resolution of sensed neuronal activity data may be resolved to detect neuronal activity associated with a unit of resolution including a group of 5 or more neurons (or fewer). In one example, a neuronal activity sensor may detect a magnetic field associated with a surface area that may include about 5 neurons (more or less).

Physiological activity correlator 2832 of physiological activity controller 2830 may also include neuronal activity correlator 2832. Optionally, neuronal activity correlator 2832*a* may be implemented separately. According to some examples, physiological activity correlator 2832 may be configured to correlate multiple types of sensed data against multiple types of pattern data. For example, physiological activity correlator 2832 may be configured to correlate non-neuronal data, such as oxygenation levels of blood, glucose levels, etc., to non-neuronal data modeled (e.g., in accordance with a data model) as non-neuronal pattern data. As such, pattern data including oxygenation levels of blood during certain activities or in certain contexts may provide additional information as to a detected neuronal state as some types of non-neuronal activity data may operate as proxies for one or more characteristics of the activities of a central nervous system.

Neuronal sensor transceiver 2820 of FIG. 28 may be configured to include a sensor enhancement controller 2821, a stimulus signal generator 2822, and a neuronal activity detector 2824. Sensor enhancement controller 2821 may be configured to form "virtual sensors" that provide derived induced current signals (or any other derived response signals) to enhance the resolution of the neuronal sensing system greater than, for example, a resolution associated with sensors configured to detect activity associated with a left cerebral hemisphere 2802. Stimulus signal generator 2822 may be configured to selectably drive a stimulus signal, such as an alternating current signal, in association with one or more stimulus signal elements, such as one or more electrodes, magnetic drive coils, or light emitting sources, to generate a stimulus field (e.g., an alternating electric, optic, or magnetic field having varying magnitudes) in the biological tissues with which neuronal activity may be measured. Neuronal activity detector 2824 may be configured to receive a response signal that includes data representing an amount of neuronal activity. According to some examples, a response signal received by neuronal activity detector 2824 may be an induced signal indicative of the modified induced field received into, for example, a coil, photodiode, or any other sensory circuit or device.

In some embodiments, neuronal sensor transceiver 2820 may be configured to provide control data to sensor enhancement controller 2821 so as to cause stimulus signal generator 2822 to apply subsets of stimulus signals to subsets of neuronal and physiological activity sensors configured to sense data identified as being, for example, highly-relevant to a determination of the neuronal state. For example, sensor enhancement controller 2821 may be configured to adjust a configuration of an array of sensors so as to sense neuronal activity at brain portions 2809*a*, 2809*b*, and 2809*c* at relatively high levels of resolution (e.g., spatially and/or temporally), whereas other portions of brain 2802 may be sensed at lesser levels of resolution. In some examples, sensor enhancement controller 2821 may receive sensor control data via link 2801 from physiological activity controller 2830. For example, physiological activity controller 2830 may predict that, after detecting neuronal activity data 2809*a*1 and 2809*c*1, that neuronal activity data 2809*b*1 may be a likely occurrence. Thus, based on this prediction, physiological activity controller 2830 may transmit sensor control data that causes sensor enhancement controller 2821 to modify operation of stimulus signal generator 2822. As such, sensor enhancement controller 2821 may be configured to activate a portion of an array of sensors to sense neuronal activity at high resolution for brain portion 2809*b*. Thereafter, physiological activity correlator 2832 and/or neuronal activity correlator 2832*a* may compare pattern data 2809*b*2 to neuronal activity data 2809*b*1 to determine a neuronal state or a portion thereof.

Further, sensor enhancement controller 2821 may be configured to enhance resolution of the neuronal sensing system by, for example, controlling operation of stimulus signal generator 2822 and neuronal activity detector 2824 to increase (e.g., selectively) a number of sensor measurements associated with each physical sensor to a larger number of virtual sensor measurement. Accordingly, sensor enhancement controller 2821 may be configured to facilitate implementation of a number of "virtual sensors" from 4,000 to 5,000, up to 10,000, or greater, thereby increasing a number of sensed response signals (and resolution). As such, sensor enhancement controller 2821 may be configured to adaptively sense and/or generate different amounts of neuronal activity data, or other types of data, that physiological activity controller 2830 may correlate with corresponding data patterns to determine neuronal states. A neuronal state may refer, at least in some examples, to a set of one or more patterns of a central nervous system (e.g., spatial and/or temporal patterns of action potentials) that may be associated with a detectable thought, idea, intent (e.g., command), or the like, by correlating to one or more subsets of pattern data. In some cases, a neuronal state may be identified as a function of one or more sensed patterns of brain activity (e.g., as spatially-sensed patterns of data or temporally-sensed patterns of data, or both) that are matched against one or more patterns of neuronal activity data (or other types of data) stored in repository 2836.

Physiological activity controller 2830 may be further configured to transmit data representing one or more neuronal states (e.g., defining an intent, thought, or command) to application processor 2840, which, in turn, may be configured to map one or more intents, thoughts, or commands to a function of a particular interface or application, such as a text editor application. Therefore, application processor 2840 can generate command data 2846 suitable for the text editor application. Examples of command data 2846 may include interface commands to navigate an interface (e.g., user interface commands such as up, down, left, right, pan, zoom, etc.). Other examples of command data 2846 may include application-specific commands (e.g., identifying a word and performing an "insert" word operation, a back space command, select text command, text formatting commands, etc.). Another example of an application for which command data 2846 is generated includes a computer tomography application configured to build a 3D model of activity (e.g., neuronal or non-neuronal activities) within the central nervous system. Thus, diagram 2800 depicts examples of various components that may implement a neuronal activity sensing system that facilitates a neuronal-based human-machine interface.

Application controller 2840 may include hardware or software, or both, and may be configured to generate command data 2846 based on identified neuronal activities, as well as identified non-neuronal activities. Examples of command data 2846 data may include instructions (e.g., such as an application programming interface, or API) that invokes a command as a function of detected neuronal or non-neuronal activity. The commands may relate to interface commands, as well as commands or instructions to facilitate communication. In some embodiments, command data 2846 may also include instructions to provide an idea or thought that correlates to a particular type of neuronal activity. Therefore, should an organism be thinking of an automobile having a color "blue," the observation (e.g., a thought or idea) may relate to detectable neuronal characteristics constituting neuronal activity states of "blue" and "automobile." Thus, command data 2846 may specify the command of presenting a "blue automobile" to a user interface (e.g., a graphical user interface, or GUI).

Figure 29A:
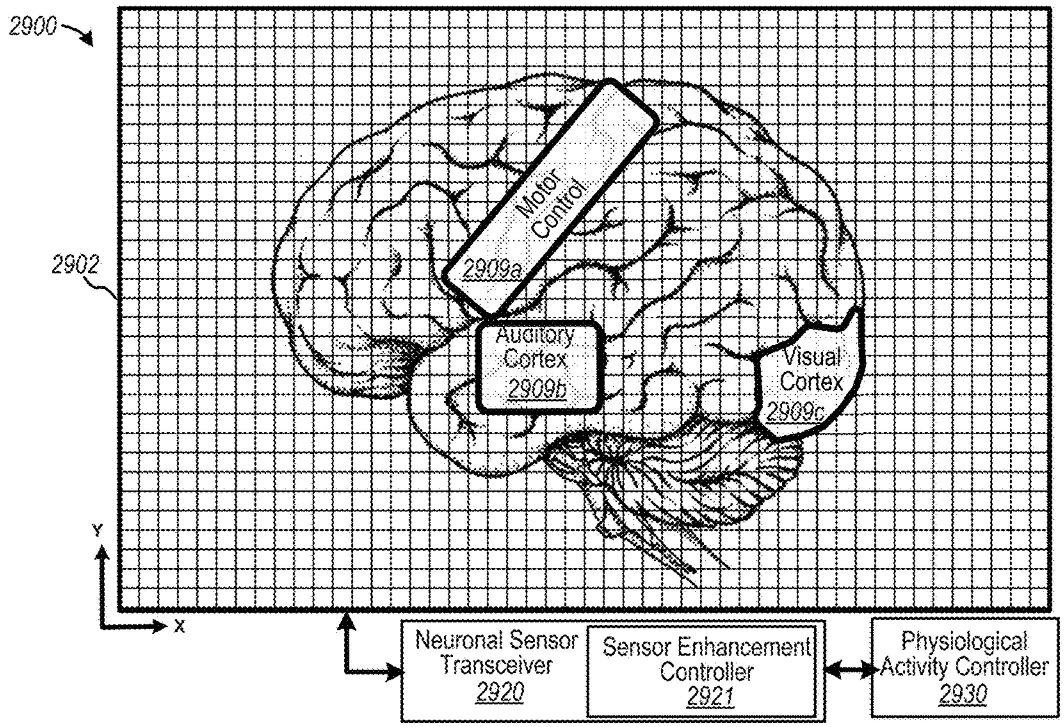
FIGS. 29A and 29B are diagrams depicting examples of adaptable sensor array configurations adapted to sense a neuronal activity of interest, according to some examples.
Figure 29B:
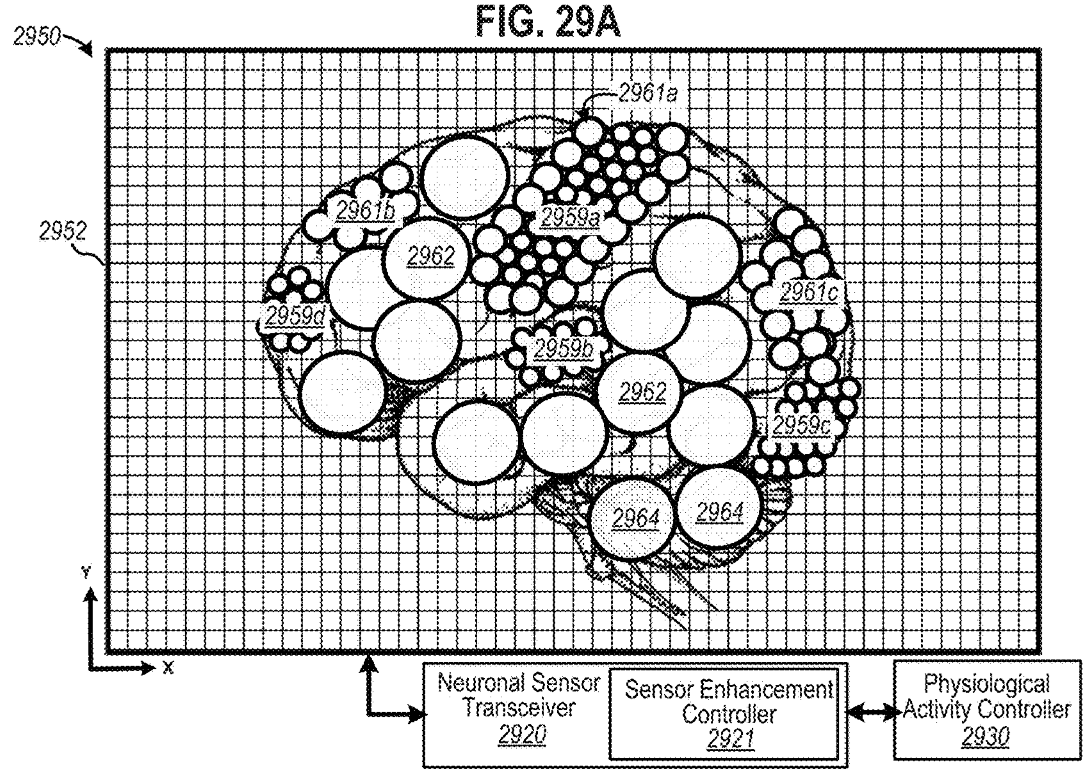

FIGS. 29A and 29B are diagrams depicting examples of adaptable sensor array configurations adapted to sense a neuronal activity of interest, according to some examples. Diagram 2900 depicts the 2-dimensional grid that may overlay a surface area of the brain, such as the surface area of a left cerebral hemisphere. Note that in various embodiments, grid overlay 2902 may be finer or coarser in resolution than as shown. In the example shown in FIG. 29A, grid overlay 2902 is an example of areas in a cerebral cortex from which neuronal activity data may be sensed. The cerebral cortex is physically disposed at the outer portions of the brain, thereby encapsulating inner portions of the brain, such as the hippocampus. According to some examples, sensing neuronal activity at outside regions of a brain (or inner surfaces of a skull) may be performed in relation to a 2-D mapping of the brain, which may be sufficient to generate patterns of neuronal activity that may be matched against sensed amounts of data to perform pattern recognition for deriving a neuronal state or thought. Diagram 2900 depicts a neuronal sensor transceiver 2920, which is shown to include a sensor enhancement controller 2921, and a physiological activity controller 2930. In one or more examples, neuronal sensor transceiver 2920 and/or physiological activity controller 2930 may be configured to adapt operation of sensor enhancement controller 2921 to focus sensing of neuronal activity and brain portions 2909*a*, 2909*b*, and 2909*c* to sense neuronal activity relating to motor control, an auditory function, and a visual function, respectively.

FIG. 29B is a diagram 2950 that depicts an example of sensor enhancement controller 2921 configured to adapt various subsets of arrayed sensors to provide relative degrees of resolution when sensing neuronal activity at, for example, different portions of a brain. In the example shown, sensor enhancement controller 2921 may be configured to provide relatively high resolution sensing using subsets of sensors 2959*a*, 2959*b*, and 2959*c* to sense motor control, auditory functions, and visual functions, respectively. Note, that in some cases, subset of sensors 2959*d* may be of similar resolution should correlated brain activity also be associated with a particular neuronal state. Further to FIG. 29B, other subsets of sensors 2961*a*, 2961*b*, and 2961*c* may be configured to provide less resolution than subsets of sensors 2959*a* to 2959*d*, whereby the resolution is adapted to provide sufficient information relative to the determination of a neuronal state as matched against a variety of neuronal data patterns. Furthermore, sensor enhancement controller 2921 may set subsets of sensors 2962 and 2964 to sense data at relatively low levels of spatial or temporal resolution, as the associated brain portions for these sensors may be least likely to demonstrate sufficient brain activity related to a specific neuronal state determination.

Figure 30A:
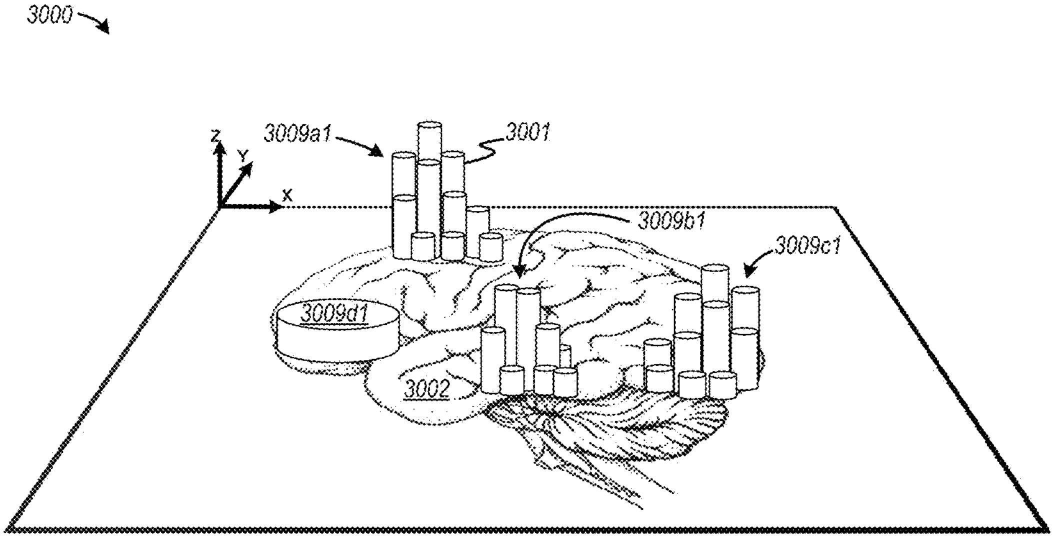
FIG. 30A is a diagram depicting an example of a data representation of sensed neuronal activity, according to some examples.

FIG. 30A is a diagram depicting an example of a data representation of sensed neuronal activity, according to some examples. Diagram 3000 depicts a two-dimensional ("2-D") representation of portions of a brain from which subsets of neuronal activity are sensed. One or more subsets of pattern data associated with one or more neuronal states may be generated based on such subsets of sensed neuronal activity. In the example shown, a surface area of at least a left cerebral hemisphere may be represented by a coordinate system in which a point or region on the surface area may be described in terms of X-Y coordinates. Further, a value of neuronal activity may be described in terms of a Z coordinate. Accordingly, data patterns of neuronal activity (or other relevant activity) may be generated based on the subsets of data shown in FIG. 30A for purposes of detecting future instances of neuronal activity that match a pattern consistent with neuronal activity shown in diagram 3000, or a variation thereof. So if sensed neuronal activity can be matched against patterns consistent with that shown in diagram 3000, then a particular neuronal state may be associated thereto for detecting future occurrences of similar neuronal states (e.g., similar future intents, thoughts, feeling, or commands).

In at least one example, subsets of neuronal activity, such as subsets **3009*a*1, 3009*b*1, and 3009*c*1 of neuronal activity, may be of similar or comparable levels of resolution. In the example shown, representation 3001 of a portion of neuronal activity is represented as a cylinder having a height, Z, and cross-sectional area, XY, which may relate to a level of resolution based on spatial dimensions of, example, a magnetic pickup coil at a specific point in time. Note that subset 3009*d*1 of neuronal activity has a relatively lower resolution in this example. In some cases, the cross sectional area of cylinder 3001 may relate to sensed data from a specific portion of the surface area of brain 3002 that is related to a specific type of brain activity (e.g., motor cortex). Note, too, that the different heights, Z, of representations 3001 of subset 3009*a*1** of neuronal activity may each represent a different level or value of neuronal activity associated with a portion of a motor cortex.

In at least one example, height Z may indicate a relative amount of neuronal activity in terms of a value of "action potential" for a particular sensor or cross-sectional area from which the value of the action potential is derived. According to some examples, neuronal activity may be measured in terms of action potential, which is a measure of the firing of a neuron having a pulse of duration and amplitude. Such neuron firings typically have comparable durations and amplitudes, or action potentials. Note that in accordance with some embodiments, a physiological activity correlator may be configured to decompose one or more sensor signals received from a neuronal sensor transceiver into action potentials, from which one or more patterns may be formed for performing future pattern matching to detect future neuronal states, including future thoughts, future intents, future feelings, and the like.

According to some examples, height Z may include any type or amount of various types of data, including action potential data, to characterize neuronal activity. For example, neuronal activity data for a portion of a central nervous system described by representation 3001 may describe a combination of an amount of action potential (e.g., associated with a portion of the brain or a neuronal activity sensor) with any other relevant data, such as contextual data, physiological data, non-neuronal data, etc., that may be used to assess and determine a neuronal state. In some examples, height Z may also include amounts of spatial data relating to, for example, amounts of neuronal activity at regions disposed below a surface area of a cerebral cortex (e.g., data representing neuronal activity may include neuronal-related data relating to structures or functions similar to a hippocampus or other interior brain portions).

Note that cross-sectional area XY of graphic representation 3001 need not be limited to a representation of a cylinder but may be represented by any other san XYZ coordinate system, but may be described in any spatial terms (e.g., a polar coordinate system, etc.).

Figure 30B:
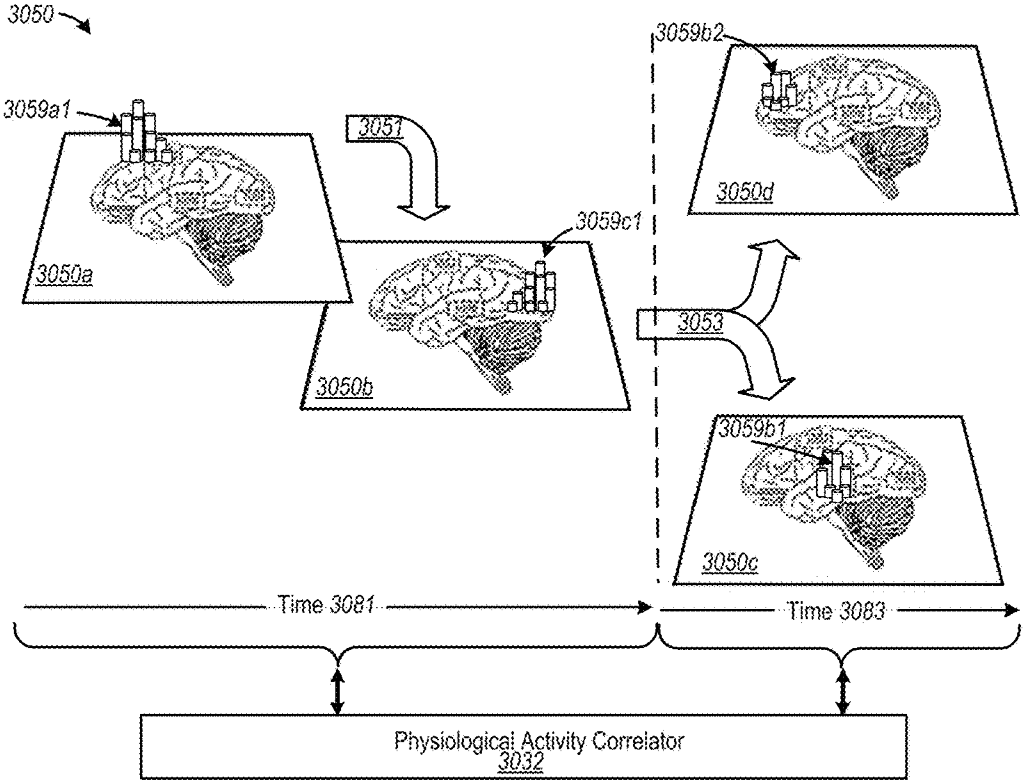
FIG. 30B is a diagram depicting a physiological activity correlator configured to temporally correlate neural activity, according to some examples.

FIG. 30B is a diagram depicting a physiological activity correlator configured to temporally correlate neural activity, according to some examples. Diagram 3050 depicts an example of a physiological activity correlator 3032 configured to analyze a stream of sensed neuronal activity to predict one or more neuronal states or corresponding subsets of pattern data. Therefore, physiological activity correlator 3032 may be configured to expedite determination of neuronal states by, for example, adapting neuronal activity sensing to detect expected or predicted amounts of neuronal activity against which one or more subsets of pattern data may be compared to detect a neuronal state. To illustrate, consider physiological activity correlator 3032 during time 3081 detects subsets of the neuronal activity, such as subset **3059*a*1 and subset 3059*c*1, the latter of which is detected after time 3051. Next, consider that physiological activity correlator 3032 matches subset 3050*a* of pattern data to subset 3059*a*1 of neuronal activity to determine, for example, a neuronal state equivalent to a thought of "moving" something (e.g., moving a cursor on a graphical user interface). Further, physiological activity correlator 3032 matches subset 3050*b* of pattern data to subset 3059*c*1** to determine, for example, a neuronal state equivalent to a thought of an "item" (e.g., a cursor).

According to some examples, a neuronal activity pattern library may include pattern data associated with neuronal states of "moving a cursor to the right" and "moving a cursor to the left." Based on these subsets of pattern data, physiological activity correlator 3032 may be configured to predict a direction (e.g., right or left) that a user desires to move a cursor. In one instance, physiological activity correlator 3032 may generate sensor control data to cause neuronal activity sensors to adapt sensing (e.g., adapt to a finer resolution) to sense subset **3059*b*2 of neuronal activity and subset 3059*b*1 of neuronal activity so as to capture predicted neuronal activity associated with a direction. In another instance, physiological activity correlator 3032 may be configured to match sensed subsets 3059*b*1 and 3059*b*2 of neuronal activity against respective subsets 3050*c* and 3050*d* of pattern data to detect neuronal state related to a "direction." Subset 3050*c* of pattern data may be associated with a neuronal state of a "right direction," whereas subset 3050*d* of pattern data may be associated with a neuronal state of a "left direction." So, during time 3083, physiological activity correlator 3032 may generate sensor control data for enhancing sensor operation to detect subsets 3059*b*1 and 3059*b*2 of neuronal activity and may also select subsets 3050*c* and 3050*d*** of pattern data to match against sensor data to identify whether a user desires to move a cursor either in a right direction or a left direction on a graphical user interface. In various examples, contextual data, physiological data, non-neuronal data, and other types of data may also be sensed and used to form pattern data with which to facilitate neuronal state determination through pattern matching, at least in some cases.

Figure 31:
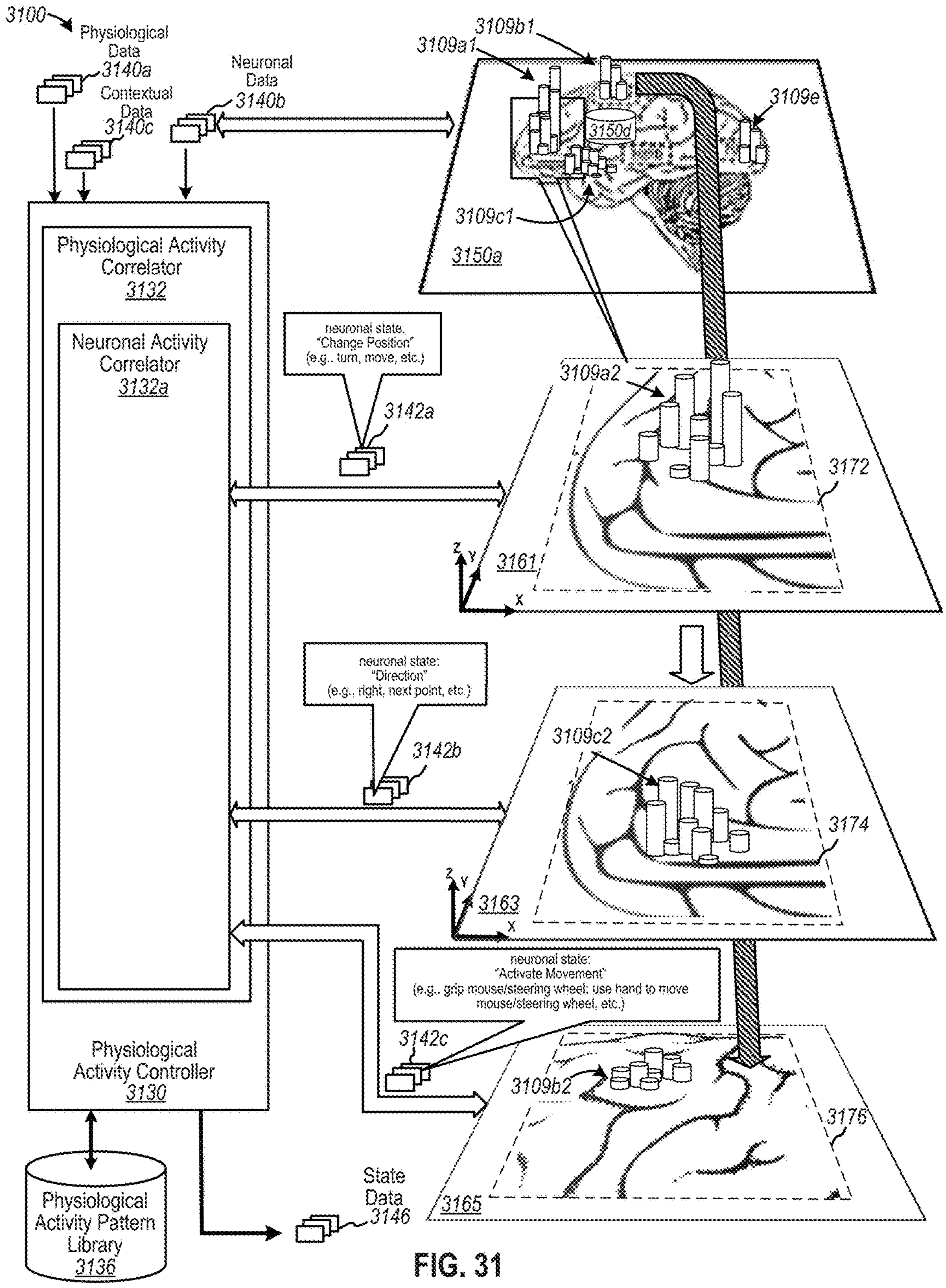
FIG. 31 is a diagram depicting an example of a physiological activity controller configured to match pattern data to neuronal activity data to determine neuronal states, according to some examples.

FIG. 31 is a diagram depicting an example of a physiological activity controller configured to match pattern data to neuronal activity data to determine neuronal states, according to some examples. Diagram 3100 includes a physiological activity controller 3130 including a physiological activity correlator 3132 and a neuronal activity correlator **3132*a*. Diagram 3100 also includes a physiological activity pattern library repository 3136 configured to store data for patterns of neuronal activity, physiological activity, non-neuronal activity, contextual activity, and other data that may be patterned or computed to determine one or more neuronal states with which to implement a human-machine interface, according to various embodiments. Note that elements depicted in diagram 3100 of FIG. 31** may include structures and/or functions as similarly-named or similarly-numbered elements depicted in other drawings.

In the example shown, physiological activity controller 3130 is configured to receive physiological data **3140*a*, neuronal data 3140*b* (e.g., neuronal activity data 3150*a*) and contextual data 3140*c*, among others not shown. Examples of physiological data 3140***a* include glucose levels, oxygenated blood flow and levels of oxygenation, heart rate, blood flow, etc. Examples of neuronal data 3140*b* includes neuronal activity data relating to visual activities, auditory activities, tactile sensations, coordinated motor control impulses, memory activities, speech-related activities, emotions, among others, whereby at least some of the aforementioned types may be determined through localized portions of a brain. Examples of contextual data 3140*c* may include data relating to an activity in which an organism is engaged (e.g., typing, talking, running, walking, sleeping, working, etc.), a geographic location, items and types of items (e.g., mobile phones, computer peripherals, user inputs, electronic interfaces, etc.) coincident with neuronal activity, and other contextual data sources. Physiological activity pattern library repository 3136 may be configured to store data for patterns for the above-described examples of data for matching patterns to determine neuronal states.

Diagram 3100 depicts an example of matching subsets of pattern data associated with neuronal states to sensed neuronal activity data to determine one or more neuronal states. In this example, physiological activity controller 3130 may be configured to access data patterns 3161, 3163, and 3165 from physiological activity pattern repository 3136, each data pattern being association with one or more neuronal states or archetypes that describe a concept or generalized intent or thought. Data patterns 3161, 3163, and 3165 include neuronal activity data subset 3109*a*2 associated with sensors disposed at or adjacent brain portion 3172, neuronal activity data subset 3109*c*2 associated with sensors disposed at or adjacent brain portion 3174, and neuronal activity data subset 3109*b*2 associated with sensors disposed at or adjacent brain portion 3176. Further to the example shown, data patterns 3161, 3163, and 3165 may be associated with neuronal states or archetypes that describe "change position" neuronal state data 3142*a*, "direction" neuronal state data 3142*b*, and "activate movement" neuronal state data 3142*c*, respectively.

To detect a neuronal state of a user to "move an item, such as a cursor, in a direction to the right using a user's hand," neuronal activity correlator 3132*a* may be configured to match pattern data subsets 3109*a*2, 3109*c*2, and 3109*b*2 against sensed neuronal activity data subsets 3109*a*1, 3109*c*1, and 3109*b*1, at or substantially at, a time internal and/or spatial region to determine an approximation of a user's intent or thought, which may be generated as state data 3146. In some examples, other neuronal activity data, such as data 3109*e* and 3150*d* may be used to match against other pattern data (not shown) relating to other words, phrases, or concepts to further refine the neuronal state determination process.

According to further examples, other examples of neuronal states 3142*a*, 3142*b*, and 3142*c* that are associated with subset of pattern data may correspond to an intent to use an interface (e.g., graphical user interface). For example, data patterns 3161, 3163, and 3165 may be associated with one or more neuronal states or archetypes relating to "Yes," "No," "OK," "Cancel," as well as navigation commands of "up," "down," "left," "right," "forward," "back," "roll," "tilt," "yaw," "pan," "zoom," etc. In some cases, any of pattern data 3142*a*, 3142*b*, and 3142*c* may include an image of any object, including a person, or any other complex sequences of patterns. A wide range of patterns may be detected and used for interface activity. Pattern data may be generated to correspond to a thought/imagining/intent to perform movement actions like "turn Left, Right, Up, or Down, or move Forward or Back, or Roll Left or Right, or Bank Left or Right, or Rotate Left or Right," among others.

As another example, any of pattern data 3161, 3163, and 3165 may be associated with neuronal states or archetypes relating to communication, such as pattern data that describe an intent to communicate, a recipient of communication, an atomic message (e.g., "I'll be 5 mins late"), a partial communicative phrase (e.g., a thought, sentence, etc.), and other communication-related intents for which a neuronal state may be associated, patterned, and detected. Other specific words or phrases, such as a pass phrase (e.g., password) may be detected, or more generally well-known words may be detected. Or, data patterns 3161, 3163, and 3165 may include data associated with the remembering, imagining, or seeing a particular image, icon, or person.

Physiological activity controller 3130 also may be configured to omit correlation of subsets of neuronal activity data 3140*b* to pattern data, such as neuronal activity data 3142*c*, which correlates to a neuronal state based on neuronal activity associated with activation of movement via motor cortex activity to control muscular movements. Therefore, a detected neuronal activity associated with a motor cortex, or similar brain portions that may control muscular movements (e.g., hands, arms, feet, legs, or other body portions), need not be subject to pattern detection. In some examples, other subsets of sensed neuronal activity data, such as sensed neuronal activity data 3142*a* and 3142*b*, may be sufficient to determine or identify an intent or thought a neuronal state without detecting neuronal activity associated with movement. Further, at least pattern data 3161, which may include neuronal pattern data associated with a "change of position," and pattern data 3163, which may include pattern data associated with a "direction," may be sufficient to determine a neuronal state relating to a user's intent to "move a cursor" "to the right on a graphical interface," without matching detection of neuronal activity to activate movement of a user's hand (i.e., without performing a match on pattern data 3165). Note, however, that in some examples, pattern data that correlates to a motor cortex may be optionally used to confirm a user's intent. For example, a detected motor cortex neuronal activity may be inconsistent with other subsets of sensed neuronal activity, and thus may provide additional information to invalidate a neuronal state or to perform corrective actions (e.g., detection of a user's intent to move a foot may be inconsistent with an action of moving a mouse-driven cursor on a user interface). In some embodiments, physiological activity controller 3130 may prioritize or "weight" pattern data that corresponds more to "an intent," such as imaging or thinking of a desired outcome (e.g., initiating a phone call) than to "an expression of intent," such as causing a body part to mobilize (e.g., using a finger to dial a phone number).

Figure 32:
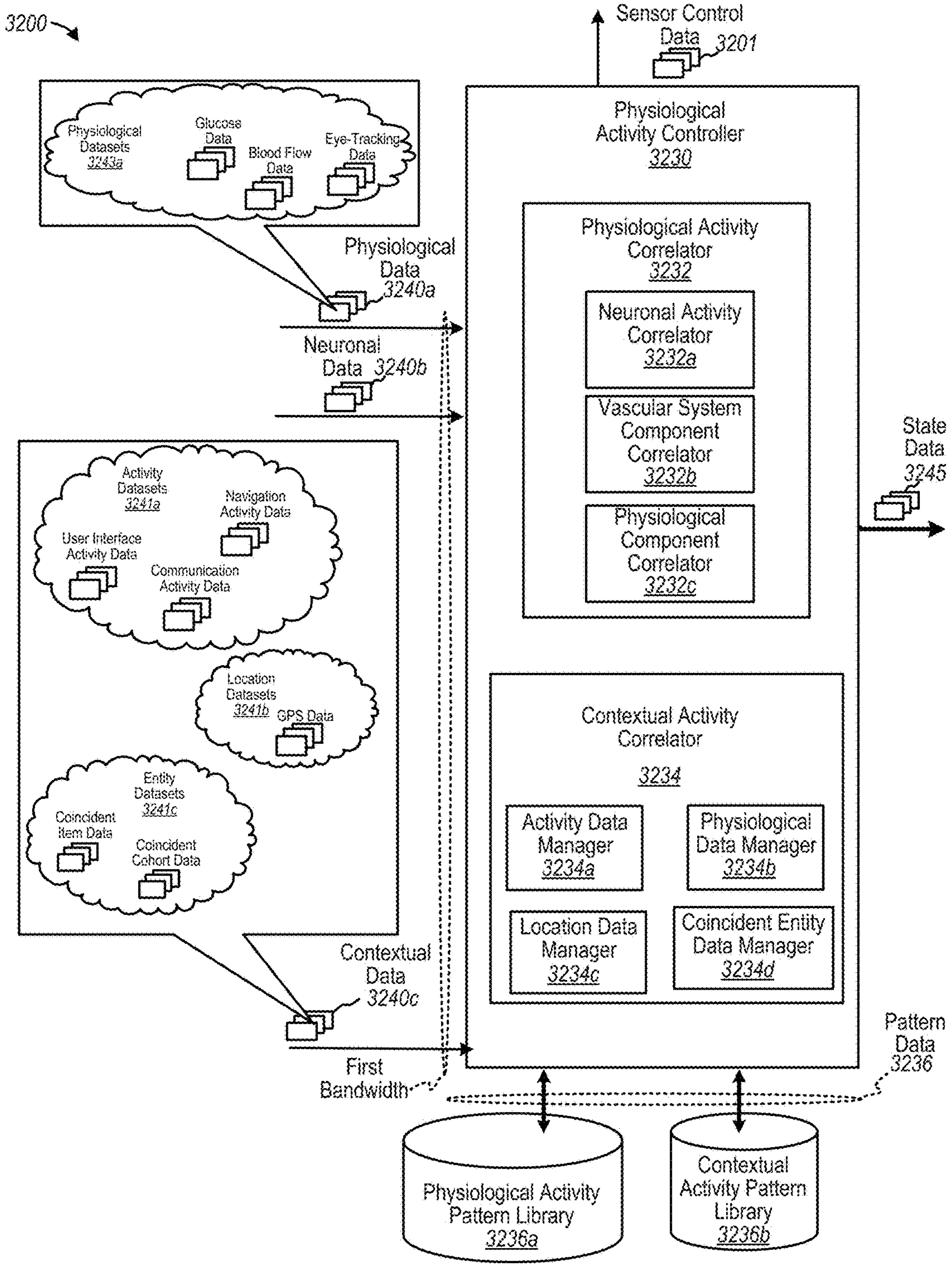
FIG. 32 is a diagram of yet an example of a physiological activity controller, according to some examples.

FIG. 32 is a diagram of an example of a physiological activity controller, according to some examples. Diagram 3200 depicts a physiological activity controller 530 including a physiological activity correlator 3232 configured to correlate pattern data to sensed physiological activity data, which may include neuronal activity data, and a contextual activity correlator 3234 configured to correlate pattern data to sensed contextual activity data. Physiological activity controller 3230 may be configured to receive physiological activity data 3240*a*, neuronal activity data 3240*b*, contextual data 3240*c*, etc., and may further be configured to receive pattern data 3236 by accessing pattern data for physiological activity in physiological activity pattern library 3236*a* and pattern data for contextual activity in contextual activity pattern library 3236*b*. Further, physiological activity controller 3230 is configured to correlate various types of pattern data to other types of pattern data, whether individually or collectively, to determine state data 3245, which may be representative of one or more neuronal states. According to some examples, elements depicted in diagram 3200 of FIG. 32 may include structures and/or functions as similarly-named or similarly-numbered elements depicted in other drawings. In some embodiments, a neuronal sensor transceiver (not shown) may be configured to transmit physiological activity data 3240*a*, neuronal activity data 3240*b*, contextual data 3240*c* at a first bandwidth, which may be a reduced amount of data. For example, data reduction or compression functions may be applied to the sensed data to reduce the bandwidth for purposes of transmitting the data, and for expeditiously determining one or more neuronal states.

In the example shown, physiological datasets 3243*a* include subsets of sensed physiological data 3240*a* from any of one or more types of sensors configured to sense data that describes one or more physiological characteristics of an organism. Examples of subsets of sensed physiological data 3240*a* include glucose data (e.g., glucose uptake data), blood flow data, blood chemistry data, heart rate data, respiration, eye-tracking data, and any other types of physiological data or characteristics of tissue.

Neuronal datasets include subsets of sensed physiological data 3240*b* from any of one or more types of sensors configured to sense data that describes one or more neuronal characteristics of an organism. Examples of subsets of sensed neuronal activity data include data relating to visual activities, auditory activities, tactile sensations, coordinated motor control impulses, memory activities, speech-related activities, emotions, among others. Neuronal activity data may be sensed via any number or types of sensors, including "bio-inductance sensors," "optical or light-based sensors," etc. In some examples, known brain-related or central nervous system sensors may also provide neuronal data 3240*b*, including, but not limited to, magnetoencephalography ("MEG") sensors, magnetic resonance imaging ("MRI") sensors, electroencephalography ("EEG") sensors, electrical impedance tomography ("EIT") sensors, bioimpedance sensors, optical-based blood oxygenation level sensors, intracranial electrodes, etc., any of which may be used individually or in combination with each other, such as with bio-inductance sensors. In some examples, neuronal activity data 3240*b* may include at least a portion that is of relatively high resolution either spatially or temporally, or both. Physiological activity controller 3230 may be configured to differentially sense neuronal activity in different regions of a central nervous system (i.e., different or specific patterns or arrangement of response signals may be sensed or detected as a function of the location in a central nervous system at which sensed activity occurs). Further, physiological activity controller 3230 may receive sensed neuronal data via a neuronal sensor transceiver (not shown), which may be configured to provide neuronal activity data 3240*b* as a spatio-temporal signal. For example, such data signals may be a time-series, whereby each time-slice may include a set of tuples each comprising a position (e.g., in 2D or 3D space) and one or more values, such as a resistance, a capacitance, a blood oxygenation level, or glucose uptake amount. The one or more values may be in the form of a scalar or a vector indicating an activity level for a region of neuronal tissue, such that an indication may represent whether a neuron fired in an adjacent position or region in a time slice, and/or a quantity (e.g., an approximate quantity) of neurons that may have fired in the adjacent position or region in the time-slice.

Contextual activity data 3240*c* may include, but is not limited to, activity datasets 3241*a*, location datasets 3241*b*, entity datasets 3241*c*, among others. Activity datasets 3241*a* include subsets of sensed activity data from any of one or more types of sensors (e.g., accelerometers, pedometers, etc.) configured to sense data that describes one or more activities in which an organism is engaged that may or may not be coincident to a determination of a neuronal state, whereby such activity may facilitate neuronal activity-to-pattern correlation. As an example, a portion of a neuronal state may include an intent to "change position of an item," whereby the type of item and how the position is changed may be a function of an activity being performed, such as navigating a user interface (e.g., moving a mouse, and, in turn, a cursor) or driving an automobile (e.g., moving or turning a steering wheel). Examples of subsets of activity datasets 3241*a* as contextual data 3240*c* include, but are not limited to, user interface activity data, navigation activity data, communication activity data, physical activity data, etc. Location datasets 3241*b* include subsets of sensed location or movement data from any of one or more types of sensors (e.g., GPS sensor, accelerometers, etc.) configured to sense or derive data that describes one or more locations at which a determination of a neuronal state for an organism is being performed. Thus, a type of location may facilitate neuronal activity-to-pattern correlation based on, for example, whether an interaction of a user interface is being performed at home or at a work environment. Entity datasets 3241*c* include subsets of sensed data associated with items, object, or organisms associated with a user for which neuronal activity-to-pattern correlation is performed (e.g., items, object, or organisms within proximity of the user that may influence a user's neuronal activity, including thoughts, intents, emotions, etc.). An example of subsets of entity datasets 3241*c* as contextual data 3240*c* include, but are not limited to, coincident item data, such as graphic user interfaces, mobile phones, computer peripherals, such as a mouse, that may be present or influential on the user's neuronal activity. An example of subsets of entity datasets 3241*c* as contextual data 3240*c* include coincident cohort data that describes identities and relationships of organisms to a user, such as friends, family, and co-workers, whereby the coincident cohort data may be used to detect whether a friend, a family member, or a coworker influences a user's neuronal activity, and, thus, a neuronal state. Thus, contextual data 3240*c* may be used to modify sensitivity of sensing and detecting pattern data based on the above-described contexts.

Note that any of the above-described types of data may be used as other types of data for any reason. For example, eye tracking data as a physiological dataset may be viewed or used as contextual data 3240*b* (e.g., a position of an eye and corresponding eye muscles may provide a context of an intent, thought, or emotion). As another example, physiological data, such as glucose levels, may be used or viewed as a proxy to detect a level of neuronal activity. Further, any of the above-described types of data or datasets may be weighted differently based on, for example, a degree of relevancy in determining a specific neuronal state.

Physiological activity correlator 3232 is shown in diagram 3200 to include a neuronal activity correlator 3232*a*, a vascular system component correlator 3232*b*, and a physiological component correlator 3232*c*. Neuronal activity correlator 532*a* may be configured to correlate one or more subsets of neuronal activity data **3240*b* to pattern data stored in physiological activity pattern library 3236*a* to facilitate neuronal state determination based on activity of the central nervous system. Vascular system component correlator 3232*b* may be configured to correlate one or more subsets of vascular system component data 3240*a*, such as glucose levels or flow rate of blood, to pattern data (e.g., patterns of glucose levels or flow rate of blood) stored in physiological activity pattern library 3236*a* to facilitate neuronal state determination based on activity of a vascular system of a user. Physiological component correlator 3232*c* may be configured to correlate one or more subsets of any physiological characteristic as physiological component data 3240*a*, such as respiration rate or skin conductivity, to pattern data (e.g., patterns of respiration rate or skin conductivity) stored in physiological activity pattern library 3236*a*** to facilitate neuronal state determination based on physiological characteristics (e.g., non-neuronal characteristics) of a user.

Contextual activity correlator 3234 is shown in diagram 3200 to include an activity data manager **3234*a*, a physiological data manager 3234*b*, a location data manager 3234*c*, and a coincident identity data manager 3234*d*. Activity data manager 3234*a* may be configured to receive subsets of activity data from activity datasets 3241*a* as contextual data 3240*c* to correlate against subsets of pattern data stored in contextual activity pattern library 3236*b*. Physiological data manager 3234*b* may be configured to receive subsets of physiological data as contextual data 3240*c* to correlate against subsets of pattern data stored in contextual activity pattern library 3236*b*. In this case, pattern data may include data representing patterns of physiological characteristics that may be correlatable to a neuronal state. For example, the physiological characteristics of one or more eyes of a user (e.g., sensed eye-tracking) may be used to correlate to patterns of data representing the same to detect a neuronal state or a predicted neuronal state. Location data manager 3234*c* may be configured to receive subsets of location data from location datasets 3241*b* as contextual data 3240*c* to correlate against subsets of pattern data that may be stored in contextual activity pattern library 3236*b*. In this case, pattern data in repository 3236*b* may include data representing patterns of locations, such as geographic locations, that may be correlatable to a neuronal state or a predicted neuronal state. Coincident entity data manager 3234*d* may be configured to receive subsets of entity data from the datasets 3241*c* as contextual data 3240*c* to correlate against subsets of pattern data that may be stored in contextual activity pattern library 3236*b*. In this case, pattern data in repository 3236*b*** may include data representing identities of entities (e.g., persons or items, such as implements) that may be correlatable to a neuronal state or a predicted neuronal state.

In view of the foregoing, physiological activity controller 3230 and one or more of its components, such as physiological activity correlator 3232 and contextual activity correlator 3234 to correlate the various types of pattern data to various types of pattern data, whether individually or collectively, to determine state data 3245, which may be representative of one or more neuronal states. Note that pattern data may be included in a single data arrangement or may be distributed over many data arrangements and repositories. According to some examples, physiological activity controller 3230 and one or more of its components may be implemented as a single structure and/or function, or any of the components or sub-structures and sub-functions of physiological activity controller 3230 may be distributed over any number of structures and functions that may be implemented in any combination of hardware and executable instructions.

According to some examples, physiological activity controller 3230 and/or one or more of its components may be implemented by the execution of executable instructions on one or more microcontrollers, graphics processing units ("GPUs"), digital signal processors ("DSPs"), field programmable arrays ("FPGAs"), application-specific integrated circuits ("ASICs"), of the like. Physiological activity controller 3230 may be operable as to perform pattern recognition that may be performed in any number of ways. For example, one or more types or subsets of data **3240*a*, 3240*b*, and 3240*c* may be formatted in one or more two-dimensioned ("2D") time series. In one case, physiological activity controller 3230 may be configured to detect whether a particular region of a central nervous system (e.g., a region known to be associated with an intent) may be active either instantaneously or over a relatively short period, which may be sufficiently long enough to sense the neuronal activity of interest. Neuronal activity data in the form of a time-series may be low-pass filtered, and a sensed level of neuronal activity may be compared to a threshold value (e.g., for a particular region of a central nervous system), whereby the threshold value may be included in a portion of pattern data. In another case, any number and type of data processing techniques, such as pattern recognition or machine learning, may be used. For example, any number and type of image processing techniques, or portions thereof, may be implemented by physiological activity controller 3230 to apply edge detection techniques to detect shapes in subsets of time-series data, whereby the detected shapes are compared against pattern data that includes patterns that are known to be associated with intent. Further, physiological activity controller 3230** may be configured to apply motion field analysis to detect characteristics of motions that may be correlatable to a particular intent.

Physiological activity controller 3230 and/or one or more of its components may be configured to perform spatio-temporal pattern recognition, and include a feature extractor (not shown) and a classifier (not shown), either of which may be implemented as a component of physiological activity controller 3230. A feature extractor may be configured to form or generate "features" from the time-series data, whereby such features may be amalgams of the data that may be useful as smaller-scaled entities of data patterns. In a specific example, a feature extractor may be configured to perform one or more of spatial and temporal wavelet decomposition, spatial frequency transformation, spatio-temporal frequency transformation, products of moments of time-series data (e.g., over an entire data space or over sub-regions), or any other suitable data processing, such as feature generation and extraction techniques using techniques of image processing.

A classifier, according to some examples, may be configured to classify the features in accordance with any number of techniques. For example, the classifier may implement Bayesian networks, neural networks, support vector trees, decision trees, etc. Pattern data may be modified (e.g., may evolve or be adapted) over time in accordance with Markhov modeling techniques, for example, or stochastic models. Also, well-known algorithms, such as a Viola-Jones algorithm may be applied.

According to some embodiments, physiological activity controller 3230 may be configured to correlate physiological activity data **3240*a*, neuronal activity data 3240*b*, and contextual data 3240*c*, as three-dimensioned ("3D") data, whereby above-described techniques may apply 3D image processing techniques. In a number of examples, patterns of data described herein may be pre-programmed (e.g., being predetermined through other methods, such as manual inspection of empirical data). According to some examples, physiological activity controller 3230 may predict a subset of neuronal activities that may occur in view of patterns of sensed data 3240, and may further generate sensor control data 3201** to cause neuronal activity sensors to adapt sensing (e.g., adapt to a finer resolution), thereby capturing predicted neuronal activity relatively expeditiously in a targeted fashion.

Figure 33:
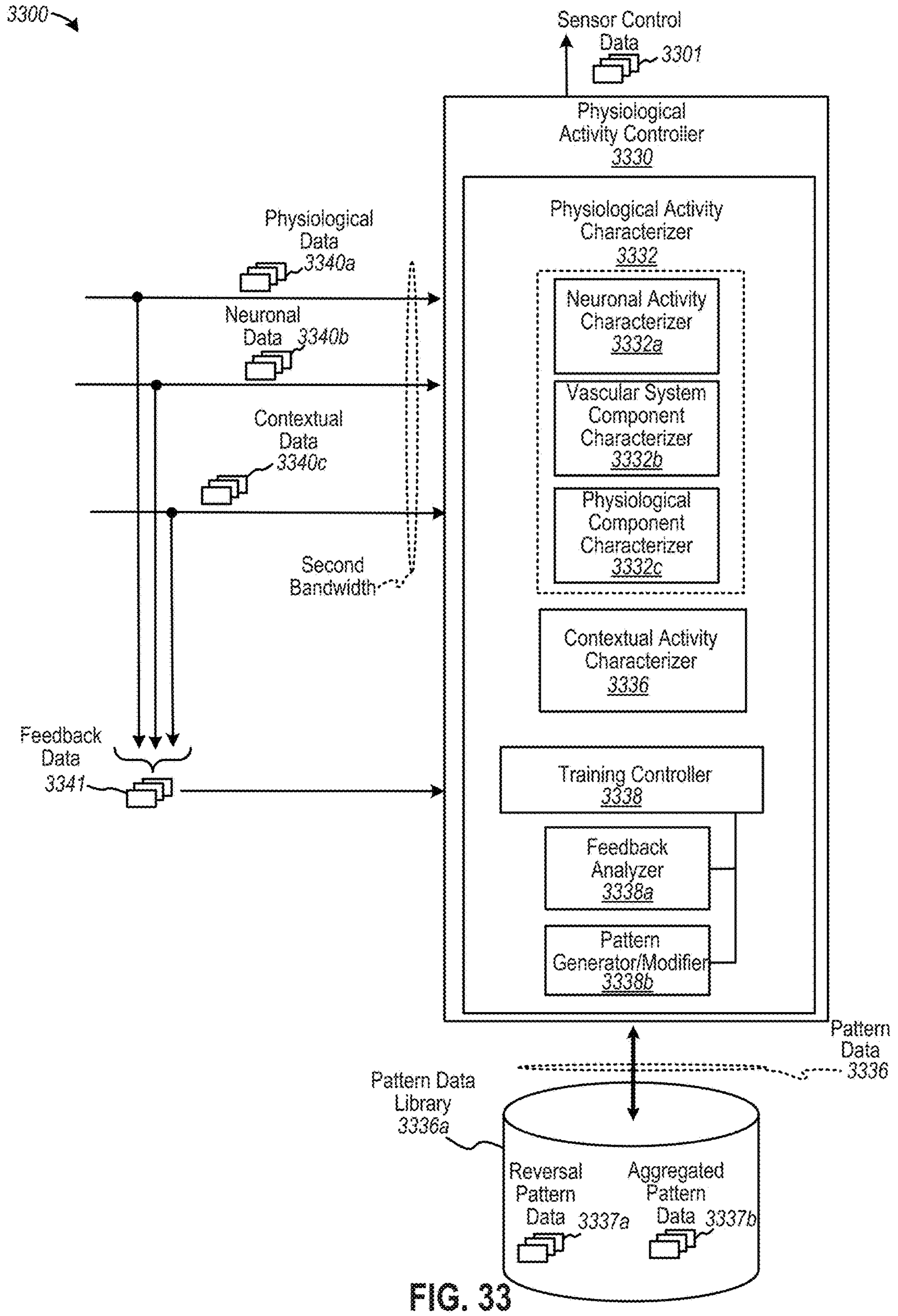
FIG. 33 is a diagram of an example of a physiological activity controller implementing a physiological activity characterizer, according to some examples.

FIG. 33 is a diagram of an example of a physiological activity controller implementing a physiological activity characterizer, according to some examples. Diagram 3300 depicts a physiological activity controller 3330 including a physiological activity characterizer 3332 configured to characterize physiological activity data 3340*a* and neuronal activity data signals 3340*b* for generating physiological data patterns and neuronal data patterns, respectively, and a contextual activity characterizer 3336 configured to characterize contextual activity data signals 3240*c* for generating contextual data patterns. Physiological activity controller 3330 is also shown to include a training controller 3338 configured to train generation of pattern data. In some examples, training controller 3338 may be configured to associate actions (e.g., of a user), as well as context, with sensed neuronal activity data. Training controller 3338 may be configured to train generation or validation of pattern data until, for example, a sufficient level of confidence is reached. Thereafter, the validated pattern data may be used to match against sensed central nervous system activity to infer, predict, or determine one or neuronal states. According to some examples, elements depicted in diagram 3300 of FIG. 33 may include structures and/or functions as similarly-named or similarly-numbered elements depicted in other drawings.

In some embodiments, a neuronal sensor transceiver (not shown) may be configured to transmit physiological activity data 3340*a*, neuronal activity data 3340*b*, and contextual data 3340*c* at a second bandwidth, which may include a full or substantially full amount of available data. For example, relatively large amounts of data may be supplied to physiological activity characterizer 3332 to accurately and precisely determine one or more data patterns that may be used to infer, predict, or determine a neuronal state. Physiological activity characterizer 3332 may further be configured to generate data-optimized patterns by, for example, reducing amounts of sensed data (e.g., by performing data decomposition, etc.) to match the pattern data to infer neuronal state.

Neuronal activity characterizer 3332*a* may be configured to receive neuronal data 3340*b* to generate data patterns that can be correlated to similar or equivalent instances of sensed neuronal activity values and patterns. Vascular activity characterizer 3332*b* may be configured to receive physiological data 3340*a* to generate data patterns that can be correlated to similar or equivalent instances of sensed physiological activity values and patterns (e.g., spatiotemporal patterns of action potentials and the like). Physiological component characterizer 3332*c* may be configured to receive neuronal data 3340*a* to generate data patterns that can be correlated to similar or equivalent instances of sensed physiological activity (e.g., non-neuronal) values and patterns. Contextual activity characterizer 3336 may be configured to receive contextual data 3340*c* to generate data patterns that can be correlated to similar or equivalent instances of sensed contextual activity values and patterns (e.g., values and patterns to represent user activities, locations, presence of implements and/or persons, etc.). The pattern data generated may be separate from, related to, or integrated with, one or more other types of pattern data. In some examples, the pattern data generated by neuronal activity characterizer 3332*a*, vascular activity characterizer 3332*b*, physiological component characterizer 3332*c*, and contextual activity characterizer 3336 may be correlated with each other and stored as pattern data 3336 in pattern data library repository 3336.

Neuronal activity characterizer 3332*a* may include hardware or software, or both, and may be configured to characterize instances of neuronal activity such that each instance of neuronal activity may be decomposed into, or otherwise stored as, a data pattern that is associated with a specific brain activity. In turn, the data pattern may be stored as a data arrangement within pattern data library 3336*a*. For example, neuronal activity characterizer 3332*a* may be configured to learn (e.g., via deep learning or other types of machine learning, as well as empirically) or otherwise associate identified “thoughts” or “intents” originating from a brain with such a pattern.

Training controller 3338 may be configured to generate one or more associations between an intent (e.g., a neuronal state relating to an interface intent) and pattern data. In some examples, exemplary sets of data streams of actions performed by a user (e.g., simulated user inputs) may be provided as training data to discover and evaluate predictive relationships between sensed data and pattern data. In some examples, training controller 3338 may be configured to perform supervised classification to recognize patterns, examples of which may include implementing machine learning, deep learning, support vector machine classifier generation, neural network implementation, or any amount or type of classification or regression computational process to recognize, evaluate, and validate patterns of data for implementing a human-machine interface according to various examples described herein. According to some examples, training controller 3338 may be configured to implement feedback, such as a user’s action that may coincide or substantially coincide with an occurrence of a particular intent or neuronal state. Note that initial patterns of data may be empirically generated, according to some examples, with the initial patterns of data being fed into physiological activity characterizer 3332 to learn, evaluate, validate, and adapt such patterns in view of additional information (e.g., feedback information).

Training controller 3338 may analyzed the feedback using feedback analyzer 3338*a*, such as feedback data 3341, to form pattern data relatively accurately and to adapt the pattern data (e.g., through continuous learning) using pattern generator/modifier 3338*b*. According to various examples, feedback data 3341 may be generated as an independent source of information (e.g., independent of a central nervous system) that provides information to assist training controller 3338 in determining whether a data pattern is being generated consistent with a contemporaneous action (e.g., user action), which may be used to confirm generation of an accurate data pattern. For example, feedback data 3341 may include data describing a user’s interaction with a graphical user interface (e.g., actions to control a mouse, a keyboard, a touchscreen with a hand, or actions of speaking into a voice-recognition system, and the like). Such user interactions with an interface (e.g., events like button clicks, words typed, etc.) may be recorded alongside subsets of neuronal activity data from a central nervous system, whereby the datasets may be included in a window of relatively short duration on either side of the event. An intent to strike a key on a keyboard may be detected prior to detection of an actual activation of the key as it is depressed. Thus, training controller 3338 may evaluate and correlate neuronal activity to user actions at different points in time (e.g., when implementing feedback data 3341).

As another example, consider that a video game controller may be used as a tracking device to provide feedback on user actions so that training controller 3338 can determine how to learn the thoughts or brain activity to interface with the game controller. For example, training controller 3338 may detect a user's intent to press "fire button" and correlate that with an event stream relating to patterns of brain activity. In some cases, a delay between the brain activity to decide the fire may be validated to confirm that an event of a finger that presses the fire button is substantially correlated (e.g., a confirmation may indicate that a relatively high degree of probability that a cause-and-effect relationship exists, whereby the cause is the intent to fire and the effect is a correlatable action of pressing of the fire button).

Note, too, that in some cases, training controller 3338 may implement feedback analyzer 3338*a* to analyze an event stream to segment sensed neuronal activity in the brain over a time interval sufficient to correlate the neural activity with the event. Additionally, training controller 3338 may be configured to evaluate neuronal activity data associated with active brain portions in relation to detecting the pressing the "fire button" over a number of trials (e.g., 100 times or more). Then, physiological activity controller 3330 and/or its components may evaluate the active brain portions with a specific action. The pattern data may include spatiotemporal "shapes" or "patterns" of action potentials that, like character or speech recognition, may be classified, and from which features may be extracted.

In some examples, training controller 3338 may be configured to detect instances in which a user stops performing an action associated with a subset of pattern data. For example, while neuronal activity data specifying an intent may be present (e.g., sensed), previously-sensed neuronal activity relating to motor control may not be present. As such, training controller 3338 may be configured to genericize patterns learned or formed with motor control (or any other type of central nervous system activity). For example, training controller 3338 may be configured to down-weight motor control activity data more strongly than neuronal activity associated with the correlated intent or neuronal state. At some point in time, a user may no longer regularly performs an action (moving a mouse, typing on a keyboard) as the pattern data and the human-machine interface is sufficiently performing intended actions. In this scenario, training controller 3338 may cause pattern generator/modifier 3338*b* to adapt the pattern data to omit portions relating to motor control or to deemphasize such data.

According to some embodiments, physiological activity characterizer 3332 and one or more of its components, such as training controller 3338, may be configured to detect patterns of neuronal activity that may be correlatable to a neuronal state or intent that specifies "an error occurred" or "an intent to reverse an action." In these cases, training controller 3338 may learn to recognize patterns of intent indicating "that is not right" (e.g., a pattern of central nervous system activity indicates a performed interface action was not a desired action that the user intended). Further, feedback analyzer 3338*a* may analyze the user's interactions with an interface (e.g., to detect pressing of a delete button or replacement of text) to characterize the interaction as a corrective action, or an "undo" command. Thus, training controller 3338 may use feedback analyzer 3338*a* to evaluate an event stream that includes "undo" neuronal state/intent or other corrective actions, which therefore can be used to generate a pattern of brain activity related to "undo." Subsequently, future detections of neuronal states or intents of "undo" may be performed using stored pattern data ("reverse pattern data") 3337*a* to automatically cause a human-machine interface to perform a corrective action without requiring a user to physically interact to perform the correction.

In some examples, physiological activity characterizer 3332 and one or more of its components, such as training controller 3338, may be configured to generate genericized patterns of neuronal activity (e.g., aggregated patterns of data as aggregated pattern data 3337*b*) for a population or sub-population of organisms, whereby the genericized patterns may not need customization to a specific user for facilitating a human-machine interface. However, such pattern data provide sufficient baseline with which pattern generator/modifier 3338*b* may adapt to provide customization to a specific user with decreased or negligible training cycles. As such, less training may enable a user to become proficient in using a human-machine interface of the various examples described herein. In one example, patterns from a group of users for a particular intent (e.g., about 100 users performing an "OK" action about 100 times) may be analyzed to form an aggregate pattern 3337*b*, whereby pattern 3337*b* may be used to optimize the learning process for an individual user.

Physiological activity characterizer 3332 and one or more of its components may be further configured to emphasize or weight subsets of pattern data that may be associated with sensed neuronal activity data originating at a particular region of a central nervous system. For example, certain identified regions of a central nervous system may correlate relatively high in determining "interface" intent (e.g., neuronal states associated with interacting with an interface, such as a graphical user interface). Examples of such regions include a visual cortex or system (e.g., for identifying interface features), the hippocampus, the cerebellum, etc. Therefore, physiological activity controller 3330 may generate sensor control data 3301 that is configured to sense (e.g., exclusively or preferentially) neuronal activity data from one or more of the above-described regions. In operation, a physiological activity correlator (not shown) of physiological activity controller 3330 may be configured to weight data patterns associated with such regions more highly (or use them predominantly, exclusively, or in a prioritized fashion). In one example, neuronal activity need not directly map to specific regions of the brain. As such, classes of pattern may be generated in connection with multiple regions that may be contributory in determining a certain intent or neuronal state. In one example, rather than processing an entire brain contemporaneously, interface-intense neuronal activities (e.g., intent to perform: up, down, left, right, or other navigation commands) may be processed such that associated brain portions may be processed at higher resolutions than, for example, speech center-related sensors.

In the context of a user's interaction with a graphical user interface, the usage of the visual cortex may be more prevalent than, for example, an auditory cortex as auditory cues may not be used. From time-to-time (e.g., dynamically), certain regions of the central nervous system may be emphasized or used to train, generate, and detect patterns on contextual data (e.g., data representing a type of task or activity involved). A selection of interface tasks, where multiple are available, may also be influenced by neuronal activity. For example, if a region of the central nervous system involving language becomes more active, this may be an indication that a typing-like task may be intended. This detected state may cause physiological activity controller 3330 to generate state data that is configured to activate a suitable typing-like interface element (e.g., bringing up a form field in a graphical interface into which text may be typed). In addition, the weighting or prominence of patterns for recognizing language activities may increase so as to enhance an accuracy in detecting neuronal states based on weighted pattern data.

Physiological activity controller 3330 and/or one or more of its components may be configured to perform spatiotemporal pattern recognition to generate patterns. For example, physiological activity controller 3330 may include a feature extractor (not shown) and a classifier (not shown), either of which may be implemented as a component of physiological activity controller 3330. A feature extractor may be configured to form or generate "features" from the time-series data, whereby such features may be amalgams of the data that may be useful as smaller-scale entities of data patterns. In a specific example, a feature extractor may be configured to perform one or more of the following to generate pattern data: spatial and temporal wavelet decomposition, spatial frequency transformation, spatiotemporal frequency transformation, products of moments of time-series data (e.g., over an entire data space or over sub-regions), or any other suitable data processing, such as feature generation and extraction techniques using image processing techniques, etc.

A classifier, according to some examples, may be configured to classify the features to generate patterns in accordance with any number of techniques. For example, the classifier may implement Bayesian networks, neural networks, support vector trees, decision trees, etc. Pattern data may be modified (e.g., may evolve) over time in accordance with Markhov modeling techniques, for example, or stochastic models. Also, well-known algorithms, such as a Viola-Jones algorithm may be applied.

In view of the foregoing, physiological activity characterizer 3332 and one or more of its components, such as training controller 3338, may be configured to generate patterns of data (e.g., neuronal activity data) that may be implement in any of the following applications: driving a graphical user interface ("GUI"), answering a phone call, initiating a conversation, typing text, drawing, controlling a modeling system, controlling a camera, and any number of applications.

Figure 34:
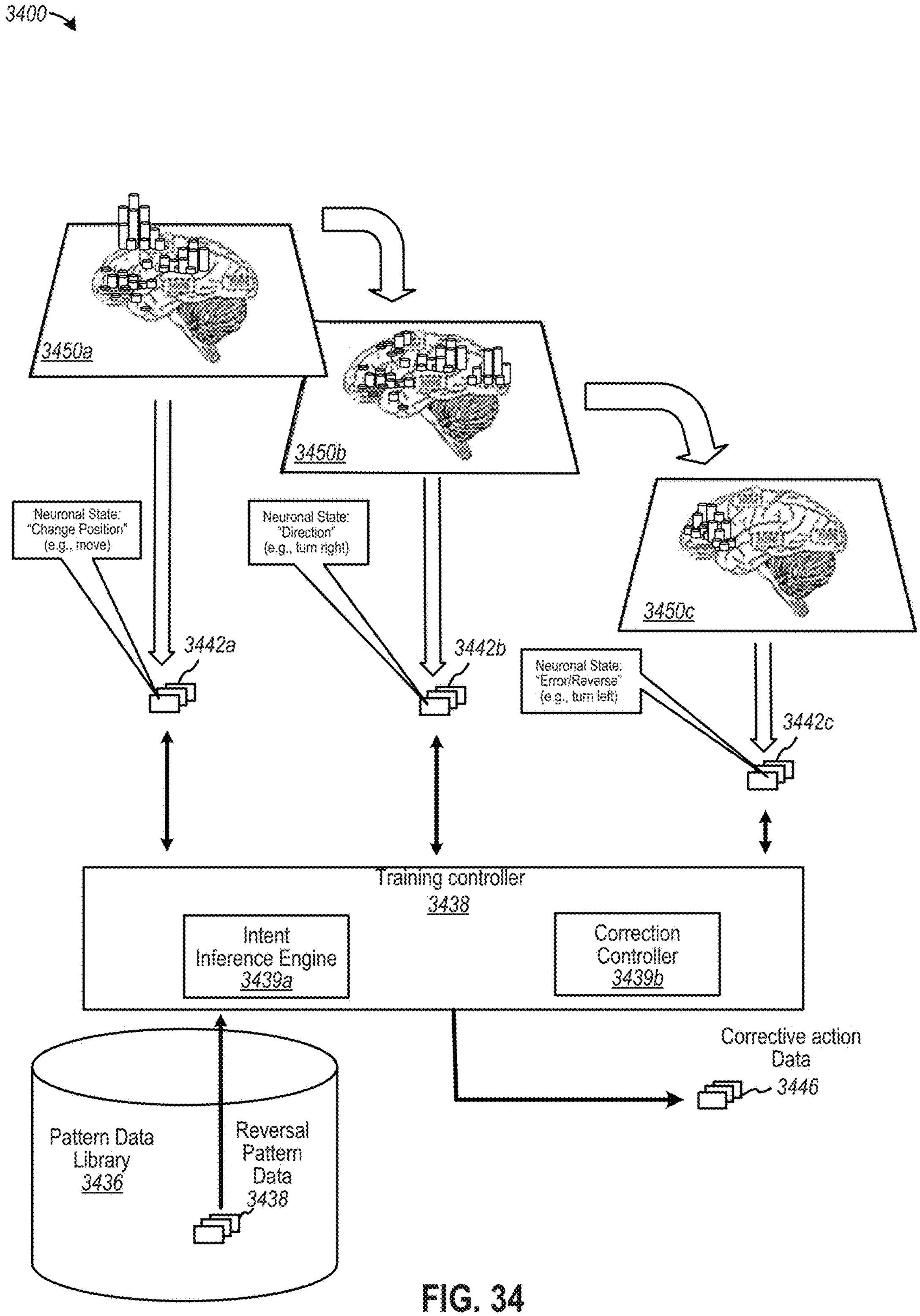
FIG. 34 is a diagram depicting an example of a training controller configured to derive pattern data to detect desired corrective action, according to some examples.

FIG. 34 is a diagram depicting an example of a training controller configured to derive pattern data to detect desired corrective action, according to some examples. Diagram 3400 includes a training controller 3438 configured to identify patterns of sensed neuronal activity data that correlate to neuronal states associated with a thought relating to an "error" and/or an intent to "correct" the error. Upon identifying, pattern data associated with a central nervous system indicating an "error," training controller 3438 can generate corrective action data 3446 with which a physiological activity controller (not shown) may implement to correct the detected patterns indicating an error. According to some examples, elements depicted in diagram 3400 of FIG. 34 may include structures and/or functions as similarly-named or similarly-numbered elements depicted in other drawings.

To illustrate operation of training controller 3438, consider that training controller 3438 receives sets of training data 3450*a*, 3450*b*, and 3450*c*, which may be derived or sensed using an array of neuronal activity sensors (not shown). Further, training data sets 3450*a*, 3450*b*, and 3450*c* may be associated with neuronal state (or intent) data 3442*a* to "change position," neuronal state (or intent) data 3442*b* to specify a "direction" (e.g., turn right), and neuronal state (or intent) data 3442*c* to "reverse" a prior action, neuronal state, or intent.

Training controller 3438 may include an intent inference engine 3439*a* and correction controller 3439*b* coupled to pattern data library 3336, which may include reversal pattern data 3338. Intent inference engine 3439*a* may be configured to analyze neuronal state data 3442*a* and 3442*b* to identify reversal pattern data 3338, which identifies an error, if any, based on the spatiotemporal relationship of neuronal state data 3442*a* and 3442*b*. Upon detecting neuronal state data 3442*c*, which specifies an occurrence of an error, training controller 3438 may identify a match between sensed data 3442*c* and reversal pattern data 3338. In response, correction controller 3439*b* may be configured to identify corrective action data 3446 that may be applied to, for example, an application controller (not shown) to cause the error to be reversed. Corrective action data 3446 may include data specifying an action to "turn left" to replace the erroneous action to "turn right." Note that the generation of patterns to detect errors based on sensed neuronal activity is not limited to the above, which is but one example of detecting errors and taking corrective action using a human-machine interface.

Figure 35:
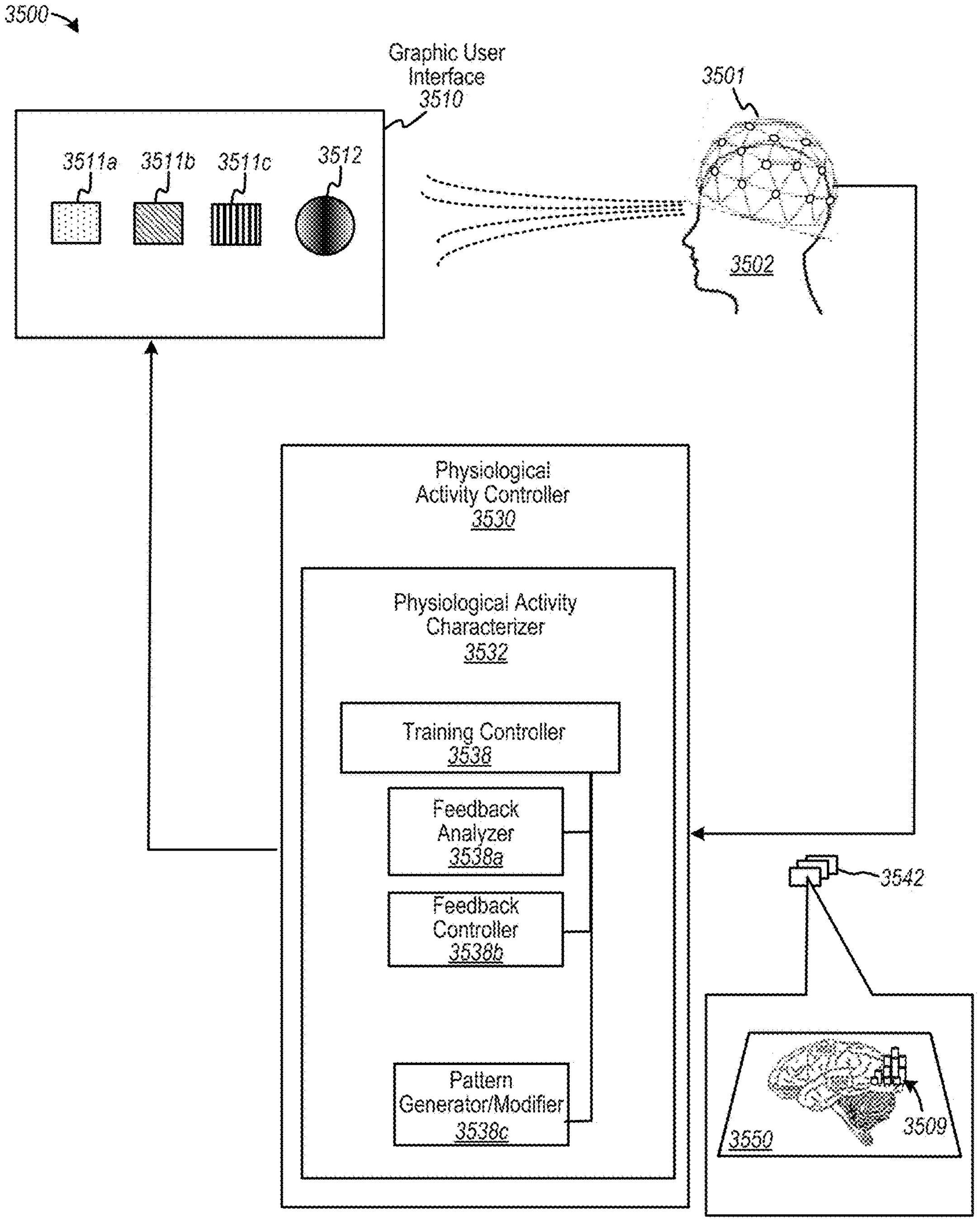
FIG. 35 is a diagram depicting a physiological activity controller in accordance to some examples.

FIG. 35 is a diagram depicting a physiological activity controller in accordance to some examples. Diagram 3500 includes a physiological activity controller 3530 that includes a physiological activity characterizer 3532. In turn, physiological activity characterizer 3532 may include a training controller 3538, a feedback analyzer 3538*a*, a feedback controller 3538*b*, and a pattern generator/modifier 3538*c*. Further to diagram 3500, physiological activity controller 3530 is coupled to a graphic user interface 3510 to provide, for example, visually-related stimuli to activate portions of a visual cortex, whereby the visually-related stimuli may be relatively specialized enhancing sensing neuronal activity data at that brain portion. Physiological activity controller 3530 also is coupled to an array of neuronal activity sensors 3501 configured to detect neuronal activity sensor data 3542 from a user 3502. Training controller 3538 may have generated pattern data 3550, which may include data patterns 3509 that emphasize or weight more heavily neuronal activity at a visual cortex relative to other portions of the brain. According to some examples, elements depicted in diagram 3500 of FIG. 35 may include structures and/or functions as similarly-named or similarly-numbered elements depicted in other drawings.

According to some embodiments, feedback controller 3538*b* may be configured to control the generation of stimuli to present to user 3502, whereby the characteristics of each of the stimuli may be selected to generate optimized or distinctive (e.g., optimally distinguishable) neuronal brain activity patterns at any portion of the brain. In the example shown, feedback controller 3538*b* is configured to generate icon images 3511*a*, 3511*b*, 3511*c*, and 3512 for display the graphical user interface 3510, each of which is generated to generate optimally distinguishable patterns of brain activity at the visual cortex, among other portions of the brain, such as the cerebral cortex. In this example, icon images 3511*a*, 3511*b*, 3511*c*, and 3512 may be associated with interface intents to navigate "up," "down," "right," and "left." So if user 3502 focuses attention on icon image 3512, then physiological activity controller 3530 can detect neuronal activity associated with navigating "to the left." In response, physiological activity controller 3530 may generate control data to cause navigation of an item to the left on graphical user interface 3510. Note that graphic user interface 3510, as a sensory feedback device, may be implemented in 2D or 3D, or as a wearable head-mounted display. Or, display 3510 may be replaced with a haptic feedback system, among other sensory feedback devices. Feedback controller 3538*b*, as well as other elements depicted in FIG. 35, may be implemented as a microprocessor control unit or any other processor configured to determine which images to present or to perform 3D modeling.

Graphical user interface 3510, as a screen display, may display any number of images. A physiological activity correlator (not shown) may be configured to detect patterns of activity indicating the image or the position of icon image 3512. Physiological activity controller 3530 then may select icon image 3512. In some examples, particular patterns of light received onto the retina may cause different patterns of central nervous system activity within or in relation to the visual cortex. So, by detecting central nervous system activity related to the visual cortex, physiological activity controller 3530 may correlate more prominent patterns (e.g., patterns associated with sensed stimuli via the eyes) of icon images 3511*a* to 3512 to determine which icon image is the focus of the user's attention (e.g., icon image 3512). Alternatively, by detecting the position of the focus of attention (e.g., by using eye tracking or otherwise determining user's gaze), physiological activity controller 3530 may be configured to select the position of an image that is at the focus of the user's attention.

A variety of different feedback devices and techniques may be implemented, according to various examples. In some examples, graphical user interface 3510 may be configured to provide an immersive display as a game controller, a data visualization controller to manipulate financial data, a typing system or drawing system to electronically model and manipulate structures and processes, etc. In some cases, eye-tracking may be implemented to enhance the identification of an object of focus attention (e.g., by using electrooculography, or "EOG," among other techniques). Further, visual data may be presented in accordance with various visual characteristics, such as presenting data in a manner tailored to the affordances of the retina, or presenting imagery with specific spatial frequencies, horizon and/or vertical motion, with or without color, with masking, at different speeds and directions, and the like. In some cases, visual data may be configured tailored to affordances associated with the retina, visual cortex and/or central nervous system (as a whole), whereby an affordance may represent a relationship (e.g., in pattern data) between a perceived object, as a stimulus, and an organism's ability to perform an action.

Figure 36:
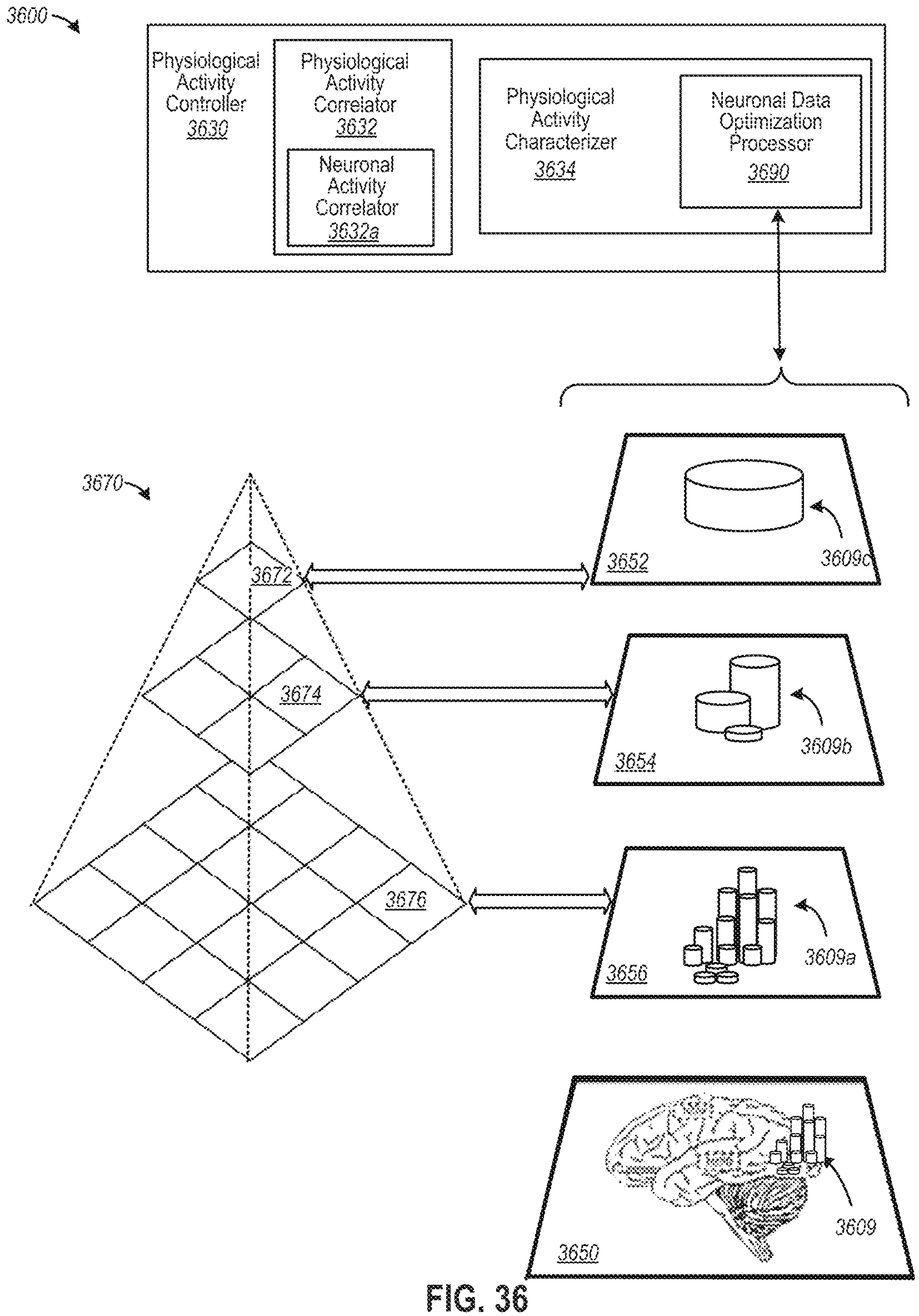
FIG. 36 is a diagram depicting a physiological activity controller including a neuronal data optimization processor, according to some examples.

FIG. 36 is a diagram depicting a physiological activity controller including a neuronal data optimization processor, according to some examples. Diagram 3600 depicts a physiological activity controller 3630 including a physiological activity correlator 3632, which, in turn, includes a neuronal activity correlator 3632*a*, and a physiological activity characterizer 3634, which is shown to include a neuronal data optimization processor 3690. Neuronal data optimization processor 3690 may be configured to generate different representations of patterned neuronal activity data at multiple scales and levels of resolutions. Further, physiological activity controller 3630 may also be configured to format sensed neuronal activity data (e.g., as sensed by an array of neuronal activity sensors, such as bio-inductance sensors) at different levels of resolution to, for example, effectively and efficiently transmit sensed data and matching against pattern data.

In the example shown, consider that sensed neuronal activity data 3650 includes a portion of neuronal activity data 3609 at, for example, a relatively high or fine resolution. In generating patterns, physiological activity characterizer 3634 and/or neuronal data optimization processor 3690 may be configured to form different subsets of pattern data at different resolutions. For example, a subset of pattern data 3656 may include patterns of, for example, action potential values 3609*a* at relatively high levels of resolution. Pyramid representation 3670 presents an example of a multi-scale representation at different scales (e.g., resolutions), whereby the lowest level 3676 is related to pattern data 3656 of fine resolution. A subset of pattern data 3654 may include patterns of action potential values 3609*b* at intermediate levels of resolution. Pyramid representation 3670 depicts an intermediate level 3674 being associated with pattern data 3654. Further, a subset of pattern data 3652 may include patterns of action potential value(s) 3609*c* at a relatively low level of resolution. Pyramid representation 3670 depicts a lowest level 3674 being associated with pattern data 3652. In some examples, pyramid representation 3670 depicts different layers relate to different transformed versions of neuronal activity in two dimensional arrays.

Figure 37:
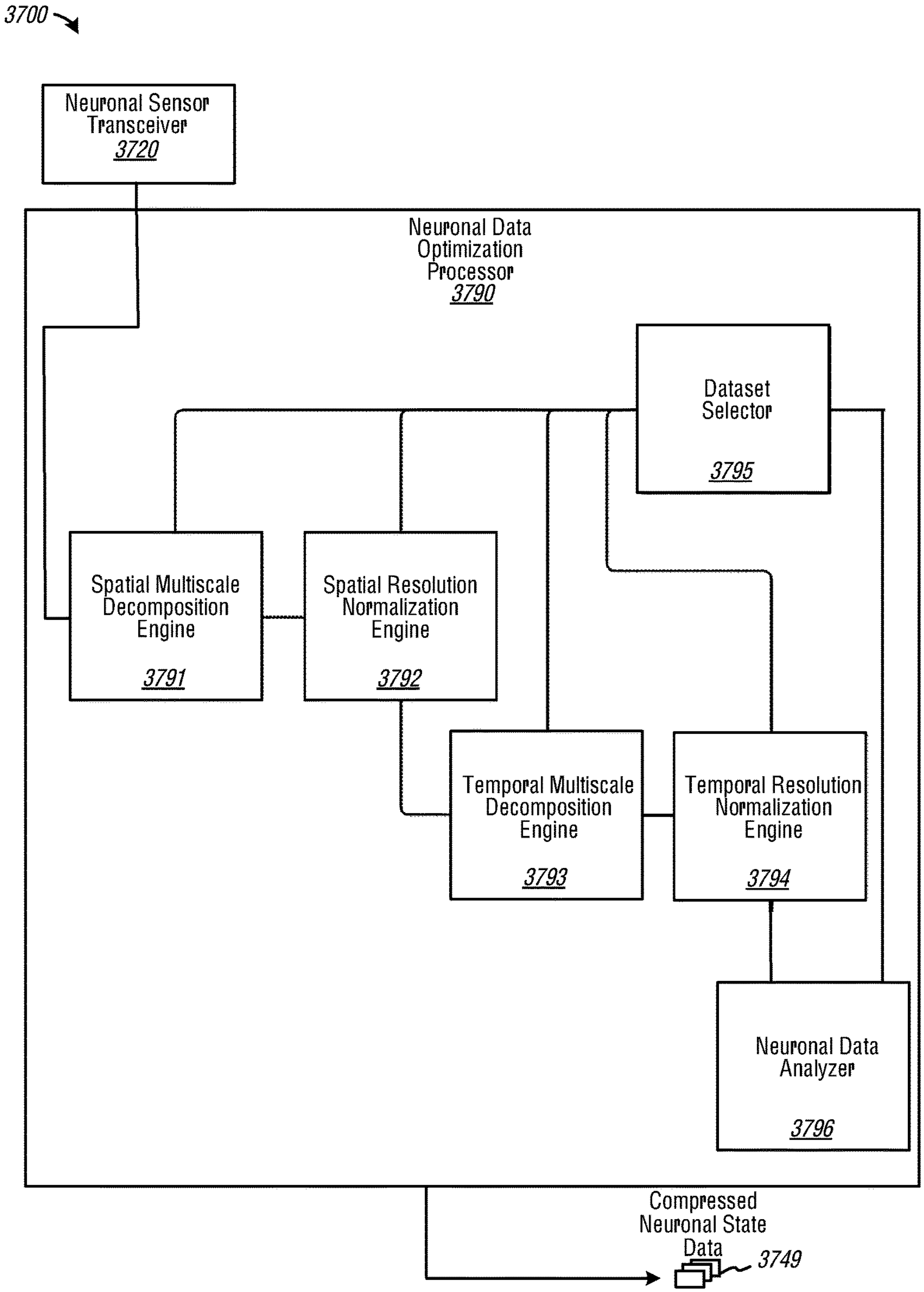
FIG. 37 is a diagram depicting an example of a neuronal data optimization processor, according to some examples.

FIG. 37 is a diagram depicting an example of a neuronal data optimization processor, according to some examples. Diagram 3700 depicts a neuronal state optimization processor 3790 coupled to a neuronal sensor transceiver 3720 to receive sensor data (e.g., neuronal activity data), whereby neuronal state optimization processor 3790 may be configured to generate a compressed (or a data-reduced) version of neuronal state data 3749, whether as received into a physiological activity controller (not shown) as sensed data or as pattern data. According to some examples, elements depicted in diagram 3700 of FIG. 37 may include structures and/or functions as similarly-named or similarly-numbered elements depicted in other drawings. As shown in FIG. 37, neuronal data optimization processor 3790 includes a spatial multi-scale decomposition engine 3791, a spatial resolution normalization engine 3792, a data selector 3795, a temporal multi-scale decomposition engine 3793, a temporal resolution normalization engine 3794, and a neuronal data analyzer 3796.

In some examples, an array of data produced by neuronal activity sensors may be decomposed or transformed at spatial multi-scale decomposition engine 3791 into some space, such as a 2D uniform rectangular array in this example. In other examples, the transform space may be in 2D or 3D, may be uniform or non-uniform, and may be formed using any number of transforms on the data. In some examples, 2D, 3D, and/or 4D wavelet transformation operations may be performed on the neuronal activity data to form, for instance, multiple scales of spatiotemporal neuronal activity data. In at least some examples, neuronal activity data signals may be decomposed into action potentials, for example, in a windowed and/or overlapping format. The decomposition or transformation of the data may be performed by either a neuronal sensor transceiver (not shown) or a physiological activity controller (e.g., at spatial multi-scale decomposition engine 3791), or both. Further, spatial multi-scale decomposition engine 3791 may be configured to generate subsets or copies of subsets of neuronal activity data. In one example, spatial multi-scale decomposition engine 3791 may be configured to generate sets of contiguous data points having side-lengths of, for example, 2, 3, 4, etc. up to a maximum size of an array. In other examples, spatial multi-scale decomposition engine 3791 may be configured to produce subsets of data by, for example, providing sets that do not overlap. Or, spatial multi-scale decomposition engine 3791 may be configured to produce data that may be non-contiguous by, for example, skipping every other, 2nd, 4th, etc.

Spatial resolution normalization engine 3792 and temporal resolution normalization engine 3794 may be configured to ensure that a produced set of spatial and temporal data, respectively, has the same number of elements. For example, the elements may be formed by averaging elements, thereby removing elements or otherwise transforming sets so that the sets of data have a similar number of elements. When a relatively large set is reduced to a smaller set (e.g., by averaging data values), the resolution may be reduced. That is, a new set may be formed having a coarser view of the data, while sets that are not reduced may be viewed as being of at finer resolutions. In some cases, the resolution may be increased by upsampling or other similar techniques. In a specific example, temporal resolution normalization engine 3794 may be configured to generate a same number of samples points in each, for example, by averaging data values.

Temporal multi-scale decomposition engine 3793 may be configured to perform similar, but relative to time, as spatial multi-scale decomposition engine 3791. For a given number of time slices of data, temporal multi-scale decomposition engine 3793 may produce datasets that may be contiguous and may be composed of 2, 3, 4, . . . samples long.

In accordance with some examples, spatial multi-scale decomposition engine 3791 and temporal multi-scale decomposition engine 3793 may be implemented as a set of buffer amplifiers with an appropriate amount of fan-outs, or as any other circuit or structure. Spatial resolution normalization engine 3792 and temporal resolution normalization engine 3794 each may be implemented, for example, using low-pass filtering. According to some examples, spatial resolution normalization engine 3792 and temporal resolution normalization engine 3794 may be implemented by the execution of executable instructions on one or more microcontrollers, graphics processing units ("GPUs"), digital signal processors ("DSPs"), field programmable arrays ("FPGAs"), application-specific integrated circuits ("ASICs"), of the like. According to some examples, feature extraction and analysis may be performed on generated sets of data so as to produce features at multiple scales and resolutions. For example, to implementation of wavelet transforms may be used to efficiently generate the sets of data.

Dataset selector 3795 may be configured to reduce a number of sets that, from moment-to-moment, that may be processed, whereby dataset selector 3795 may be configured to select datasets to include or eliminate from processing. As an example, a switch may be configured to turn off buffer amplifiers, or a code-activated switch may be configured to turn on or off at least a portion of the processing being performed by executable instructions. A dataset selection switch may use any number a number of inputs, and, for example, may use current value(s) of certain datasets to determine which datasets may be processed in a near future.

According to various examples, processing on multiple scales using prioritized regions may be implemented to reduce or cull processing of regions of lower priority. Also, coarser resolution may be used to prioritize finer resolution regions in accordance to a degree of activity or a degree of relevance to other activity types of interest. Processing datasets may be prioritized at any region depending on an expected importance of the region during a time interval, based on a form of the current activity or the likelihood that regions may be active soon (e.g., based on neighboring regions, well-connected regions (based on previous data), and regions that appear on an activation pathway for events of interest. A type of processing may be prioritized to extract features in association with regions based on causally-correlated features, causally-correlated features that relate to events of interest. Note further that matching prioritization to features of a central nervous system to process data by, for example, prioritizing processing of regions with timing dependent on propagation speed of a central nervous system activity, or deprioritizing the processing for regions in recovery.

Furthermore, dataset selector 3795 may be configured to similarly implement any number of the following processing strategies: (1.) for datasets at coarser resolution that contain a certain degree or type of activity, enable processing of datasets at finer resolution using the same data, (2.) for datasets at coarser resolution that include a certain degree or type of activity, disable processing of datasets at finer resolution using the same data, (3.) for datasets at finer resolution that include a certain degree or type of activity, then enable or display processing of datasets at coarser resolutions using the same data, (4.) for datasets that are currently active, enable neighboring datasets, and (5.) for datasets that are currently active, enable datasets whose activity may often be correlated with those datasets that correspond to regions at which neuronal activity is likely to occur, whereby the datasets associated with the activity may be prioritized to correspond to regions where a particular type of activity which is currently being sensed in accordance with the priority.

Neuronal data analyzer 3796 may be configured to determine a type of analysis of processing apply to each dataset. In example, the same processing may be performed on each set (e.g., on predominant numbers of features). In other examples, neuronal data analyzer 3796 may be configured to select a subset of analysis or modify processing parameters, such as modifying a filter length, thresholds, etc., to optimize processing of a number of datasets. When no activity is present in a dataset, neuronal data analyzer 3796 may be configured to detect activity, and once activity is detected, neuronal data analyzer 3796 may be configured to determine a type of activity, or additional features to be enabled. Or, when activity is detected in one dataset, neuronal data analyzer 3796 may implement additional processing on, for example, new features in other datasets correlated with the subject dataset. Therefore, if certain features in one dataset leads to a set of possible features in other datasets, neuronal data analyzer 3796 then may prioritize processing of the other datasets.

Figure 38:
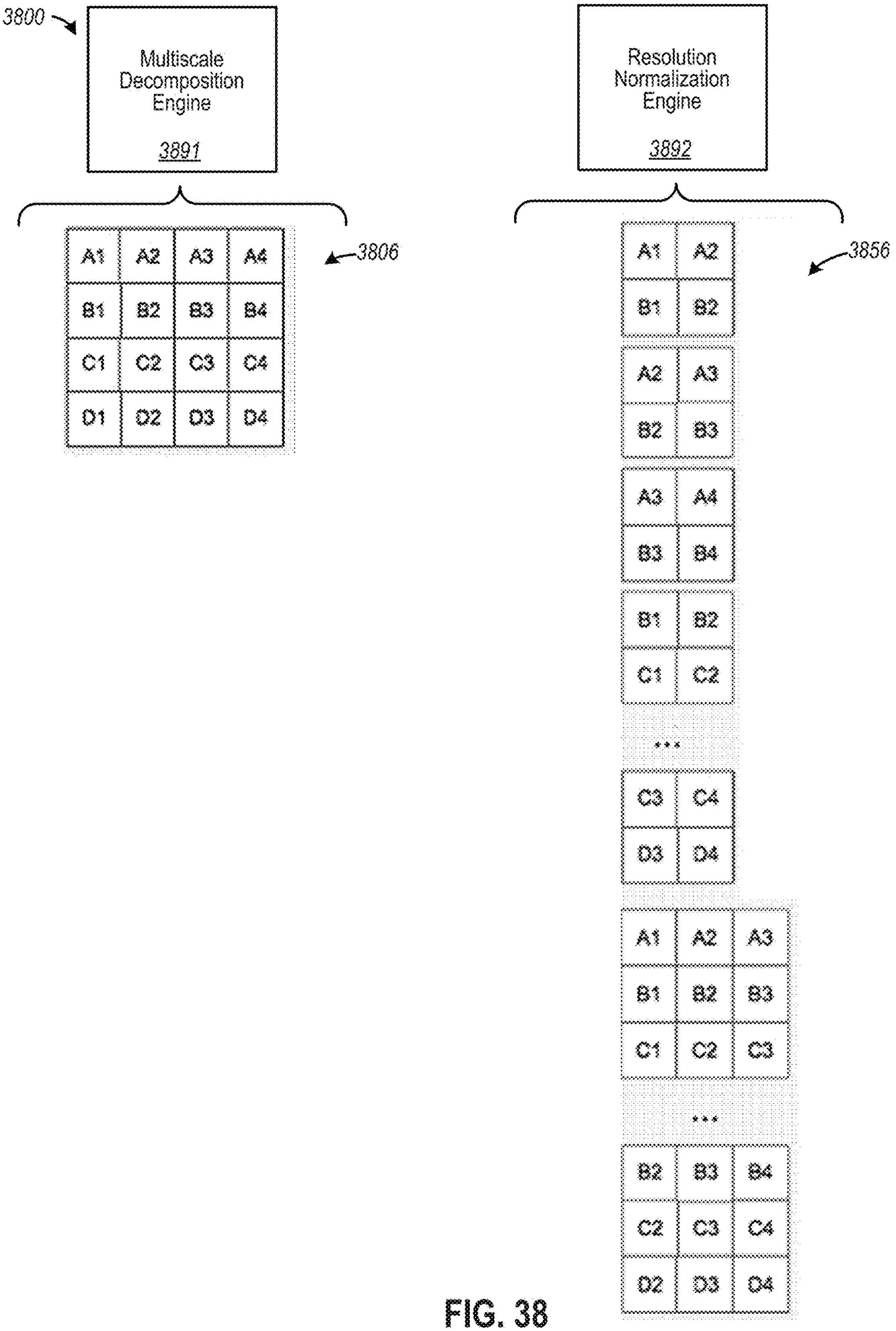
FIG. 38 is a diagram depicting operation of a multiscale decomposition engine and a resolution normalization engine, according to some examples.

FIG. 38 is a diagram depicting operation of a multiscale decomposition engine and a resolution normalization engine, according to some examples. As shown, diagram 3800 includes a multi-scale decomposition engine 3891 configured to generate relatively large data sets 3806, and a resolution normalization engine 3892 configured to generate relatively smaller data sets 3856. While there may be a larger number of sets, each set may contain fewer elements. Further, it may be more efficient to process smaller sets 3856 than large sets 3806. According to some examples, a smaller set 3856 may include sufficient information as larger set 3806 in multiple, different combinations. Thus, patterns occurring in larger sets 3806 may be determined by combinations of patterns occurring in smaller sets 3856.

Figure 39:
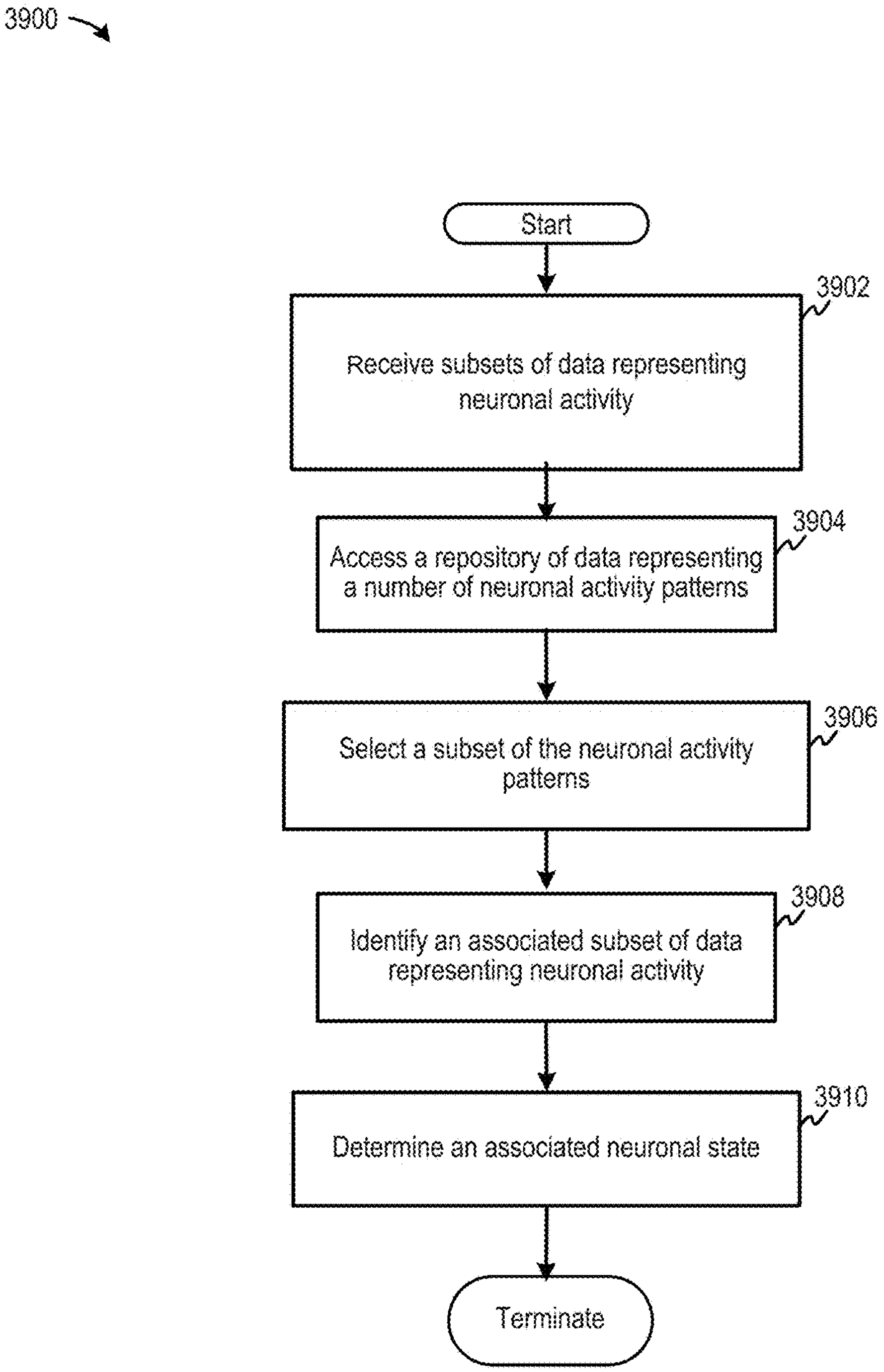
FIG. 39 is an example flow diagram, according to some examples.

FIG. 39 is an example flow diagram, according to some examples. Flow 3900 begins at 3902, at which one or more sensors are configured to generate sensor data, whereby the data is received as subsets of data representing neuronal activity. At 3904, a repository of data representing a number of neuronal activity patterns may be accessed. At 3906, a subset of the neuronal activity patterns may be selected, and an associated subset of data representing neuronal activity may be identified at 3908. At 3910, and associated neuronal state may be determined, whereby neuronal state may be related to, or associated with, an "intent," "command," "emotion," or "thought," based on detected neuronal activity.

Figure 40:
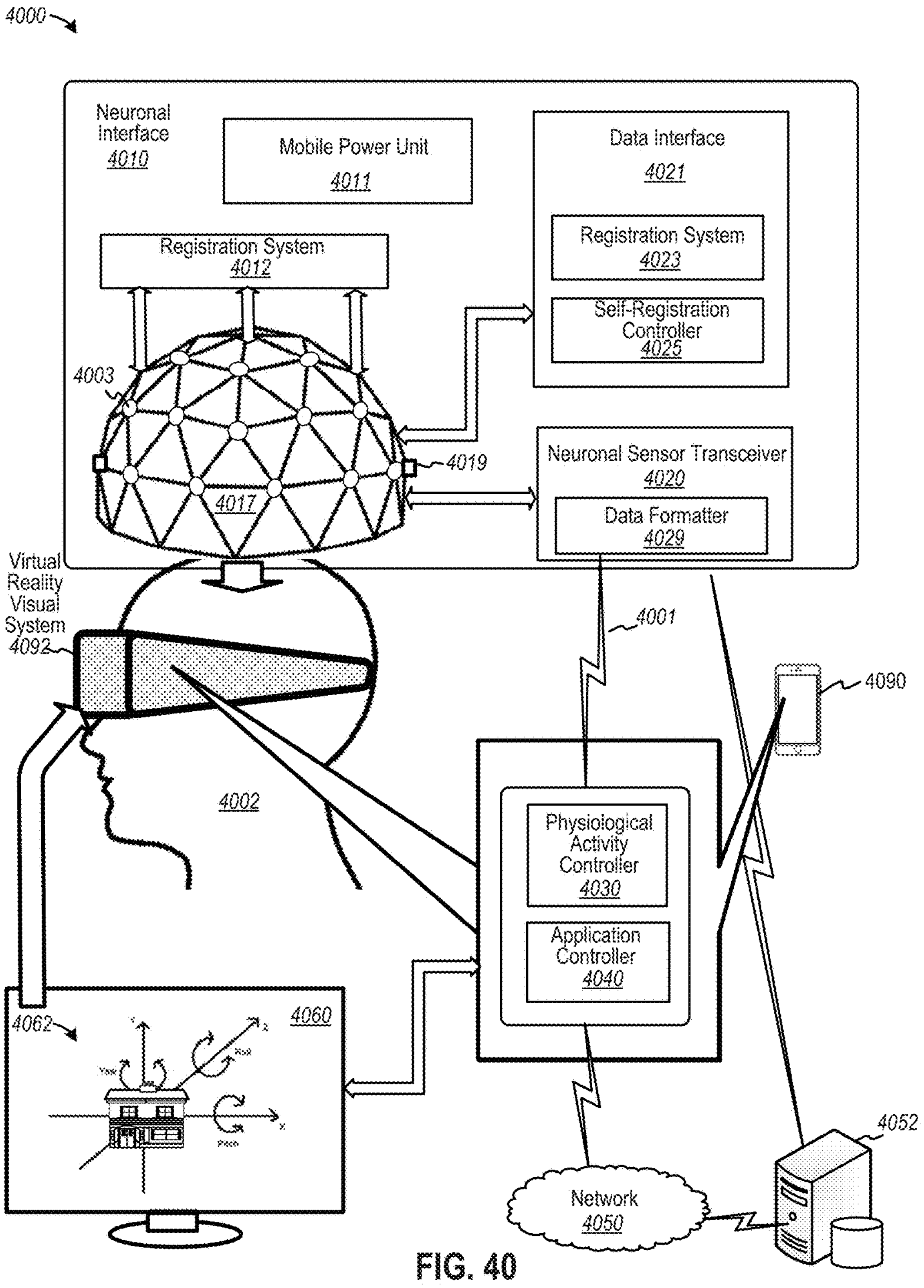
FIG. 40 is a diagram depicting an example of a neuronal interface to identify neuronal states for facilitating a human-machine interface, according to some embodiments.

FIG. 40 is a diagram depicting an example of a neuronal interface to identify neuronal states for facilitating a human-machine interface, according to some embodiments. Diagram 4000 depicts a neuronal interface 4010 configured to adapt an array of physical activity sensors 4017, including neuronal activity sensors, either physically or electrically, or both, to sense neuronal activity of a central nervous system of an organism 4002. Neuronal interface 4010 is configured to detect an orientation or an arrangement of an array of neuronal activity sensors 4017 relative to one or more reference points on, or in, a head of organism 4002, and is further configured to compensate for displacement of one or more neuronal activity sensors in array of sensors 4017. Neuronal interface 4010 also is configured to detect signals emanating from a central nervous system of organism 4002, the signals being representative of neuronal activity associated with one or more neuronal states. Neuronal interface 4010 facilitates in-situ neuronal state determination, and, thus, may be implemented a wearable device, such as in (or as) a hat, headband, or any accessory or garment that may be positioned adjacent any portion of a central nervous system, such as a brain or any other nervous system component in an organism (e.g., may be disposed at or adjacent nervous system components in an arm, leg, or any other portion of a body). In some examples, neuronal interface 110 may be disposed off-body.

Neuronal interface 4010 is shown to include a first registration system 4012, a neuronal sensor transceiver 4020, a data interface 4021, and a mobile power unit 4011, which may be a battery or other source of power. Registration system 4012 may be configured to position a relatively large number of electrodes to contact a scalp with sufficient contact, or to position a relatively large number of magnetic coils in close proximity to a scalp, at least over a relatively small degree of curvature. Registration system 4012 may be configured to mechanically deform or physically adapt array of neuronal activity sensors 4017 to conform to fit a head of wearer 4002. In some examples, registration system 4012 may include a system of ball joints and springs that may selectable deform or adjust portions of array of neuronal activity sensors 4017 to fit a head of a user. Any type of known mechanical systems may be implemented to adjust the fit of array of neuronal activity sensors 4017 so as to, for example, optimize positions of sensors 4003 to provide optimal contact and/or positioning of subsets of neuronal activity sensors 4003. In some cases, one or more bands (not shown) implemented as one or more portions of a periphery of array 4017 may be configured to incrementally tighten so as to adjust fit to the physical dimensions of the user's head. According to some embodiments, neuronal activity sensors 4003 may include one or more "bio-inductance" sensors, as well as any other suitable sensor.

Data interface 4021 is shown to include a second registration system 4023 and a self-registration controller 4025, and may be configured to detect an orientation or arrangement of an array of neuronal activity sensors 4017 relative to one or more reference points (e.g., at, on, or in a head of a user), and may be further configured to automatically self-register the array relative to, for example, one or more internal biological structures under a surface of the skin to compensate for displacement of one or more neuronal activity sensors 4003 due to, for example, movement of array of neuronal activity sensors 4017 during use.

Registration system 4023 may be configured to determine an orientation or arrangement of an array of neuronal activity sensors 4017 relative to biological structures of a head of organism 4002, such as subcutaneous structures of bone tissue (e.g., portion of a skull), vascular structures, neuronal or central nervous system structures, and the like. In some examples, registration system 4023 includes logic (e.g., hardware and/or executable instructions) that is configured to determine contours and physical features of a brain. As such, registration system 4023 may be configured to activate arrays or sub-arrays of neuronal activity sensors 4017 (e.g., arrays or sub-arrays of bio-inductance sensors) to detect ridges (e.g., gyri) and depressions (e.g., sulci) of the folds on the surface of a brain. The location of bridges and depressions of a brain may be used as reference points with which to calibrate an orientation of array 4017. Thus, registration system 4023 may be configured to characterize distributions of white and gray matter in an individual's head to pick up a basic or generalized shapes of the head (or the distribution of brain matter) to calibrate orientation of neuronal interface 4010 and its arrays of neuronal activity sensors.

Self-registration controller 4025 may be configured to self-register array of sensors 4017 to automatically re-align or adapt functionalities of neuronal activity sensors 4003 relative to amounts of disposition of sensors 4003. For example, a first subset of neuronal activity sensors 4003 may be configured to sense neuronal activity related to a visual cortex, but if the array of sensors are moved (e.g., the array of sensors are rotated about the user's head), then self-registration controller 4025 may be configured to identify a second subset of neuronal activity sensors 4003 for selection to sense neuronal activity of the visual cortex. In some examples, one or more motion sensors 4019, such as accelerometers, gyroscopes, optical sensors, etc., may be implemented as part of array 4017 to detect relative motion, and, for example, changes in position of one or more sensors 4003. Based on detected or derived amounts of displacement, self-registration controller 4025 may be configured to self-register array 4017 of neuronal activity sensors 4003. Further, self-registration controller 4025 may be configured to urge registration system 4023 to re-determine contours and physical features of a brain so as to compensate for relative amounts of displacement of array 4017. Therefore, self-registration controller 4025 provides an ability for neuronal interface 4010 to ensure portions of an array 4017 are appropriately disposed at or adjacent portions of a brain (e.g., an auditory cortex, a motor cortex, the cerebral cortex, etc.) to sense certain neuronal activities of interest.

Neuronal sensor transceiver 4020 is shown to include a data formatter 4029, according to some examples. Neuronal sensor transceiver 4020 is configured to apply stimulus signals to array 4017 and to receive response signals that include data or information indicative to an amount of neuronal activity elements (e.g., an amount of action potentials) from one or more portion of a brain. In some examples, data formatter 4029 is configured to format data for transmission or exchanged via communications link 4001 to, for example, a physiological activity controller 4030 and/or an application controller 4040. Data formatter 4029, the use of which may be optional, can be implemented to reduce amounts of data transferred via link 4001. For example, data formatter 4029 may be able to form near-field types of communication, and may also perform data compression and feature extraction, as well as any other data reduction techniques for optimizing transmission of data relating to neuronal activities for purposes of determining one or more neuronal states. According to various examples, data formatter 4029 may be configured to implement cache-and-burst communication techniques, wireless radio protocols of relatively high bandwidth (e.g., via ultra-wideband, or "UWB," communication links, etc.), data compression (e.g., JPEG, Motion JPEG, etc.), feature extraction and off-load, short-range repeater technologies and devices, etc.

Physiological activity controller 4030 may be configured to receive physiological activity data, including neuronal activity data from array 4017, and to determine one or more neuronal states associated with, for example, an intent, a thought, an emotion, or a command, associated with a central nervous system of an organism. Physiological activity controller 4030 may be further configured to transmit data representing one or more neuronal states (e.g., defining an intent, thought, or command) to application processor 4040, which, in turn, may be configured to map one or more intents, thoughts, or commands to a function of a particular interface or application, such as a text editor application. Therefore, application processor 4040 can generate command data 4046 suitable for the text editor application. Examples of command data 4046 may include interface commands to navigate an interface (e.g., user interface commands such as up, down, left, right, pan, zoom, etc.). Other examples of command data 4046 may include application-specific commands (e.g., identifying a word and performing an "insert" word operation, a back space command, select text command, text formatting commands, etc.). Another example of an application for which command data 4046 is generated includes a computer tomography application configured to build a 3D model of activity (e.g., neuronal or non-neuronal activities) within the central nervous system. Thus, diagram 4000 depicts examples of various components that may implement a neuronal activity sensing system that facilitates a neuronal-based human-machine interface.

Application controller 4040 may include hardware or software, or both, and may be configured to generate command data 4046 based on identified neuronal activities, as well as identified non-neuronal activities. Examples of command data 4046 data may include instructions (e.g., such as an application programming interface, or API) that invokes a command as a function of detected neuronal or non-neuronal activity. The commands may relate to interface commands, as well as commands or instructions to facilitate communication. In some embodiments, command data 4046 may also include instructions to provide an idea or thought that correlates to a particular type of neuronal activity. Therefore, should an organism be thinking of an automobile having a color "blue," the observation (e.g., a thought or idea) may relate to detectable neuronal characteristics constituting neuronal activity states of "blue" and "automobile." Thus, command data 4046 may specify the command of presenting a "blue automobile" to a user interface (e.g., a graphical user interface, or GUI).

According to some examples, one or more of physiological activity controller 4030 and application controller 4040 (or any portions thereof) may be implemented in a mobile computing device, such as mobile phone 4090, or a virtual-reality visual system 4092 that is configured to present imagery to user 4002 (e.g., with sufficient imagery to provide a perception of immersion). As such, neuronal interface 4010, physiological activity controller 4030, and application controller 4040 may be configured to provide command data to facilitate a human-machine interface with virtual-reality visual system 4092. In the example shown, the identification of one or more neuronal states by physiological activity controller 4030 may cause application controller 4040 to modify an application (e.g., a computer aided drawing, or "CAD" application) that is shown to display the design and manipulation of a 3-D model of a house 4062 on graphical user interface 4060.

According to some embodiments, one or more of neuronal interface 4010, physiological activity controller 4030 and application controller 4040 may be configured to exchange data via any network 4050 to a remote server and/or database computing system 4052. According to various examples, subsets of neuronal activity data and other related activity data (e.g., physiological data, contextual data, etc.) of user 4002 may be transferred to remote computing system 4052 for additional analysis and computations. In some examples, computing system 4052 may assist in mapping brain morphology of a new user to a genericized or generalized representation of an aggregate of users. Thus, computing system 4052 may apply multi-user generic detected patterns via calibration to an individual that may yet to be characterized (e.g., to reduce time or resources in adapting neuronal interface 4010 to a specific user of unique physical dimensions and biological structures). Either computing system 4052 or application controller 4040, or both, can be configured to adapt any application to an implementation of a human-machine interface that includes neuronal interface 4010 and physiological activity controller 4030.

Figure 41:
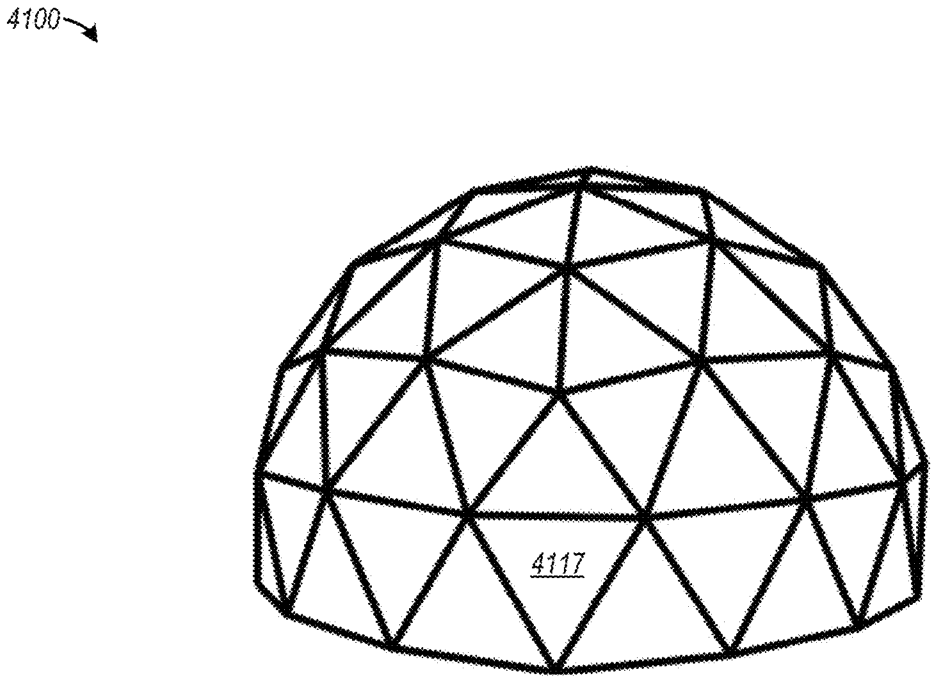
FIG. 41 depicts an example of an array of neuronal activity sensors, according to some examples.

FIG. 41 depicts an example of an array of neuronal activity sensors, according to some examples. Diagram 4100 depicts an array of physiological or neuronal activity sensors 4117 that may be formed in any number of manufacturing processes. In one example, a 3-D scanner may be configured to create a model of a head of a user. A computing device and executable instructions can generate the sensor materials in 2D surface(s) that can conform to a user's head. In one example, a 3D model of a user's head may be formed as a template (e.g., using 3-D printing technologies). The 2D set of materials may be configured to conform about the 3D model (e.g., vacuum holes in the 2-D material may be configured to vacuum-shape the 2-D materials to form a 3-D array, whereby portions of the array may be laser welded to form a closed system. An example technique is to build a 3D printed model of a skull for a user (or for a generic category of user) with a hollow center and air holes dimensioned as vacuum holes. A vacuum then can be applied pulling the material onto the head. In some examples, 2-D materials may include a flex or rigid printed circuit board ("PCB") in which one or more arrays of sensors may be formed on or in association with, for example, optional embedded resistive layers and/or embedded capacitive layers that may be included to reduce component count and system complexity. The resistive and capacitive elements may facilitate various sensing techniques, such as frequency division multiplexing ("FDM") to reduce a number of components used to form array 4017. In such a 3-D modeled array, the array of sensors is customized to fit unique dimensions of the user's head to ensure sensors return to a same position every time (or mostly every time).

Figure 42:
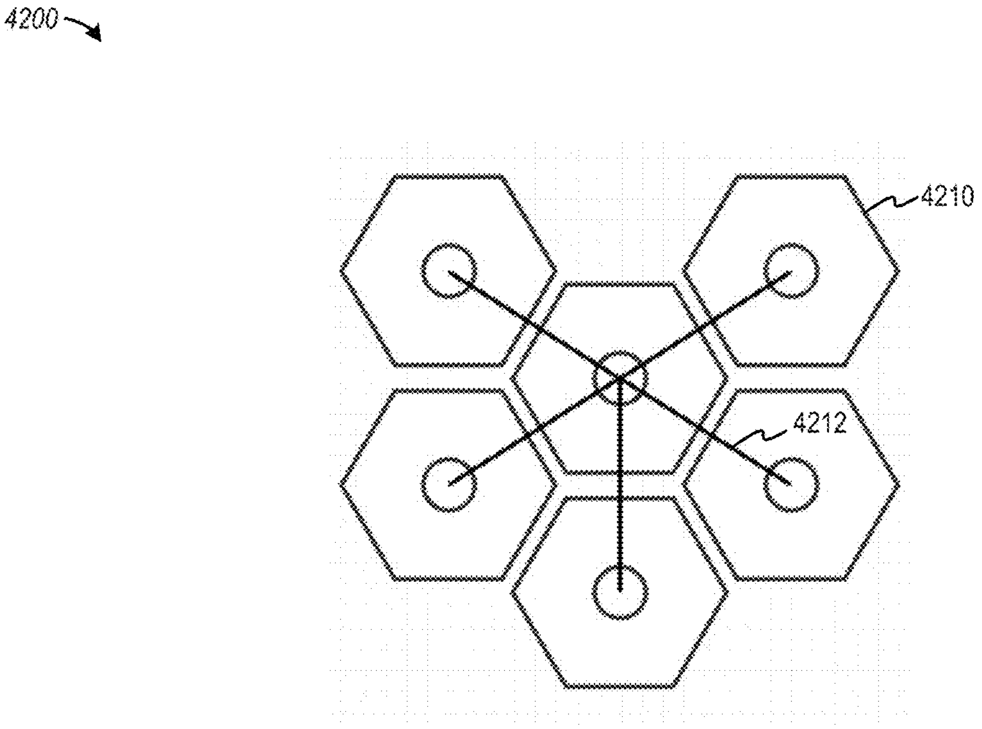
FIG. 42 depicts an example of a portion of an array of neuronal activity sensors, according to some examples.

FIG. 42 depicts an example of a portion of an array of neuronal activity sensors, according to some examples. Diagram 4200 depicts a subarray of sensor elements 4210 that may be used to form a larger array of neuronal activity sensors. An number of modules, each holding array electrodes, may be coupled via a joint 4212 that allows rotation or displacement to a rigid or flexible frame (e.g., to adapt to the curvature of the user's head). Modules of sensors 4210 may be arranged so that they substantially cover a head with a relatively large number of electrodes configured to contact portions of the head with a relative degree of sufficiency. A frame (not shown) may be used to ensure joints 4212 (e.g., in registration system 4012 of FIG. 40) remain relatively rigid to maintain physical conformance to a user's head.

According to some examples, array of neuronal activity sensors 4117 may be implemented by any type of polygonal arrays, such as overlapping polygons or multi-scale polygons in, for example, geodesic arrangements. In some examples, geodesic arrangements may include nested geodesic arrays or sub-arrays. A geodesic arrangement may include any number of registering hexagons, triangles, gores, or any other shape that may facilitate arrangement and a self-registering sensor system. In some examples, hexagonal subarrays may be formed on flexible material, such as a flexible PCB material. Or, each hexagon may be rigid and affixed to flexible material. In some cases, a geodesic arrangement may be permanently fixed or, in some cases, somewhat deformable.

Figure 43:
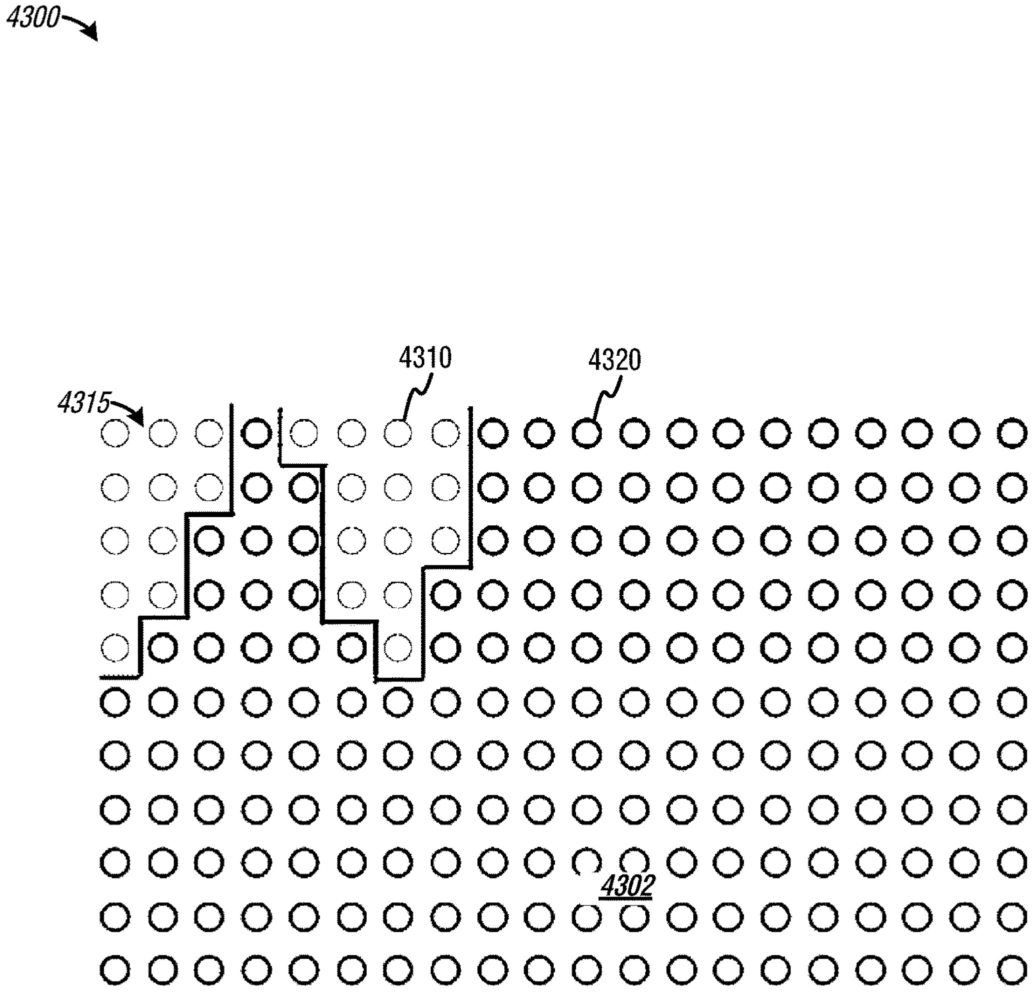
FIG. 43 depicts an example of material used to form a sensor array, according to some examples.

FIG. 43 depicts an example of material used to form a sensor array, according to some examples. Diagram 4300 depicts a two-dimensional ("2D") material 4302 including array of sensors 4320. Material 4302 is shown is as flat sheet of array sensors 4320 that may have portions 4315 of material remove therefrom. Portions 4315 of removed material may be in the form of "gores" (e.g., a sector of a relatively curved surface that may be flattened to a plane surface with little distortion). Opposing edges of these gores 4315 may be drawn together, introducing curvature. Appropriate design of gores 4315 may introduce curvature that closely matches a head of a user. In some cases, gores 4315 may be introduced at appropriate points in material 4302 without affecting connectivity of electrodes 4320 (e.g., provided that gores start at the ends of rows or columns. Note that in some cases, a missing electrode 4310 may have a fixed nominal voltage (e.g. 0V). As such, the above-described circuit formed in material 4302 need not be significantly modified to account for the missing electrodes 4310. The creation of the gores 4315 may useful be performed by laser or die-cutting, for example. Re-joining the edges may be performed by, for example, laser or RF welding, or with the use of adhesive. In some examples, a standard template may be used for a relatively large number of the population, with gores being used to customize arrays of sensors 4320 to individual's physical dimensions.

Figure 44:
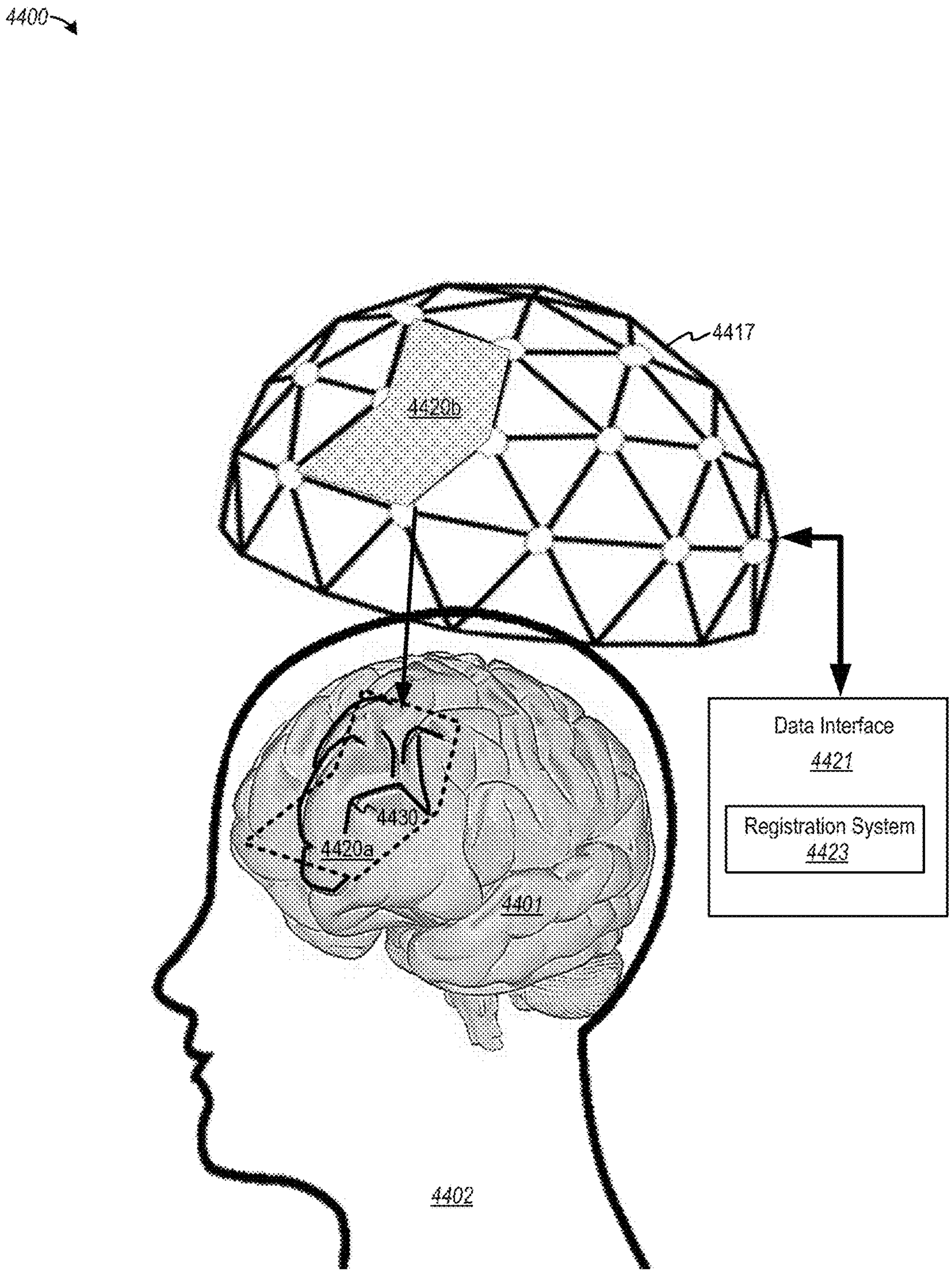
FIG. 44 depicts operation of an example of a registration system, according to some embodiments.

FIG. 44 depicts operation of an example of a registration system, according to some embodiments. Diagram 4400 depicts a registration system 4423 (e.g., optionally associated with data interface 4421) coupled to an array of neuronal activity sensors 4417. According to some examples, elements depicted in diagram 4400 of FIG. 44 may include structures and/or functions as similarly-named or similarly-numbered elements depicted in other drawings. In the example shown, registration system 4423 is configured to activate one or more sensors 4417 to characterize biological components of user 4402, such as ridges 4430 of brain 4401. Further, registration system 4423 is configured to determine a location or region 4420*a* associated with the biological features 4430 (e.g., ridges) that may be used as references for aligning the array of sensors 4417. To illustrate, registration system 4423 may assign a subset 4420*b* of sensors 4417 to calibrate alignment of the array based on biological features in region 4420*a*. One alignment is determined, registration system 4423 may periodically or aperiodically verify whether biological features 4430 are still aligned with subset 4420*b* of sensors 4417. If not, registration system 4423 may recalibrate the alignment by, for example, identifying biological features 4430 and a corresponding next subset of sensors 4417. Thus, registration system 4423 may implement magnetic pick-up sensors and certain frequencies to identify "gross structures" of brain 4401 and locations of other brain portions of interest relative to the location of features 4430.

Figure 45A:
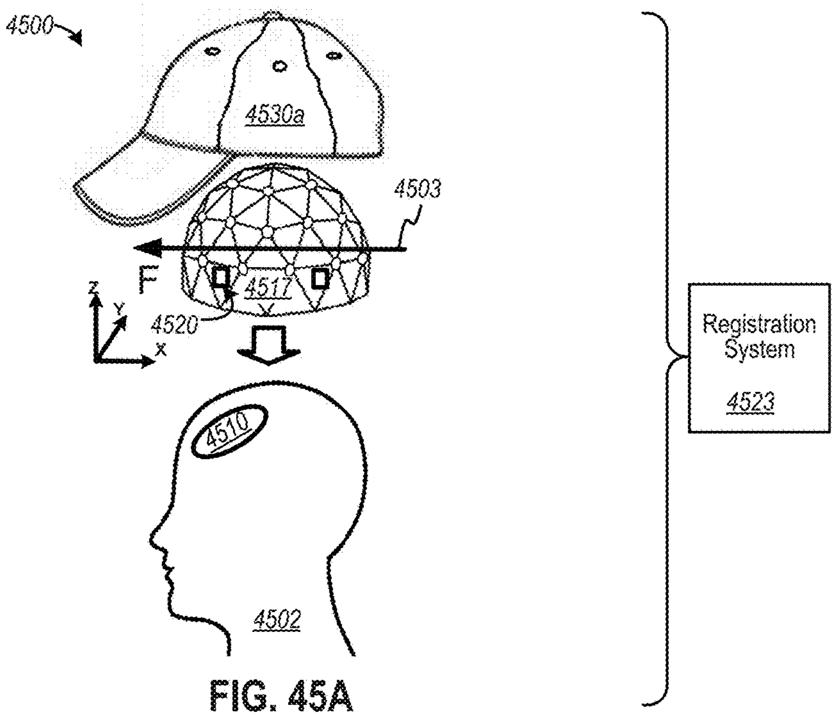
FIGS. 45A and 45B depict an example operation of a self-registration controller, according to some examples.
Figure 45B:
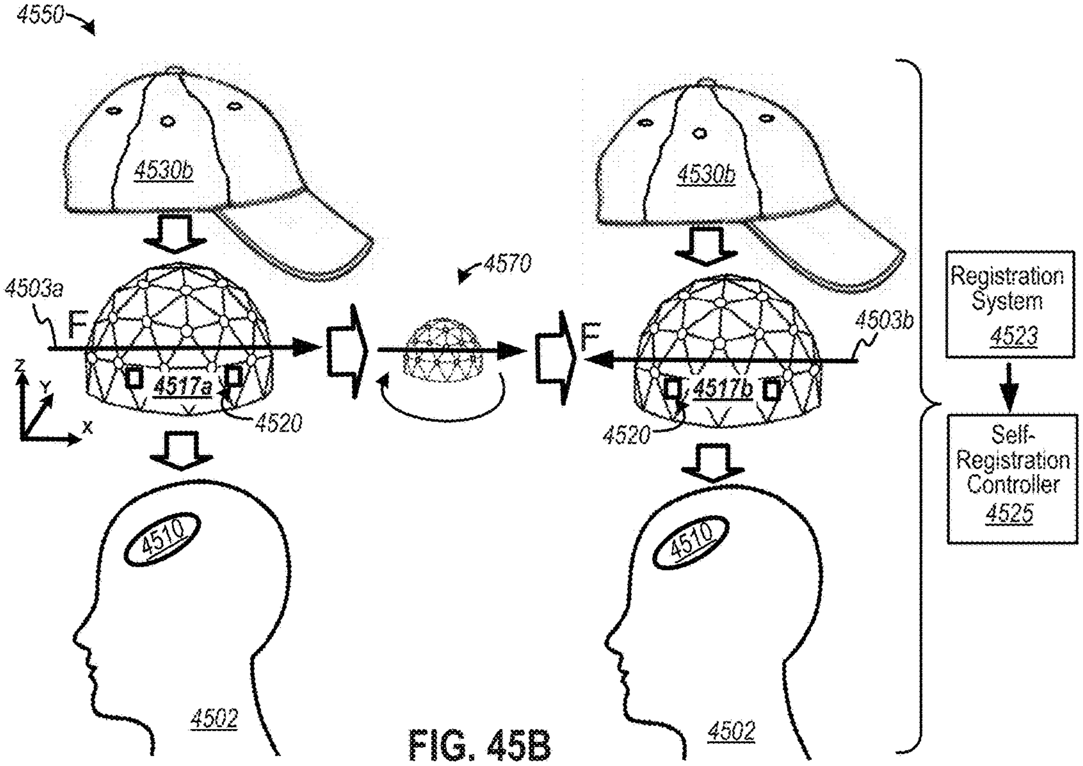

FIGS. 45A and 45B depict an example operation of a self-registration controller, according to some examples. Diagram 4500 of FIG. 45A depicts an array of neuronal activity sensors 4517 implemented as or in a hat 4530*a* and adapted to be worn by user 4502. Registration system 4523 may be configured to determine an alignment of a first direction 4503 of the array of sensors 4517 relative to a position of biological features 4510. The alignment (to the front, "F") may be determined based on bio-inductance sensor data, as well as other sensor data. In this case, array of sensors 4517 may include one or more accelerometers or motion sensors 4520.

FIG. 45B is a diagram 4550 depicting a realignment with array of sensors 4517 subsequent to a displacement of one or more sensors. In the example shown, hat 4530*a* and array of sensors 4517 of FIG. 45A are repositioned and placed in an opposite orientation as hat 4530*b* and array 4517*a* (e.g., when a user turns hat 4530 around). As shown, the initial direction 4503*a* of alignment is now pointing to the rear rather than the front. Registration system 4523 may be configured to re-align direction 4503*a* to match that of direction 4503 of FIG. 45A. Not that the re-aligned direction need not be a physical re-alignment, but rather an electrical re-alignment whereby sensors 4517 are reconfigured based on the portions of a brain, such as relative to biological features 4510. Self-registration controller 4525 may receive or derive relative motion data or displacement data using motion sensors 4520. To facilitate re-alignment, self-registration controller 4525 may be configured to perform a transfer function 4570. Motion sensors 4520 may be used to determine an angle and a distance based on head rotation geometry, as well as to detect movement and data to compensate for such movement. Note that detecting the angle and distance may be perform by other structures or functions and need not be limited to on-body components. Therefore, self-registration controller 4525 may be configured to determine a pre-aligned direction 4503*b* that coincides with direction 4503 of FIG. 45A for purposes of processing sensor data.

In one example, rows and columns of sensors 4517 may be offset to compensate for the movement. For example, a row that might have index 41 in when worn at time, T1, but the index may become index 42 when worn at time, T2. An alternative method is to form a transfer function that transforms data measured at one wearing into data at another. The offset may be calculated by tracking the position of points on the electrode arrays (e.g. with accelerometers, optical sensors, ultrasonic links, etc.) or by use of an optimization function (for example minimizing the difference in a steady-state signal). A number of methods of forming this transfer function are possible. The electrode positions may be tracked by means of accelerometers, optical sensors, ultrasonic links, etc. and a transfer function may be determined algebraically, or a minimization function may be used to form the transfer function that minimizes the difference in the steady-state signal (that may be the average signal over a few seconds or minutes, which may be an initial or subsequent calibration phase or an ongoing recalibration). Or, the optimization function may operate by providing a known stimulus to the user (for example, playing certain imagery, and have the user imagine certain phrases, etc.) and minimizing the difference in a response.

Figure 46:
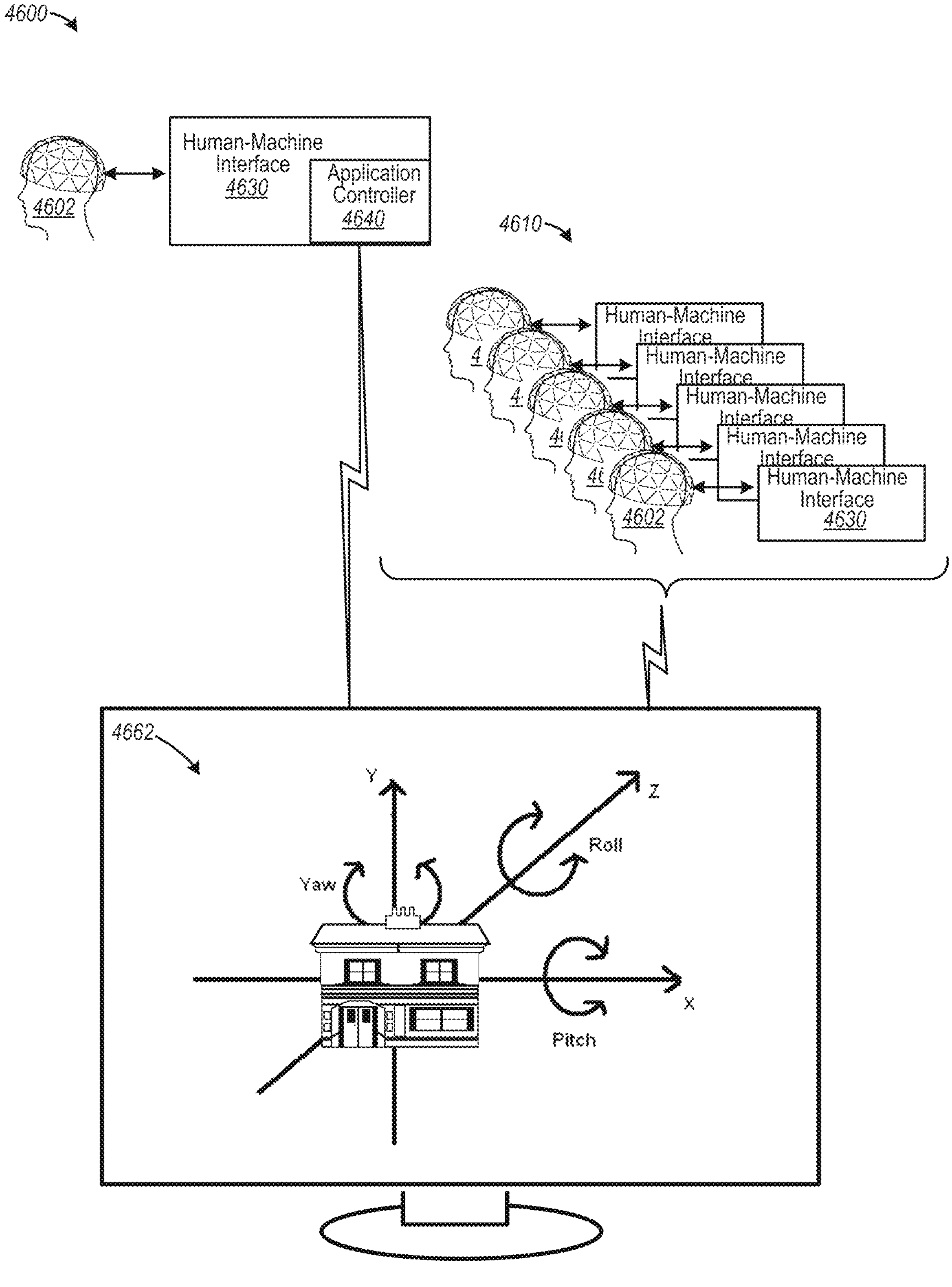
FIG. 46 is a diagram depicting a variety of applications that may interact with a human-machine interface, according to various examples.

FIG. 46 is a diagram depicting a variety of applications that may interact with a human-machine interface, according to various examples. Diagram 4600 depicts a user 4602 implementing a neuronal-based application controller 4640 to facilitate interactions via a human-machine interface 4630 to an application, for example, configured to interact with a graphical interface 4662 to, example, perform architectural design on a building in 3D, whereby sensors of human-machine interface 4630 are configured to detect neuronal activity related to, for example, user 4602 focusing visual attention to a portion of an interface as well as detecting a command associated therewith.

Human-machine interface 4630 may also be configured to interface with financial applications and systems in which financial data may be presented in 3D display, whereby interactions with such 3-D displays may provide provides richer interactions from which information may be obtained. Human-machine interface 4630 may also be configured to interface with videogames and military applications, as well as collaborative computing initiatives. For example, a shared data model may be used to provide individual or shared presentation and interactions based on central nervous system sensing relative to user 4602 and each user in a group 4610 of users. In some cases, one of users 4610 may control interactions via neuronal-based data and collaborative neuronal-based sensing. The processing may be configured to determine which user may be selected for control. Note further that any human-machine interface 4630 or a remote computing system may be configured based on analysis of neuronal activity data for users 4602 in the aggregate to determine which commands or interactions are to be applied to an application.

In some examples, human-machine interface 4630 may also be configured to passively detect intents and thoughts so as to operate as "neuronal butler," whereby human-machine interface 4630 may determine a task user 4602 desires to focus on, presents options, track neural response, and performs interactions.

Figure 47:
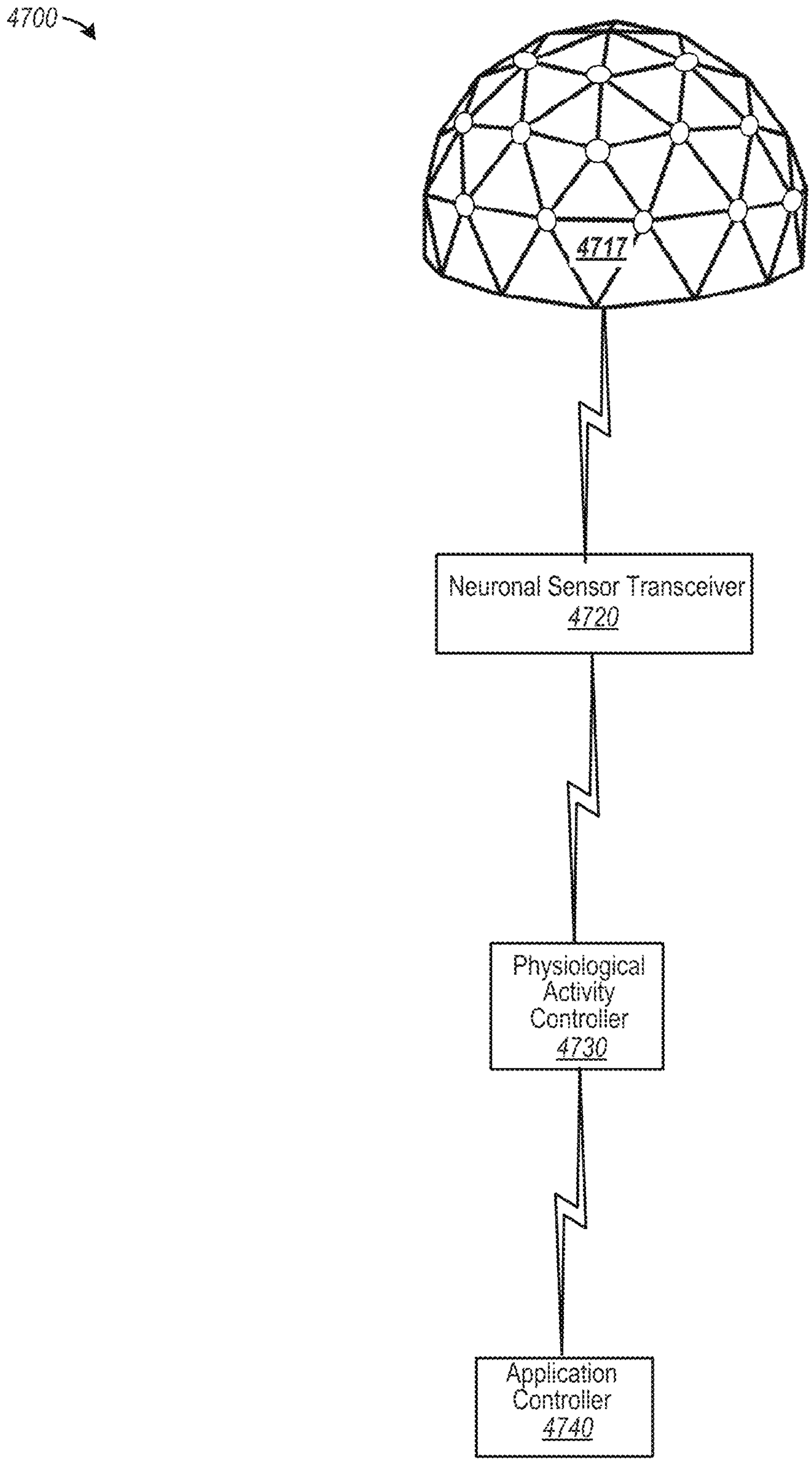
FIG. 47 is a diagram depicting a portion of a human-machine interface, according to some embodiments.

FIG. 47 is a diagram depicting a portion of a human-machine interface, according to some embodiments. Diagram 4700 depicts an array 4717 coupled to a neuronal sensor transceiver 4720, which, in turn is coupled via a physiological activity controller 4730 to an application controller 4740. According to some examples, elements depicted in diagram 4700 of FIG. 47 may include structures and/or functions as similarly-named or similarly-numbered elements depicted in other drawings.

One or more of elements shown in diagram 4700 may perform any of the following functions to enhance operability of a human-machine interface. For example, a human-machine interface may implement a sensitivity matrix as a way to understand, for example, that a single sensor may be optimally sensitive in one region in space than other sensors or at other regions in space. As an example, a sensitivity matrix may be used to compute a 3-D distribution of neural activity from a 2-D sensor-based set of data measurements at the surface of the brain. A matrix may provide a vehicle to understand to what extent different sensors at the surfaces are sensitive to specific regions in the 3-D view, by providing some transformations to determine 3-D view. As such, a human-machine interface may implement sensitivity matrix to, for example, generate 3-D imagery for computer tomography applications.

In some examples, a human-machine interface may be configured to provide dynamic reconfiguration of sensors. In some cases, combinations of sensors may be more sensitive to particular spatiotemporal shapes than others. In some examples, human-machine interface may implement "just-in-time priming" so as to load and/or configure processing on the basis of what is expected next given current activity, and/or a the basis of what is to be looked for next given current activity. Reconfigurable hardware processor, such as reconfigurable FPGAs, may be implemented.

A human-machine interface may be configured to provide feedback to optimize recognition, form patterns visually in a way a user can respond to intuitively and/or immediately, optimize feedback to encourage rapid recognition and/or detection, facilitate offline machine learning, either in a remote computer system or locally in a client, or both, etc. A human-machine interface may be configured to pool learning from multiple users and then to re-specialize to specific users, morph sets of neuronal activity data over a population to form one or more generic "brain" models, learn mapping of neuronal activity back to a user or a demographic of users and to identify regions and/or tasks that correlate well across individuals.

According to some embodiments, the term "circuit" can refer, for example, to any system including a number of components through which current flows to perform one or more functions, the components including discrete and complex components. Examples of discrete components include transistors, resistors, capacitors, inductors, diodes, and the like, and examples of complex components include memory, processors, analog circuits, digital circuits, and the like, including field-programmable gate arrays ("FPGAs"), application-specific integrated circuits ("ASICs"). Therefore, a circuit can include a system of electronic components and logic components (e.g., logic configured to execute instructions, such that a group of executable instructions of an algorithm, for example, and, thus, is a component of a circuit). According to some embodiments, the term "module" can refer, for example, to an algorithm or a portion thereof, and/or logic implemented in either hardware circuitry or software, or a combination thereof (i.e., a module can be implemented as a circuit). In some embodiments, algorithms and/or the memory in which the algorithms are stored are "components" of a circuit. Thus, the term "circuit" can also refer, for example, to a system of components, including algorithms. These can be varied and are not limited to the examples or descriptions provided.

Although the foregoing examples have been described in some detail for purposes of clarity of understanding, the above-described inventive techniques are not limited to the details provided. There are many alternative ways of implementing the above-described invention techniques. The disclosed examples are illustrative and not restrictive.

An apparatus comprising of an array of neuronal activity sensors adapted to conform to a portion of head adjacent a portion of a brain to detect a subset of neuronal activity types, the array of neuronal activity sensors comprising of a subset of neuronal activity sensors, each of which comprises of one or more electrodes configured to impart an alternating stimulus field into a plurality of biological tissues; and one or more magnetic field elements are configured to receive a magnetic field associated with the alternating electric field; a neuronal sensor transceiver configured to temporally drive a magnitude of a stimulus signal in association with the one or more electrodes to vary the magnitude electric field at different regions of the brain at which the one or more magnetic field elements are disposed and further configured to receive a modulated response signal; and a physiological activity processor configured to extract the data representing the characteristic of neuron activity at multiple points in time. In the apparatus comprising of an array of neuronal activity sensors, an amount of the data representing the characteristic of neuron activity at the multiple points in time is greater than a single point in time. In the apparatus comprising of an array of neuronal activity sensors, the modulated response signal comprises of a modulated induced current during an interval of time. In the apparatus comprising of an array of neuronal activity sensors, the neuronal sensor transceiver is further configured to temporally drive the magnitude of the stimulus signal in a direction substantially parallel to a layer including the one or more electrodes. A portion of this layer is coextensive with an XY plane. In the apparatus comprising of an array of neuronal activity sensors, the neuronal sensor transceiver is further configured to spatially drive a modulated depth of the stimulus signal in a direction substantially orthogonal to a layer including the one or more electrodes. The direction of the modulated depth of the stimulus signal is substantially orthogonal to the layer is parallel to a Z axis. In the apparatus comprising of an array of neuronal activity sensors, the neuronal sensor transceiver is further configured to modify a frequency of the stimulus signal to modify the modulated depth of the stimulus signal. The apparatus comprising of an array of neuronal activity sensors further comprises of another subset of neuronal activity sensors, each of which comprises of one or more light emitting devices configured to impart a light field into the plurality of biological tissues; and one or more light receiving elements configured to receive a response light field from the plurality of biological tissues. The apparatus comprising of an array of neuronal activity sensors further comprises of another subset of neuronal activity sensors, each of which comprises of one or more magnetic drive coils as the stimuli elements to impart the stimulus field as an induced magnetic field into the plurality of biological components; and one or more search coils as the response elements.

An apparatus comprising of a physiological activity controller including an interface configured to receive one or more subsets of data representing neuronal activity, the physiological activity controller further configured to access a repository of data representing a plurality of neuronal activity patterns; a physiological activity correlator configured to select a subset of the neuronal activity patterns and to identify an associated subset of data representing neuronal activity, wherein at least one of the subset of the neuronal activity patterns is representative of a neuronal state. In the apparatus comprising of a physiological activity controller including an interface configured to receive one or more subsets of data representing neuronal activity, the one or more subsets of data representing neuronal activity comprise of at least two subset of data representing neuronal activity including different amounts of data at different resolutions. In the apparatus comprising of a physiological activity controller including an interface configured to receive one or more subsets of data representing neuronal activity, the different resolutions of different amounts of data representing neuronal activity in one or more subsets of data are selected as a function of predicted neuronal activity. In the apparatus comprising of a physiological activity controller including an interface configured to receive one or more subsets of data representing neuronal activity, the physiological activity controller is further configured to transmit sensor control data to a neuronal sensor transceiver, the sensor control data configured to cause the neuronal sensor transceiver to select a first subset of an array of sensors at a first resolution and a second subset of an array of sensors at a second resolution. In the apparatus comprising of a physiological activity controller including an interface configured to receive one or more subsets of data representing neuronal activity, the physiological activity controller configured to transmit sensor control data to a neuronal sensor transceiver, the sensor control data is configured to cause selection of bio-inductance sensors. In the apparatus comprising of a physiological activity controller including an interface configured to receive one or more subsets of data representing neuronal activity, the physiological activity controller is further configured to generate sensor control data as a function of contextual data to select a subset of an array of sensors based on context. In the apparatus comprising of a physiological activity controller including an interface configured to receive one or more subsets of data representing neuronal activity, the physiological activity controller is further configured to generate sensor control data as a function of physiological data to select a subset of an array of sensors based on one or more physiological characteristics. In the apparatus comprising of a physiological activity controller including an interface configured to receive one or more subsets of data representing neuronal activity, the physiological activity controller is further configured to select a subset of the neuronal activity patterns based on a type of activity in which a user is engaged. The apparatus comprising of a physiological activity controller including an interface configured to receive one or more subsets of data representing neuronal activity further comprises of a physiological activity characterizer configured to generate the subset of the neuronal activity patterns. The apparatus comprising of a physiological activity controller including an interface configured to receive one or more subsets of data representing neuronal activity comprising of a physiological activity characterizer configured to generate the subset of the neuronal activity patterns further comprises of a feedback analyzer configured to facilitate formation of the subset of the neuronal activity patterns based on feedback to characterize the neuronal state.

An apparatus comprising of an array of physiological activity sensors adapted to couple to a portion of a body to detect a subset of physiological activity types; and a physiological sensor transceiver configured to selectably drive the stimulus field in association with the one or more stimuli elements to generate the stimulus field and further configured to receive a response signal based on the return field including data representing an amount of physiological activity. In the apparatus comprising of an array of physiological activity sensors adapted to couple a portion of a body to detect a subset of physiological activity types, a physiological sensor transceiver comprises of a neuronal sensor transceiver comprising of a registration system configured to detect a displacement of at least one physiological activity sensor; and a self-registration controller configured to calibrate at least a sub-array of the physiological activity sensors to re-align to a reference portion. In the apparatus comprising of an array of physiological activity sensors adapted to couple a portion of a body to detect a subset of physiological activity types, the array of physiological activity sensors comprises of a subset of physiological activity sensors, each of which comprises of one or more stimuli elements configured to impart a stimulus field into a plurality of biological components; and one or more response elements configured to capture a return field exiting the plurality of biological component.

The invention claimed is:

1. An apparatus comprising:

an array of neuronal activity sensors adapted to conform to a portion of head adjacent a portion of a brain to detect a subset of neuronal activity types, the array of neuronal activity sensors comprising;

a subset of neuronal activity sensors, each of which comprises:

one or more electrodes configured to impart an electric field into a plurality of biological tissues; and one or more magnetic field elements configured to receive a magnetic field associated with the electric field; and a neuronal sensor transceiver configured to selectably drive a stimulus signal in association with the one or more electrodes to generate the electric field and further configured to receive a response signal that includes data representing an amount of neuron activity; and a physiological activity processor configured to extract the data representing an amount of neuron activity from the response signal and to determine a neuronal state, wherein the one or more magnetic field elements comprises:

a plurality of overlapping coils, wherein the physiological activity processor is configured to selectably control the driving of a subset of the overlapping coils via the neuronal sensor transceiver.

2. The apparatus of claim 1 wherein the response signal comprises:

an induced current.

3. The apparatus of claim 1 wherein the one or more magnetic field elements comprises:

at least one coil.

4. The apparatus of claim 1 wherein the one or more magnetic field elements comprises:

at least two coils.

5. The apparatus of claim 4 wherein the at least two coils comprise:

a first coil having a first diameter and a winding in a first direction;

a second coil having a second diameter and a winding in a second direction, wherein one of the first coil and the second coil is configured to generate an induced current to cancel another induced current generated by the other of the first coil and the second coil.

6. The apparatus of claim 5 wherein at least two coils include concentric coils, the neuronal sensor transceiver is configured to drive a first stimulus signal at a first range of frequencies to a first depth into the biological tissues, and drive a second stimulus signal at a second range of frequencies to a second depth into the biological tissues.

7. The apparatus of claim 1 wherein the subset of neuronal activity sensors comprises:

a plurality of neuronal activity sensors arranged spatially to be disposed to different portions of the brain; and a plurality of switches controlled by the neuronal sensor transceiver, at least two switches being configured to implement a magnetic field element.

8. The apparatus of claim 1 wherein the physiological activity processor is further configured to determine a value representative of an aggregate of action potentials as the amount of neuron activity.

9. An apparatus comprising:

an array of neuronal activity sensors adapted to conform to a portion of head adjacent a portion of a brain to detect a subset of neuronal activity types, the array of neuronal activity sensors comprising;

a subset of neuronal activity sensors, each of which comprises:

one or more electrodes configured to impart an electric field into a plurality of biological tissues; and one or more magnetic field elements configured to receive a magnetic field associated with the electric field; and a neuronal sensor transceiver configured to selectably drive a stimulus signal in association with the one or more electrodes to generate the electric field and further configured to receive a response signal that includes data representing an amount of neuron activity; and a physiological activity processor configured to extract the data representing an amount of neuron activity from the response signal and to determine a neuronal state, wherein the one or more magnetic field elements comprise:

a first coil having a first diameter and a winding in a first direction;

a second coil having a second diameter and a winding in a second direction, wherein one of the first coil and the second coil is configured to generate an induced current to cancel another induced current generated by the other of the first coil and the second coil to facilitate determination of the neuronal state associated with the portion of the brain.

10. The apparatus of claim 9 wherein the first coil and the second coil comprises:

concentric coils, wherein the neuronal sensor transceiver is configured to drive a first stimulus signal at a first range of frequencies to a first depth into the biological tissues, and drive a second stimulus signal at a second range of frequencies to a second depth into the biological tissues.

11. The apparatus of claim 9 wherein the subset of neuronal activity sensors comprises:

a plurality of neuronal activity sensors arranged spatially to be disposed to different portions of the brain; and a plurality of switches controlled by the neuronal sensor transceiver, at least two switches being configured to implement a magnetic field element.

12. The apparatus of claim 9 wherein the physiological activity processor is further configured to determine a value representative of an aggregate of action potentials as the amount of neuron activity.

* * * * *